(12) United States Patent
Comrie et al.

(10) Patent No.: US 12,263,221 B2
(45) Date of Patent: Apr. 1, 2025

(54) CHIMERIC ANTIGEN RECEPTOR COMPRISING BCMA NANOBODY LINKED TO A CHIMERIC INTRACELLULAR SIGNALING DOMAIN

(71) Applicant: Neomics Pharmaceuticals LLC, Gaithersburg, MD (US)

(72) Inventors: William A. Comrie, Silver Spring, MD (US); Wenshan Hao, Parsippany, NJ (US)

(73) Assignee: Neomics Pharmaceuticals LLC, Rockville, MD (US)

( * ) Notice: Subject to any disclaimer, the term of this patent is extended or adjusted under 35 U.S.C. 154(b) by 0 days.

(21) Appl. No.: 18/347,487

(22) Filed: Jul. 5, 2023

(65) Prior Publication Data

US 2024/0009309 A1 Jan. 11, 2024

Related U.S. Application Data

(60) Provisional application No. 63/358,399, filed on Jul. 5, 2022.

(51) Int. Cl.
| | | |
|---|---|---|
| *A61K 39/00* | (2006.01) | |
| *A61P 35/00* | (2006.01) | |
| *C07K 14/705* | (2006.01) | |
| *C07K 14/725* | (2006.01) | |
| *C07K 16/28* | (2006.01) | |
| *C12N 15/62* | (2006.01) | |

(52) U.S. Cl.
CPC .. *A61K 39/464417* (2023.05); *A61K 39/4611* (2023.05); *A61K 39/4631* (2023.05); *A61P 35/00* (2018.01); *C07K 14/7051* (2013.01); *C07K 14/70521* (2013.01); *C07K 16/2878* (2013.01); *C12N 15/62* (2013.01); *A61K 2239/13* (2023.05); *A61K 2239/22* (2023.05); *A61K 2239/48* (2023.05); *C07K 2317/569* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 11,041,021 B2 | 6/2021 | Chang et al. | |
| 2017/0137515 A1* | 5/2017 | Chang | A61K 39/001186 |
| 2017/0362295 A1* | 12/2017 | June | C07K 14/705 |
| 2020/0281974 A1 | 9/2020 | Barber | |
| 2022/0218746 A1* | 7/2022 | Zhang | C12N 5/0646 |
| 2022/0220186 A1 | 7/2022 | Comrie et al. | |

FOREIGN PATENT DOCUMENTS

| | | | |
|---|---|---|---|
| WO | WO-2013019615 A2 | 2/2013 | |
| WO | WO-2018058431 A1 | 4/2018 | |
| WO | WO-2018132506 A1 | 7/2018 | |
| WO | WO-2018161017 A1 | 9/2018 | |
| WO | WO-2018231759 A1 | 12/2018 | |
| WO | WO-2019118508 A1 | 6/2019 | |
| WO | WO-2019195492 A1 | 10/2019 | |
| WO | WO-2019217913 A1 | 11/2019 | |
| WO | WO-2020038146 A1 * | 2/2020 | A61K 35/17 |
| WO | WO-2020086742 A1 | 4/2020 | |
| WO | WO-2020212986 A1 | 10/2020 | |
| WO | WO-2022147525 A1 | 7/2022 | |

OTHER PUBLICATIONS

Li et al JCI Insight. ; 3(18): e121322, 1-18 (Year: 2018).*
Feucht et al Nature Medicine, 25, 82-88 (Year: 2018).*
Adler, A. et al. "Betting on improved cancer immunotherapy by doubling down on CD134 and CD137 co-stimulation," Oncoimmunology, Jan. 1, 2013, Retrieved from the Internet: URL: https://www.ncbi.nlm.nih.gov/pmc/articles/PMC3583935/pdf/onci-2-e22837.pdf, 11 pages.
Ajina, A. et al. "Strategies to Address Chimeric Antigen Receptor Tonic Signaling," Molecular Cancer Therapeutics, Sep. 1, 2018, 17(9):1795-1815.
Allenspach, E.J., et al., "ERM-Dependent Movement of CD43 Defines a Novel Protein Complex Distal to the Immunological Synapse." Immunity. Nov. 2001, 15(5):739-50.
Ankri C., et al., "Human T Cells Engineered To Express a Programmed Death 1/28 Costimulatory Retargeting Molecule Display Enhanced Antitumor Activity." J Immunol., Oct. 15, 2013, 191(8):4121-9, Epub Sep. 11, 2013.
Carpenito C., et al., "Control of large, established tumor xenografts with genetically retargeted human T cells containing CD28 and CD137 domains." PNAS, Mar. 3, 2009, 106(9):3360-3365.
Croft et al. "The Significance of OX40 and OX40L to Tcell Biology and Immune Disease." Immunological reviews, May 2009, 229(1):173-191 (28 pages total).
D'Angelo S.P., et al., "Antitumor Activity Associated with Prolonged Persistence of Adoptively Transferred NY-ESO-1 $^{c259}$ T Cells in Synovial Sarcoma." Cancer Discov. Aug. 2018, 8(8): 944-957. Epub Jun. 11, 2018.
Ecsedi, M., et al., "The anti-cancer potential of T cell receptor-engineered T cells. Trends Cancer." Jan. 2021, 7(1):48-56 (17 total pages).
Everson, R.G., et al., "Efficacy of systemic adoptive transfer immunotherapy targeting NY-ESO-1 for glioblastoma." Neuro Oncol. Mar. 2016, 18(3):368-78. Epub Sep. 1, 2015.
Fellermeier, S et al. "Advancing targeted co-stimulation with antibody-fusion proteins by introducing TNF superfamily members in a single-chain format," Oncoimmunology, Sep. 27, 2016, 5(11), 11 pages.

(Continued)

*Primary Examiner* — Anoop K Singh
(74) *Attorney, Agent, or Firm* — COOLEY LLP; Chen Chen; Natalie M. Hendrick

(57) ABSTRACT

The present application relates to functionally improved third generation BCMA-CARs comprising modified intracellular co-stimulatory domains, which can be used in adoptive cell therapy, e.g., in treatment of diseases and disorders such as cancer.

7 Claims, 32 Drawing Sheets

Specification includes a Sequence Listing.

(56) References Cited

OTHER PUBLICATIONS

GenBank Accession No. AAA37396.1, "CD28, partial [Mus musculus]," Feb. 15, 1994, 1 page.
GenBank Accession No. AAA51944.1, "glycoprotein CD28 [Homo sapiens]," Aug. 1, 2016, 2 pages.
GenBank Accession No. AAA51945.1, "glycoprotein CD28 [Homo sapiens]," Aug. 1, 2016, 2 pages.
GenBank Accession No. AAA60581.1, "T-cell-specific homodimer surface protein precursor [Homo sapiens]," Jan. 13, 1995, 2 pages.
GenBank Accession No. AAA62478.1, "ILA= induced by lymphocyte activation; similar to Human receptor protein encoded by GenBank Accession No. U03397," Feb. 28, 1995, 1 page.
GenBank Accession No. AAF33792.1, "T-cell specific surface glycoprotein CD28 isoform 1 [Homo sapiens]," Mar. 14, 2002, 2 pages.
GenBank Accession No. AAF33793.1, "T-cell specific surface glycoprotein CD28 isoform 2 [Homo sapiens]," Mar. 14, 2002, 1 page.
GenBank Accession No. AAF33794.1, "T-cell specific surface glycoprotein CD28 isoform 3 [Homo sapiens]," Mar. 14, 2002, 2 pages.
GenBank Accession No. AAG48732.1, "inducible costimulatory protein [Mus musculus]," Jun. 10, 2016, 2 pages.
GenBank Accession No. AAH06196.1, "Tumor necrosis factor receptor superfamily, member 9 [Homo sapiens]," Jul. 15, 2006, 2 pages.
GenBank Accession No. AAH28006.1, "ICOS protein [Homo sapiens]," Oct. 6, 2003, 3 pages.
GenBank Accession No. AAH28210.1, "inducible T-cell costimulator [Homo sapiens]," Jul. 15, 2016, 3 pages.
GenBank Accession No. AAH28507.1, "Tumor necrosis factor receptor superfamily, member 9 [Mus musculus]," Nov. 7, 2006, 2 pages.
GenBank Accession No. AAH34852.1, "Inducible T-cell costimulator [Mus musculus]," Jul. 21, 2006, 3 pages.
GenBank Accession No. AAH64058.1, "CD28 antigen [Mus musculus]," Jul. 15, 2006, 3 pages.
GenBank Accession No. AAH93698.1, "CD28 molecule [Homo sapiens]," Jul. 15, 2006, 2 pages.
GenBank Accession No. AAH97483.1, "Tumor necrosis factor receptor superfamily, member 9 [Rattus norvegicus]," Jun. 9, 2008, 2 pages.
GenBank Accession No. AAI05071.1, "Tumor necrosis factor receptor superfamily, member 4 [Homo sapiens]," Jul. 21, 2006, 2 pages.
GenBank Accession No. AAI05073.1, "Tumor necrosis factor receptor superfamily, member 4 [Homo sapiens]," Jul. 21, 2006, 2 pages.
GenBank Accession No. AAI12086.1, "CD28 antigen [Homo sapiens]," Jun. 6, 2006, 2 pages.
GenBank Accession No. AAI39240.1, "Tumor necrosis factor receptor superfamily, member 4 [Mus musculus]," May 12, 2008, 2 pages.
GenBank Accession No. AAI39267.1, "Tumor necrosis factor receptor superfamily, member 4 [Mus musculus]," Feb. 11, 2009, 2 pages.
GenBank Accession No. AAL40931.1, "CD28 antigen, partial [Homo sapiens]," Jul. 26, 2016, 2 pages.
GenBank Accession No. AAL40933.1, "inducible T-cell costimulator [Homo sapiens]," Nov. 18, 2022, 2 pages.
GenBank Accession No. AAL40934.1, "inducible T-cell costimulator [Homo sapiens]," Nov. 18, 2022, 2 pages.
GenBank Accession No. AAM00909.1, "inducible costimulator [Homo sapiens]," Jun. 10, 2016, 2 pages.
GenBank Accession No. AAX93073.1, "unknown [Homo sapiens]," Apr. 16, 2005, 3 pages.
GenBank Accession No. AAY24123.1, "unknown [Homo sapiens]," Apr. 30, 2005, 3 pages.
GenBank Accession No. ABG77997.1, "CD28 precursor 6m, partial [Macaca fascicularis]," Jul. 14, 2016, 2 pages.
GenBank Accession No. ABG77998.1, "CD28 precursor P, partial [Macaca fascicularis]," Jul. 14, 2016, 2 pages.
GenBank Accession No. ABH06891.1, "CD28 [Macaca mulatta]," Oct. 20, 2006, 2 pages.
GenBank Accession No. ABH06892.1, "CD28 [Macaca fascicularis]," Oct. 20, 2006, 2 pages.
GenBank Accession No. ABH08508.1, "CD28 [Macaca mulatta]," Aug. 11, 2006, 2 pages.
GenBank Accession No. ABH08509.1, "CD28 [Macaca fascicularis]," Aug. 11, 2006, 2 pages.
GenBank Accession No. ABI30212.1, "CD137 antigen precursor [Mus musculus]," Jun. 18, 2007, 2 pages.
GenBank Accession No. ABI30213.1, "secreted CD137 antigen precursor [Mus musculus]," Jun. 18, 2007, 2 pages.
GenBank Accession No. ABK41938.1, "CD28 molecule [Homo sapiens]," Nov. 13, 2006, 2 pages.
GenBank Accession No. ABQ09493.1, "CD28 [Callithrix jacchus]," May 7, 2007, 2 pages.
GenBank Accession No. ABY47575.1, "CD137 [Macaca fascicularis]," Dec. 5, 2008, 2 pages.
GenBank Accession No. ABY47576.1, "CD137 variant [Macaca fascicularis]," Dec. 5, 2008, 1 page.
GenBank Accession No. ABY47577.1, "CD137 variant [Macaca fascicularis]," Dec. 5, 2008, 1 page.
GenBank Accession No. ABY47578.1, "CD137 variant [Macaca fascicularis]," Dec. 5, 2008, 2 pages.
GenBank Accession No. ACX50463.1, "inducible T-cell costimulator [Mus musculus]," Oct. 13, 2009, 2 pages.
GenBank Accession No. ACX50464.1, "inducible T-cell costimulator [Mus musculus]," Oct. 13, 2009, 2 pages.
GenBank Accession No. AFH29328.1, "inducible T-cell costimulator precursor [Macaca mulatta]," Nov. 4, 2014, 2 pages.
GenBank Accession No. AIC48451.1, "CD28, partial [synthetic construct]," Mar. 19, 2015, 2 pages.
GenBank Accession No. AIC51287.1, "Icos, partial [synthetic construct]," Mar. 19, 2015, 2 pages.
GenBank Accession No. AIC60036.1, "Icos, partial [synthetic construct]," Mar. 19, 2015, 2 pages.
GenBank Accession No. BAD99404.1, "4-1BB homolog [Rattus norvegicus]," Jun. 7, 2005, 1 page.
GenBank Accession No. BAE32724.1, "unnamed protein product [Mus musculus]," Oct. 6, 2010, 4 pages.
GenBank Accession No. CAA34897.1, "precursor (AA -19 to 252) [Rattus sp.]," Sep. 24, 2008, 2 pages.
GenBank Accession No. CAA39003.1, "CD28 [Rattus norvegicus]," Sep. 24, 2008, 3 pages.
GenBank Accession No. CAA59476.1, "ox40 [Mus musculus]," Nov. 14, 2006, 2 pages.
GenBank Accession No. CAA79772.1, "Ox40 [Mus musculus]," Sep. 24, 2008, 2 pages.
GenBank Accession No. CAB71153.1, "surface protein [Mus musculus]," Sep. 23, 2008, 2 pages.
GenBank Accession No. CAB96543.1, "CD134 antigen [Homo sapiens]," Nov. 14, 2006, 2 pages.
GenBank Accession No. CAC06612.1, "inducible T-cell costimulator [Homo sapiens]," Oct. 7, 2008, 2 pages.
GenBank Accession No. CAC29237.1, "putative CD28 protein [Homo sapiens]," Apr. 15, 2005, 2 pages.
GenBank Accession No. CAD57003.1, "T-cell-specific surface glycoprotein [Homo sapiens]," Oct. 7, 2008, 2 pages.
GenBank Accession No. CAD59742.1, "inducible costimulator protein [Homo sapiens]," Nov. 8, 2003, 2 pages.
GenBank Accession No. CAM13241.1, "inducible T-cell costimulator [Mus musculus]," Jan. 15, 2009, 3 pages.
GenBank Accession No. CAM13242.1, "inducible T-cell costimulator [Mus musculus]," Jan. 15, 2009, 3 pages.
GenBank Accession No. CAM13249.1, "CD28 antigen [Mus musculus]," Jan. 15, 2009, 3 pages.
GenBank Accession No. EAW56278.1, "tumor necrosis factor receptor superfamily, member 4, isoform CRA_a [Homo sapiens]," Mar. 23, 2015, 2 pages.
GenBank Accession No. EAW70347.1, "CD28 antigen (Tp44), isoform CRA_a, partial [Homo sapiens]," Mar. 23, 2015, 2 pages.
GenBank Accession No. EAW70348.1, "CD28 antigen (Tp44), isoform CRA_b [Homo sapiens]," Mar. 23, 2015, 2 pages.

(56) References Cited

OTHER PUBLICATIONS

GenBank Accession No. EAW70349.1, "CD28 antigen (Tp44), isoform CRA_c [*Homo sapiens*]," Mar. 23, 2015, 2 pages.
GenBank Accession No. EAW70350.1, "CD28 antigen (Tp44), isoform CRA_d, partial [*Homo sapiens*]," Mar. 23, 2015, 2 pages.
GenBank Accession No. EAW70355.1, "inducible T-cell co-stimulator, isoform CRA_a [*Homo sapiens*]," Mar. 23, 2015, 2 pages.
GenBank Accession No. EAW70356.1, "inducible T-cell co-stimulator, isoform CRA_b [*Homo sapiens*]," Mar. 23, 2015, 2 pages.
GenBank Accession No. EAW70357.1, "inducible T-cell co-stimulator, isoform CRA_c, partial [*Homo sapiens*]," Mar. 23, 2015, 2 pages.
GenBank Accession No. EDL00156.1, "CD28 antigen [Mus musculus]," Jul. 26, 2016, 3 pages.
GenBank Accession No. EDL00161.1, "inducible T-cell co-stimulator [Mus musculus]," Jul. 26, 2016, 3 pages.
GenBank Accession No. EDL15067.1, "tumor necrosis factor receptor superfamily, member 4 [Mus musculus]," Jul. 26, 2016, 2 pages.
GenBank Accession No. EDL81196.1, "similar to T-cell antigen 4-1BB precursor -mouse, isoform CRA_a [Rattus norvegicus]," Jul. 26, 2016, 2 pages.
GenBank Accession No. EDL81353.1, "tumor necrosis factor receptor superfamily, member 4 [Rattus norvegicus]," Jul. 26, 2016, 2 pages.
GenBank Accession No. EDL98921.1, "inducible T-cell co-stimulator, isoform CRA_a [Rattus norvegicus]," Jul. 26, 2016, 2 pages.
GenBank Accession No. EDL98922.1, "inducible T-cell co-stimulator, isoform CRA_b [Rattus norvegicus]," Jul. 26, 2016, 2 pages.
GenBank Accession No. EDL98926.1, "CD28 antigen [Rattus norvegicus]," Jul. 26, 2016, 3 pages.
GenBank Accession No. EHB16663.1, "Tumor necrosis factor receptor superfamily member 9 [Heterocephalus glaber]," Mar. 14, 2015, 2 pages.
GenBank Accession No. KFO38282.1, "Tumor necrosis factor receptor superfamily member 9 [Fukomys damarensis]," Sep. 4, 2014, 2 pages.
GenBank Accession No. U03397.1, "Human receptor protein 4-1BB mRNA, complete cds," Nov. 27, 1994, 2 pages.
GenBank NCBI Reference Sequence: NP_001020944.1, "tumor necrosis factor receptor superfamily member 9 precursor [Rattus norvegicus]," Feb. 1, 2021, 2 pages.
GenBank NCBI Reference Sequence: NP_001036106.2, "T-cell-specific surface glycoprotein CD28 precursor [Macaca mulatta]," Jun. 25, 2020, 2 pages.
GenBank NCBI Reference Sequence: NP_001070976.1, "tumor necrosis factor receptor superfamily member 9 isoform 2 precursor [Mus musculus]," Apr. 17, 2022, 3 pages.
GenBank NCBI Reference Sequence: NP_001070977.1, "tumor necrosis factor receptor superfamily member 9 isoform 1 precursor [Mus musculus]," Apr. 17, 2022, 3 pages.
GenBank NCBI Reference Sequence: NP_001162597.1, "transmembrane and immunoglobulin domain-containing protein 2 isoform 2 precursor [*Homo sapiens*]," Jun. 19, 2022, 4 pages.
GenBank NCBI Reference Sequence: NP_001230006.1, "T-cell-specific surface glycoprotein CD28 isoform 2 precursor [*Homo sapiens*]," May 22, 2022, 3 pages.
GenBank NCBI Reference Sequence: NP_001230007.1, "T-cell-specific surface glycoprotein CD28 isoform 3 precursor [*Homo sapiens*]," May 23, 2022, 3 pages.
GenBank NCBI Reference Sequence: NP_001253918.1, "inducible T-cell costimulator precursor [Macaca mulatta]," Feb. 21, 2022, 2 pages.
GenBank NCBI Reference Sequence: NP_001274262.1, "T-cell-specific surface glycoprotein CD28 precursor [Macaca fascicularis]," Jun. 30, 2020, 2 pages.
GenBank NCBI Reference Sequence: NP_001284491.1, "tumor necrosis factor ligand superfamily member 4 isoform 2 [*Homo sapiens*]," Jun. 6, 2022, 3 pages.
GenBank NCBI Reference Sequence: NP_001295161.1, "transmembrane and immunoglobulin domain-containing protein 2 isoform 3 [*Homo sapiens*]," Jun. 19, 2022, 3 pages.
GenBank NCBI Reference Sequence: NP_001552.1, "interleukin-activated receptor, homolog of mouse Ly63 [*Homo sapiens*]," Mar. 19, 1999, 2 pages.
GenBank NCBI Reference Sequence: NP_003317.1, "tumor necrosis factor ligand superfamily member 4 isoform 1 [*Homo sapiens*]," Jun. 1, 2022, 3 pages.
GenBank NCBI Reference Sequence: NP_003318.1, "tumor necrosis factor receptor superfamily member 4 precursor [*Homo sapiens*]," Jul. 18, 2022, 4 pages.
GenBank NCBI Reference Sequence: NP_006130.1, "T-cell-specific surface glycoprotein CD28 isoform 1 precursor [*Homo sapiens*]," May 22, 2022, 4 pages.
GenBank NCBI Reference Sequence: NP_031668.3, "T-cell-specific surface glycoprotein CD28 precursor [Mus musculus]," Jul. 19, 2022, 4 pages.
GenBank NCBI Reference Sequence: NP_033430.1, "tumor necrosis factor ligand superfamily member 9 [Mus musculus]," May 8, 2022, 3 pages.
GenBank NCBI Reference Sequence: NP_033478.1, "tumor necrosis factor ligand superfamily member 4 [Mus musculus]," Mar. 6, 2022, 3 pages.
GenBank NCBI Reference Sequence: NP_035742.1, "tumor necrosis factor receptor superfamily member 9 isoform 1 precursor [Mus musculus]," Apr. 17, 2022, 3 pages.
GenBank NCBI Reference Sequence: NP_035789.1, "tumor necrosis factor receptor superfamily member 4 precursor [Mus musculus]," Jul. 3, 2022, 3 pages.
GenBank NCBI Reference Sequence: NP_036224.1, "inducible T-cell costimulator precursor [*Homo sapiens*]," Apr. 17, 2022, 4 pages.
GenBank NCBI Reference Sequence: NP_037181.1, "tumor necrosis factor receptor superfamily member 4 precursor [Rattus norvegicus]," May 28, 2022, 3 pages.
GenBank NCBI Reference Sequence: NP_037253.2, "T-cell-specific surface glycoprotein CD28 precursor [Rattus norvegicus]," Jun. 11, 2022, 4 pages.
GenBank NCBI Reference Sequence: NP_059508.2, "inducible T-cell costimulator precursor [Mus musculus]," May 15, 2022, 4 pages.
GenBank NCBI Reference Sequence: NP_072132.1, "inducible T-cell costimulator precursor [Rattus norvegicus]," Jan. 12, 2022, 3 pages.
GenBank NCBI Reference Sequence: NP_852049.1, "tumor necrosis factor ligand superfamily member 9 [Rattus norvegicus]," Feb. 5, 2021, 3 pages.
GenBank NCBI Reference Sequence: XP_001090870.1, "tumor necrosis factor receptor superfamily member 4 [Macaca mulatta]," Apr. 26, 2019, 2 pages.
GenBank NCBI Reference Sequence: XP_003890998.2, "tumor necrosis factor receptor superfamily member 4 isoform X1 [Papio anubis]," Nov. 20, 2019, 2 pages.
GenBank NCBI Reference Sequence: XP_003907887.1, "inducible T-cell costimulator isoform X2 [Papio anubis]," Nov. 20, 2019, 2 pages.
GenBank NCBI Reference Sequence: XP_003925677.1, "inducible T-cell costimulator isoform X1 [Saimiri boliviensis boliviensis]," Feb. 12, 2021, 2 pages.
GenBank NCBI Reference Sequence: XP_003939714.1, "Predicted: tumor necrosis factor receptor superfamily member 4 isoform X2 [Saimiri boliviensis boliviensis]," Nov. 24, 2014, 2 pages.
GenBank NCBI Reference Sequence: XP_004851403.1, "T-cell-specific surface glycoprotein CD28 [Heterocephalus glaber]," May 23, 2017, 3 pages.
GenBank NCBI Reference Sequence: XP_005545179.1, "tumor necrosis factor receptor superfamily member 4 isoform X2 [Macaca fascicularis]," Dec. 8, 2021, 2 pages.

(56) References Cited

OTHER PUBLICATIONS

GenBank NCBI Reference Sequence: XP_005574075.1, "Predicted: inducible T- cell costimulator [Macaca fascicularis]," Jan. 25, 2016, 2 pages.
GenBank NCBI Reference Sequence: XP_006239534.1, "tumor necrosis factor receptor superfamily member 9 isoform X1 [Rattus norvegicus]," Jan. 21, 2021, 2 pages.
GenBank NCBI Reference Sequence: XP_006245099.1, "inducible T-cell costimulator isoform X1 [Rattus norvegicus]," Jan. 21, 2021, 2 pages.
GenBank NCBI Reference Sequence: XP_006245100.1, "inducible T-cell costimulator isoform X2 [Rattus norvegicus]," Jan. 21, 2021, 2 pages.
GenBank NCBI Reference Sequence: XP_006256322.1, "Icos ligand isoform X1 [Rattus norvegicus]," Jan. 21, 2021, 3 pages.
GenBank NCBI Reference Sequence: XP_006256323.1, "Icos ligand isoform X2 [Rattus norvegicus]," Jan. 21, 2021, 3 pages.
GenBank NCBI Reference Sequence: XP_006256324.1, "Icos ligand isoform X3 [Rattus norvegicus]," Jan. 21, 2021, 3 pages.
GenBank NCBI Reference Sequence: XP_006496201.1, "inducible T-cell costimulator isoform X1 [Mus musculus]," Sep. 21, 2020, 2 pages.
GenBank NCBI Reference Sequence: XP_006496202.1, "inducible T-cell costimulator isoform X1 [Mus musculus]," Sep. 21, 2020, 2 pages.
GenBank NCBI Reference Sequence: XP_006496203.1, "inducible T-cell costimulator isoform X2 [Mus musculus]," Sep. 21, 2020, 2 pages.
GenBank NCBI Reference Sequence: XP_006538787.3, "tumor necrosis factor receptor superfamily member 4 isoform X1 [Mus musculus]," Sep. 21, 2020, 2 pages.
GenBank NCBI Reference Sequence: XP_006710681.1, "tumor necrosis factor receptor superfamily member 9 isoform X1 [Homo sapiens]," Apr. 5, 2022, 2 pages.
GenBank NCBI Reference Sequence: XP_007964137.1, "inducible T-cell costimulator [Chlorocebus sabaeus]," Dec. 1, 2020, 2 pages.
GenBank NCBI Reference Sequence: XP_008762504.1, "tumor necrosis factor receptor superfamily member 9 isoform X1 [Rattus norvegicus]," Jan. 21, 2021, 2 pages.
GenBank NCBI Reference Sequence: XP_008765300.1, "T-cell-specific surface glycoprotein CD28 isoform X1 [Rattus norvegicus]," Jan. 21, 2021, 3 pages.
GenBank NCBI Reference Sequence: XP_008765358.1, "inducible T-cell costimulator isoform X1 [Rattus norvegicus]," Jan. 21, 2021, 2 pages.
GenBank NCBI Reference Sequence: XP_008844474.1, "T-cell-specific surface glycoprotein CD28 [Nannospalax galili]," Jun. 24, 2019, 3 pages.
GenBank NCBI Reference Sequence: XP_008997520.1, "inducible T-cell costimulator [Callithrix jacchus]," Jul. 4, 2020, 2 pages.
GenBank NCBI Reference Sequence: XP_010334714.1, "inducible T-cell costimulator isoform X2 [Saimiri boliviensis boliviensis]," Feb. 12, 2021, 2 pages.
GenBank NCBI Reference Sequence: XP_010350939.1, "inducible T-cell costimulator [Rhinopithecus roxellana]," Sep. 25, 2019, 2 pages.
GenBank NCBI Reference Sequence: XP_010375483.1, "tumor necrosis factor receptor superfamily member 4 [Rhinopithecus roxellana]," Sep. 25, 2019, 2 pages.
GenBank NCBI Reference Sequence: XP_010618177.1, "tumor necrosis factor receptor superfamily member 9 isoform X1 [Fukomys damarensis]," Apr. 23, 2020, 2 pages.
GenBank NCBI Reference Sequence: XP_011248530.1, "tumor necrosis factor receptor superfamily member 9 isoform X1 [Mus musculus]," Sep. 21, 2020, 2 pages.
GenBank NCBI Reference Sequence: XP_011510496.1, "T-cell-specific surface glycoprotein CD28 isoform X1 [*Homo sapiens*]," Apr. 5, 2022, 2 pages.
GenBank NCBI Reference Sequence: XP_011510497.1, "T-cell-specific surface glycoprotein CD28 isoform X2 [*Homo sapiens*]," Nov. 22, 2021, 2 pages.
GenBank NCBI Reference Sequence: XP_011510499.1, "T-cell-specific surface glycoprotein CD28 isoform X3 [*Homo sapiens*]," Nov. 22, 2021, 2 pages.
GenBank NCBI Reference Sequence: XP_011540376.1, "tumor necrosis factor receptor superfamily member 4 isoform X1 [*Homo sapiens*]," Apr. 5, 2022, 2 pages.
GenBank NCBI Reference Sequence: XP_011540377.1, "tumor necrosis factor receptor superfamily member 4 isoform X2 [*Homo sapiens*]," Apr. 5, 2022, 2 pages.
GenBank NCBI Reference Sequence: XP_011540378.1, "tumor necrosis factor receptor superfamily member 4 isoform X3 [*Homo sapiens*]," Apr. 5, 2022, 2 pages.
GenBank NCBI Reference Sequence: XP_011540379.1, "tumor necrosis factor receptor superfamily member 4 isoform X4 [*Homo sapiens*]," Apr. 5, 2022, 2 pages.
GenBank NCBI Reference Sequence: XP_011716285.1, "inducible T-cell costimulator isoform X1 [Macaca nemestrina]," Apr. 24, 2018, 2 pages.
GenBank NCBI Reference Sequence: XP_011716287.1, "inducible T-cell costimulator isoform X2 [Macaca nemestrina]," Apr. 24, 2018, 2 pages.
GenBank NCBI Reference Sequence: XP_011768627.1, "tumor necrosis factor receptor superfamily member 4 [Macaca nemestrina]," Apr. 24, 2018, 2 pages.
GenBank NCBI Reference Sequence: XP_011805287.1, "Predicted: inducible T-cell costimulator isoform X1 [Colobus angolensis palliatus]," Mar. 30, 2015, 2 pages.
GenBank NCBI Reference Sequence: XP_011805288.1, "Predicted: inducible T-cell costimulator isoform X2 [Colobus angolensis palliatus]," Mar. 30, 2015, 2 pages.
GenBank NCBI Reference Sequence: XP_011811769.1, "Predicted: tumor necrosis factor receptor superfamily member 4 [Colobus angolensis palliatus]," Mar. 30, 2015, 2 pages.
GenBank NCBI Reference Sequence: XP_011847866.1, "Predicted: inducible T-cell costimulator isoform X1 [Mandrillus leucophaeus]," Mar. 30, 2015, 2 pages.
GenBank NCBI Reference Sequence: XP_011847867.1, "Predicted: inducible T-cell costimulator isoform X2 [Mandrillus leucophaeus]," Mar. 30, 2015, 2 pages.
GenBank NCBI Reference Sequence: XP_011857387.1, "Predicted: tumor necrosis factor receptor superfamily member 4 [Mandrillus leucophaeus]," Mar. 30, 2015, 2 pages.
GenBank NCBI Reference Sequence: XP_011886512.1, "Predicted: tumor necrosis factor receptor superfamily member 4 isoform X1 [Cercocebus atys], " Mar. 30, 2015, 2 pages.
GenBank NCBI Reference Sequence: XP_011886513.1, "Predicted: tumor necrosis factor receptor superfamily member 4 isoform X2 [Cercocebus atys]," Mar. 30, 2015, 2 pages.
GenBank NCBI Reference Sequence: XP_011903009.1, "Predicted: inducible T- cell costimulator [Cercocebus atys]," Mar. 30, 2015, 2 pages.
GenBank NCBI Reference Sequence: XP_012301784.1, "inducible T-cell costimulator isoform X1 [Aotus nancymaae]," Jun. 28, 2017, 2 pages.
GenBank NCBI Reference Sequence: XP_012301785.1, "inducible T-cell costimulator isoform X2 [Aotus nancymaae]," Jun. 28, 2017, 2 pages.
GenBank NCBI Reference Sequence: XP_012865504.1, "Predicted: T-cell-specific surface glycoprotein CD28 [Dipodomys ordii]," Jun. 26, 2015, 3 pages.
GenBank NCBI Reference Sequence: XP_012867363.1, "Predicted: inducible T- cell costimulator isoform X1 [Dipodomys ordii], " Jun. 26, 2015, 2 pages.
GenBank NCBI Reference Sequence: XP_012867370.1, "Predicted: inducible T- cell costimulator isoform X2 [Dipodomys ordii]," Jun. 26, 2015, 2 pages.
GenBank NCBI Reference Sequence: XP_012888584.1, "Predicted: tumor necrosis factor receptor superfamily member 9 [Dipodomys ordii]," Jun. 26, 2015, 2 pages.

(56) References Cited

OTHER PUBLICATIONS

GenBank NCBI Reference Sequence: XP_012929934.1, "inducible T-cell costimulator isoform X2 [Heterocephalus glaber]," May 23, 2017, 2 pages.
GenBank NCBI Reference Sequence: XP_014966207.1, "T-cell-specific surface glycoprotein CD28 isoform X1 [Macaca mulatta]," Apr. 26, 2019, 2 pages.
GenBank NCBI Reference Sequence: XP_016857720.1, "tumor necrosis factor receptor superfamily member 4 isoform X2 [*Homo sapiens*]," Nov. 22, 2021, 2 pages.
GenBank NCBI Reference Sequence: XP_016857721.1, "tumor necrosis factor receptor superfamily member 4 isoform X4 [*Homo sapiens*]," Nov. 22, 2021, 2 pages.
GenBank NCBI Reference Sequence: XP_016881773.1, "transmembrane and immunoglobulin domain-containing protein 2 isoform X1 [*Homo sapiens*]," Nov. 22, 2021, 2 pages.
GenBank NCBI Reference Sequence: XP_017392362.1, "inducible T-cell costimulator [Cebus imitator]," Nov. 20, 2020, 2 pages.
GenBank NCBI Reference Sequence: XP_017457364.1, "Icos ligand isoform X4 [Rattus norvegicus]," Jan. 21, 2021, 2 pages.
GenBank NCBI Reference Sequence: XP_017739861.1, "Predicted: inducible T- cell costimulator [Rhinopithecus bieti]," Aug. 24, 2016, 2 pages.
GenBank NCBI Reference Sequence: XP_017750744.1, "Predicted: tumor necrosis factor receptor superfamily member 4 [Rhinopithecus bieti], " Aug. 24, 2016, 2 pages.
GenBank NCBI Reference Sequence: XP_017802331.1, "inducible T-cell costimulator isoform X3 [Papio anubis]," Nov. 20, 2019, 1 page.
GenBank NCBI Reference Sequence: XP_019061859.2, "T-cell-specific surface glycoprotein CD28 [Fukomys damarensis]," Apr. 23, 2020, 3 pages.
GenBank NCBI Reference Sequence: XP_021017102.2, "tumor necrosis factor receptor superfamily member 4 [Mus caroli]," Jun. 10, 2019, 2 pages.
GenBank NCBI Reference Sequence: XP_021027481.1, "T-cell-specific surface glycoprotein CD28 [Mus caroli], " Jun. 10, 2019, 3 pages.
GenBank NCBI Reference Sequence: XP_021030282.1, "inducible T-cell costimulator [Mus caroli]," Jun. 10, 2019, 2 pages.
GenBank NCBI Reference Sequence: XP_021052880.1, "inducible T-cell costimulator [Mus pahari]," Jun. 18, 2019, 2 pages.
GenBank NCBI Reference Sequence: XP_021054806.1, "T-cell-specific surface glycoprotein CD28 [Mus pahari]," Jun. 18, 2019, 3 pages.
GenBank NCBI Reference Sequence: XP_021056714.1, "tumor necrosis factor receptor superfamily member 4 [Mus pahari]," Jun. 18, 2019, 2 pages.
GenBank NCBI Reference Sequence: XP_021099219.1, "tumor necrosis factor receptor superfamily member 9 [Heterocephalus glaber]," May 23, 2017, 2 pages.
GenBank NCBI Reference Sequence: XP_021119236.1, "inducible T-cell costimulator isoform X1 [Heterocephalus glaber]," May 23, 2017, 2 pages.
GenBank NCBI Reference Sequence: XP_021523144.1, "Low Quality Protein: tumor necrosis factor receptor superfamily member 4 [Aotus nancymaae]," Jun. 28, 2017, 2 pages.
GenBank NCBI Reference Sequence: XP_021779593.1, "inducible T-cell costimulator isoform X1 [Papio anubis]," Nov. 20, 2019, 2 pages.
GenBank NCBI Reference Sequence: XP_023075099.1, "inducible T-cell costimulator isoform X1 [Piliocolobus tephrosceles]," Dec. 30, 2019, 2 pages.
GenBank NCBI Reference Sequence: XP_023075107.1, "inducible T-cell costimulator isoform X2 [Piliocolobus tephrosceles]," Dec. 30, 2019, 2 pages.
GenBank NCBI Reference Sequence: XP_024307127.1, "transmembrane and immunoglobulin domain-containing protein 2 isoform X2 [*Homo sapiens*]," May 16, 2021, 2 pages.
GenBank NCBI Reference Sequence: XP_025242473.1, "tumor necrosis factor receptor superfamily member 4 [Theropithecus gelada]," Jun. 29, 2018, 2 pages.
GenBank NCBI Reference Sequence: XP_025260986.1, "inducible T-cell costimulator isoform X1 [Theropithecus gelada]," Jun. 29, 2018, 2 pages.
GenBank NCBI Reference Sequence: XP_025260987.1, "inducible T-cell costimulator isoform X2 [Theropithecus gelada]," Jun. 29, 2018, 2 pages.
GenBank NCBI Reference Sequence: XP_025260988.1, "inducible T-cell costimulator isoform X3 [Theropithecus gelada]," Jun. 29, 2018, 2 pages.
GenBank NCBI Reference Sequence: XP_026313228.1, "tumor necrosis factor receptor superfamily member 4 isoform X1 [Piliocolobus tephrosceles]," Dec. 30, 2019, 2 pages.
GenBank NCBI Reference Sequence: XP_026313229.1, "tumor necrosis factor receptor superfamily member 4 isoform X2 [Piliocolobus tephrosceles]," Dec. 30, 2019, 2 pages.
GenBank NCBI Reference Sequence: XP_029334968.1, "inducible T-cell costimulator [Mus caroli]," Jun. 10, 2019, 2 pages.
GenBank NCBI Reference Sequence: XP_029414154.1, "tumor necrosis factor receptor superfamily member 9 isoform X1 [Nannospalax galili]," Jun. 24, 2019, 2 pages.
GenBank NCBI Reference Sequence: XP_029414155.1, "tumor necrosis factor receptor superfamily member 9 isoform X1 [Nannospalax galili]," Jun. 24, 2019, 2 pages.
GenBank NCBI Reference Sequence: XP_029425757.1, "inducible T-cell costimulator [Nannospalax galili]," Jun. 24, 2019, 2 pages.
GenBank NCBI Reference Sequence: XP_030104805.1, "T-lymphocyte activation antigen CD80 isoform X2 [Mus musculus]," Sep. 21, 2020, 3 pages.
GenBank NCBI Reference Sequence: XP_032134413.1, "inducible T-cell costimulator isoform X1 [Sapajus apella]," Feb. 2, 2020, 2 pages.
GenBank NCBI Reference Sequence: XP_032134414.1, "inducible T-cell costimulator isoform X2 [Sapajus apella]," Feb. 2, 2020, 2 pages.
GenBank NCBI Reference Sequence: XP_032755445.1, "T-cell-specific surface glycoprotein CD28 [Rattus rattus]," Mar. 14, 2020, 3 pages.
GenBank NCBI Reference Sequence: XP_032755449.1, "inducible T-cell costimulator [Rattus rattus]," Mar. 14, 2020, 2 pages.
GenBank NCBI Reference Sequence: XP_033086489.1, "inducible T-cell costimulator [Trachypithecus francoisi]," Mar. 28, 2020, 2 pages.
GenBank NCBI Reference Sequence: XP_034354910.1, "T-cell-specific surface glycoprotein CD28 [Arvicanthis niloticus]," May 16, 2020, 3 pages.
GenBank NCBI Reference Sequence: XP_036012281.1, "T-cell-specific surface glycoprotein CD28 isoform X1 [Mus musculus]," Sep. 21, 2020, 3 pages.
GenBank NCBI Reference Sequence: XP_036015651.1, "T-lymphocyte activation antigen CD80 isoform X1 [Mus musculus]," Sep. 21, 2020, 2 pages.
GenBank NCBI Reference Sequence: XP_038940099.1, "inducible T-cell costimulator isoform X3 [Rattus norvegicus]," Jan. 21, 2021, 2 pages.
Gongbo Li et al., "4-1BB enhancement of CAR T function requires NF-κB and TRAFs," JCI Insight, Sep. 20, 2018, 3(18):e121322, 19 pages.
Guedan, et al., "Engineering and Design of Chimeric Antigen Receptors." Mol Ther Methods Clin Dev. Dec. 31, 2018, 12:145-156.
Guedan, et al., "Enhancing CAR T cell persistence through ICOS and 4-1BB costimulation." JCI Insight. Jan. 11, 2018, 3(1):e96976, 18 pages.
Guo, R et al. "Targeting BCMA to Treat Multiple Myeloma: Updates From the 2021 ASH Annual Meeting," Front Immunol., Mar. 7, 2022, 13:839097, 19 pages.
Hoogi S., et al., "A TIGIT-based chimeric co-stimulatory switch receptor improves T-cell anti-tumor function." J Immunother Cancer., Sep. 9, 2019, 7(1):243, 13 pages.

(56) References Cited

OTHER PUBLICATIONS

International Search Report and Written Opinion issued in PCT/US2022/011103 dated Apr. 28, 2022, 1-10.
June, C.H., et al., "CAR T cell immunotherapy for human cancer." Science, Mar. 23, 2018, 359(6382):1361-1365.
Klippel, Z.K., et al., "Immune escape from NY-ESO-1-specific T-cell therapy via loss of heterozygosity in the MHC." Gene Ther. Mar. 2014, 21(3):337-342. Epub Jan. 23, 2014 (14 pages total).
Kobold, S., et al., Impact of a New Fusion Receptor on PD-1-Mediated Immunosuppression in Adoptive T Cell Therapy. J Natl Cancer Inst. Jun. 23, 2015, 107(8):djv146, 10 pages.
Lee, L. et al. "Evaluation of B cell maturation antigen as a target for antibody drug conjugate mediated cytotoxicity in multiple myeloma," Br. J. Haematol, 2016, 174:911-922.
Li, Y., et al. "Directed evolution of human T-cell receptors with picomolar affinities by phage display." Nature Biotechnology, Mar. 2005, 23(3):349-354.
Liu, X. et al. "A Chimeric Switch-Receptor Targeting PD1 Augments the Efficacy of Second-Generation CAR T Cells in Advanced Solid Tumors," Cancer Res. Mar. 15, 2016, 76(6):1578-1590.
Mackall, C., et al., "Autologous genetically engineered NY-ESO-$1^{c259}$T in HLA-A*02:01, HLA*02:05 and HLA*02:06 positive patients with NY-ESO-1 expressing tumors." Journal Clin Oncol., 2016, 34(15), 1 page.
Mackay, M., et al., "The therapeutic landscape for cells engineered with chimeric antigen receptors." Nat Biotechnol., 2020, 38(2):233-244, including Methods and Reporting Summary (16 total pages).
Moon, E.K., et al., "Blockade of Programmed Death 1 Augments the Ability of Human T Cells Engineered to Target NY-ESO-1 to Control Tumor Growth after Adoptive Transfer." Clin Cancer Res., Jan. 15, 2016, 22(2):436-447.
O'donnell, U.S., et al., "Cancer immunoediting and resistance to T cell-based immunotherapy." Nat Rev Clin Oncol., Mar. 2019, 16(3):151-167.
Parmar H.B., et al., "Polybasic Trafficking Signal Mediates Golgi Export, ER Retention or ER Export and Retrieval Based on Membrane-Proximity." PLoS One. Apr. 2014, 9(4):e94194, 10 pages.
Rapoport, A. P. et al., "NY-ESO-1-specific TCR-engineered T cells mediate sustained antigen-specific antitumor effects in myeloma," Nature Medicine, Aug. 2015, 21(8):914-921 (including online methods, 10 total pages).
Raza, A., et al., "Unleashing the immune response to NY-ESO-1 cancer testis antigen as a potential target for cancer immunotherapy." J Transl Med., Mar. 27, 2020, 18(1):140, 11 pages.
Robbins, P. F. et al., "A Pilot Trial Using Lymphocytes Genetically Engineered with an NY-ESO-1-Reactive T-cell Receptor: Long-term Follow-up and Correlates with Response," Clin Cancer Res, Mar. 2015, 21(5):1019-1027.
UniProtKB/Swiss-Prot No. P10747.1, "RecName: Full=T-cell-specific surface glycoprotein CD28; AltName: Full=TP44; AltName: CD_antigen=CD28; Flags: Precursor," May 25, 2022, 9 pages.
UniProtKB/Swiss-Prot No. P15725.1, "RecName: Full=Tumor necrosis factor receptor superfamily member 4; AltName: Full=MRC OX40; AltName: Full=OX40 antigen; AltName: Full=OX40L receptor; AltName: CD_antigen=CD134; Flags: Precursor," May 25, 2022, 3 pages.
UniProtKB/Swiss-Prot No. P20334-1, "TNR9_MOUSE," downloaded from web at https://glygen.org/protein/P20334, only Jul. 13, 2022, 8 pages.
UniProtKB/Swiss-Prot No. P31041.2, "RecName: Full=T-cell-specific surface glycoprotein CD28; AltName: CD_antigen=CD28; Flags: Precursor," May 25, 2022, 5 pages.
UniProtKB/Swiss-Prot No. P31042.1, " RecName: Full=T-cell-specific surface glycoprotein CD28; AltName: CD_antigen=CD28; Flags: Precursor," May 25, 2022, 4 pages.
UniProtKB/Swiss-Prot No. P43489.1, "RecName: Full=Tumor necrosis factor receptor superfamily member 4; AltName: Full=ACT35 antigen; AltName: Full=OX40L receptor; AltName: Full=TAX transcriptionally-activated glycoprotein 1 receptor; AltName: CD_antigen=CD134; Flags: Precursor," May 25, 2022, 6 pages.
UniProtKB/Swiss-Prot No. P47741.1, " RecName: Full=Tumor necrosis factor receptor superfamily member 4; AltName: Full=OX40 antigen; AltName: Full=OX40L receptor; AltName: CD_antigen=CD134; Flags: Precursor," May 25, 2022, 3 pages.
UniProtKB/Swiss-Prot No. Q07011, "TNR9_HUMAN," downloaded from web at https://www.uniprot.org/uniprotkb/Q07011/ entry, on Jul. 13, 2022, 8 pages.
UniProtKB/Swiss-Prot No. Q96BF3.2, "RecName: Full= Transmembrane and immunoglobulin domain-containing protein 2; AltName: Full=CD28 homolog; AltName: Full=Immunoglobulin and proline-rich receptor 1; Short=IGPR-1; Flags: Precursor," May 25, 2022, 5 pages.
UniProtKB/Swiss-Prot No. Q9R1T7.1, "RecName: Full=Inducible T-cell costimulator; AltName: Full=Activation-inducible lymphocyte immunomediatory molecule; AltName: CD_antigen=CD278; Flags: Precursor," May 25, 2022, 3 pages.
UniProtKB/Swiss-Prot No. Q9WVS0.2, "RecName: Full=Inducible T-cell costimulator; AltName: Full=Activation-inducible lymphocyte immunomediatory molecule; AltName: Full=CD28 and CTLA-4-like protein; Short=CCLP; AltName: Full=CD28-related protein 1; Short=CRP-1; AltName: CD_antigen=CD278; Flags: Precursor," May 25, 2022, 4 pages.
UniProtKB/Swiss-Prot No. Q9Y6W8.1, "RecName: Full=Inducible T-cell costimulator; AltName: Full=Activation-inducible lymphocyte immunomediatory molecule; AltName: CD_antigen=CD278; Flags: Precursor," May 25, 2022, 5 pages.
Wang, X et al. "A transgene-encoded cell surface polypeptide for selection, in vivo tracking, and ablation of engineered cells" Blood, Aug. 4, 2011, 118(5):1255-1263.
Zhao, Y., et al., "High-Affinity TCRs Generated by Phage Display Provide CD4+ T Cells with the Ability to Recognize and Kill Tumor Cell Lines." J Immunol., 2007, 179(9):5845-5854.
Zhao, Z. et al., "Structural design of engineered costimulation determines tumor rejection kinetics and persistence of CAR T cells," Cancer cell, Oct. 12, 2015, 28(4):415-428 (27 pages total).
Zhong X-S., et al., "Chimeric Antigen Receptors Combining 4-1BB and CD28 Signaling Domains Augment Plskinase/AKT/Bcl-$X_L$ Activation and CD8+ T Cell-mediated Tumor Eradication," Molecular Therapy, Feb. 2010, 18(2):413-420.
Feucht, J. et al. "Calibration of CAR activation potential directs alternative T cell fates and therapeutic potency," Nature Medicine, Jan. 2019, 25:82-88 (28 pages total).
International Search Report and Written Opinion for PCT Application No. PCT/US2023/069612 dated Oct. 23, 2023, 21 pages.
Li et al., "4-1BB enhancement of CAR T function requires NF-κB and TRAFs", JCI Insight., Sep. 20, 2018, 3(18):e121322, 43 pages.
Macleod et al., "Integration of a CD19 CAR into the TCR Alpha Chain Locus Streamlines Production of Allogeneic Gene-Edited CAR T Cells", Molecular Therapy, 2017, 25(4):949-961 (24 pages total).
Fujiwara et al., "Structure of the Signal Transduction Domain in Second-Generation CAR Regulates the Input Efficiency of CAR Signals," Int. J. Mol. Sci. 2021, 22, 2476, p. 1-20 and supplementary p. 1-9. Published Mar. 1, 2021.
Li et al., "Chimeric Antigen Receptor Designed to Prevent Ubiquitination and Downregulation Showed Durable Antitumor Efficacy," Immunity, 2020; 53: 456-470, el-e6, supplemental p. 23-36.
UniProtKB—P20963 (CD3Z_HUMAN). T-cell surface glycoprotein CD3 zeta chain; 12 pages; retrieved on May 13, 2016 from http://www.uniprot.org/uniproUP2.

* cited by examiner

SP: signal peptide
BCMA: BCMA-binding nanobody
H: hinge
S: stalk
TM: transmembrane
ICOS: ICOS
4-1BBt: 4-1BB with N-terminal truncation
CD3ζt: CD3ζ with C-terminal truncation of ITAM2 and ITAM3

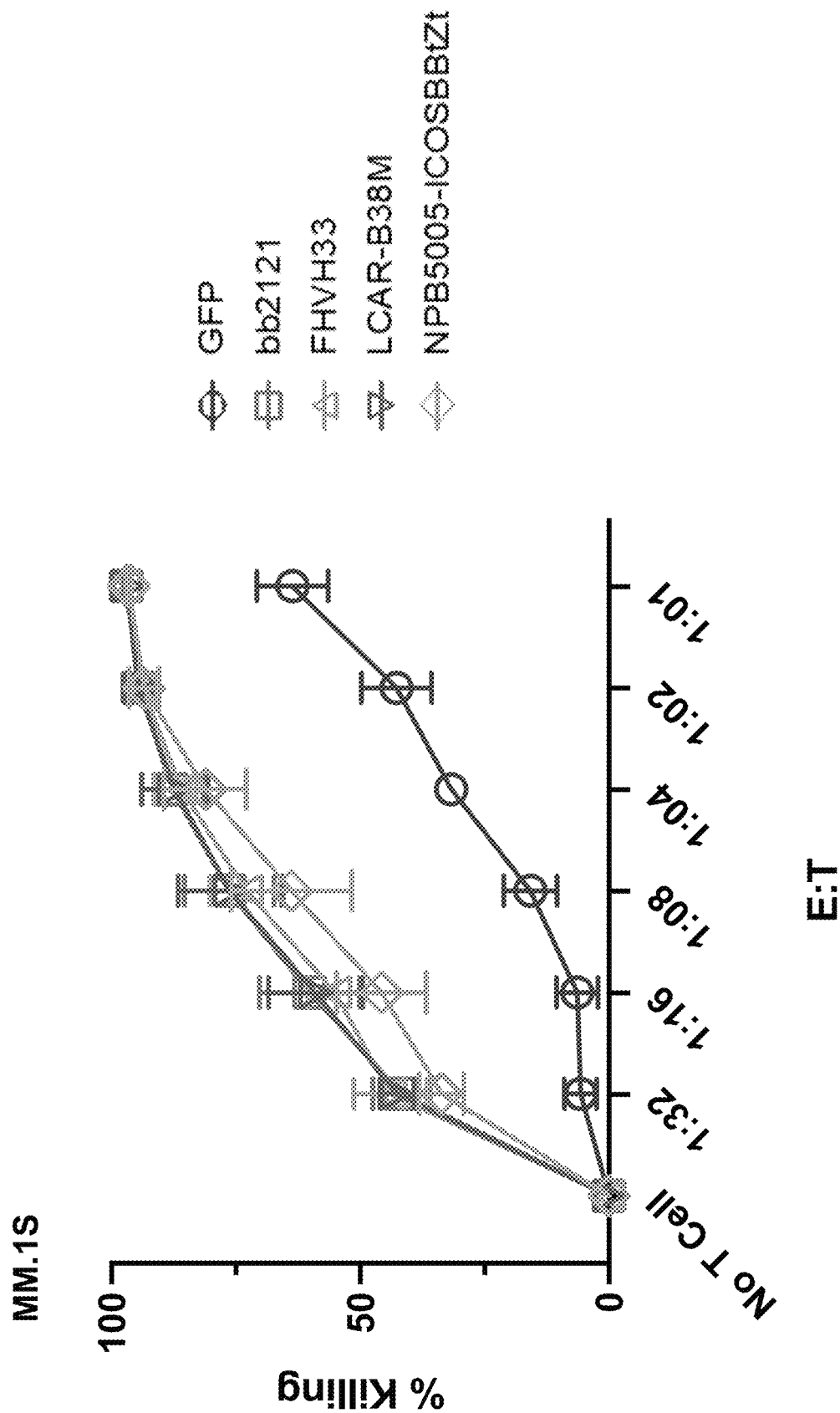

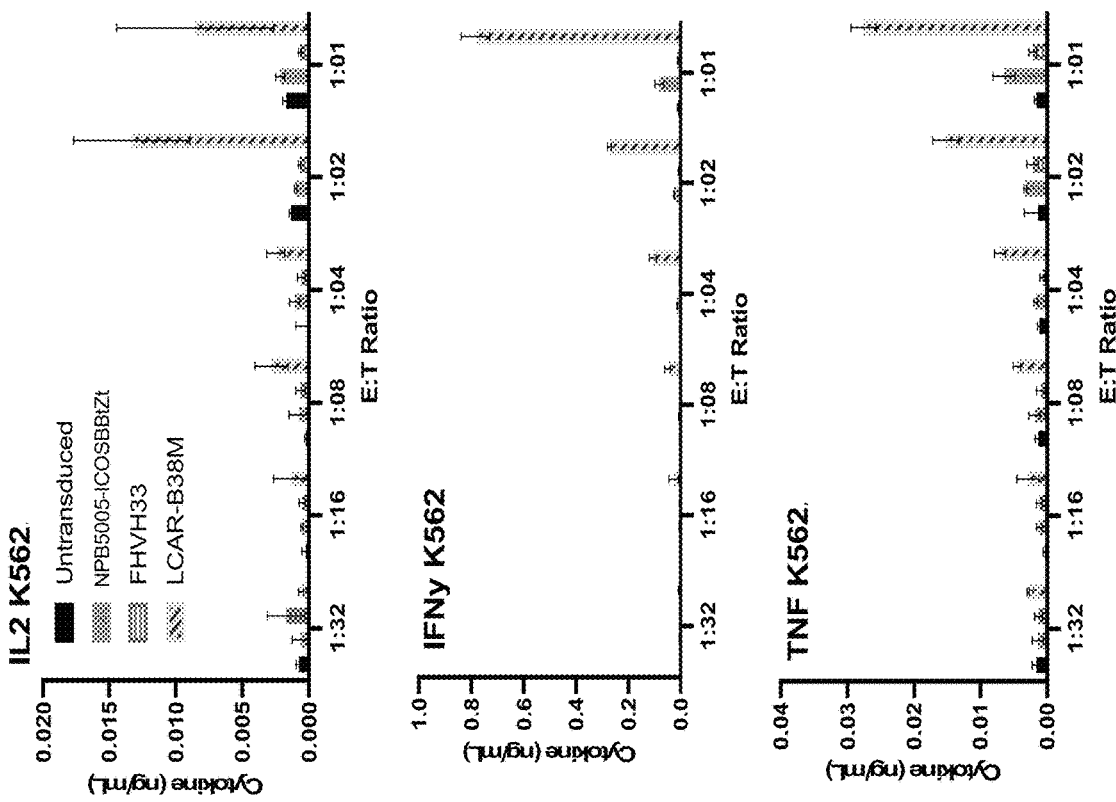

SEQUENCE LISTING

```
Sequence total quantity: 33
SEQ ID NO: 1            moltype = AA  length = 193
FEATURE                 Location/Qualifiers
source                  1..193
                        mol_type = protein
                        organism = synthetic construct
SEQUENCE: 1
MALPVTALLL PLALLLHAAR PEVQLQASGG GLAQPGGSLR LSCAASGRTF STYFMAWFRQ   60
PPGKGLEYVG GIRWSDGVPH YADSVKGRFT ISRDNAKNTV YLQMNSLRAE DTAVYFCASR  120
GIADGSDFGS YGQGTQVTVS STTTPAPRPP TPAPTIASQP LSLRPEACRP AAGGAVHTRG  180
LDFACSQLCC QLK                                                    193

SEQ ID NO: 2            moltype = AA  length = 38
```

```
FEATURE                 Location/Qualifiers
source                  1..38
                        mol_type = protein
                        organism = synthetic construct
SEQUENCE: 2
CWLTKKKYSS SVHDPNGEYM FMRAVNTAKK SRLTDVTL                              38

SEQ ID NO: 3            moltype = AA   length = 30
FEATURE                 Location/Qualifiers
source                  1..30
                        mol_type = protein
                        organism = synthetic construct
SEQUENCE: 3
QPFMRPVQTT QEEDGCSCRF PEEEEGGCEL                                       30

SEQ ID NO: 4            moltype = AA   length = 48
FEATURE                 Location/Qualifiers
source                  1..48
                        mol_type = protein
                        organism = synthetic construct
SEQUENCE: 4
RVKFSRSADA PAYQQGQNQL YNELNLGRRE EYDVLDKRRG RDPEMGGK                   48

SEQ ID NO: 5            moltype = AA   length = 330
FEATURE                 Location/Qualifiers
source                  1..330
                        mol_type = protein
                        organism = synthetic construct
SEQUENCE: 5
MALPVTALLL PLALLLHAAR PEVQLQASGG GLAQPGGSLR LSCAASGRTF STYFMAWFRQ      60
PPGKGLEYVG GIRWSDGVPH YADSVKGRFT ISRDNAKNTV YLQMNSLRAE DTAVYFCASR     120
GIADGSDFGS YGQGTQVTVS STTTPAPRPP TPAPTIASQP LSLRPEACRP AAGGAVHTRG     180
LDFACSQLCC QLKFWLPIGC AAFVVVCILG CILICWLTKK KYSSSVHDPN GEYMFMRAVN     240
TAKKSRLTDV TLQPFMRPVQ TTQEEDGCSC RFPEEEEGGC ELRVKFSRSA DAPAYQQGQN     300
QLYNELNLGR REEYDVLDKR RGRDPEMGGK                                      330

SEQ ID NO: 6            moltype = AA   length = 21
FEATURE                 Location/Qualifiers
source                  1..21
                        mol_type = protein
                        organism = synthetic construct
SEQUENCE: 6
MALPVTALLL PLALLLHAAR P                                                21

SEQ ID NO: 7            moltype = AA   length = 44
FEATURE                 Location/Qualifiers
source                  1..44
                        mol_type = protein
                        organism = synthetic construct
SEQUENCE: 7
TTTPAPRPPT PAPTIASQPL SLRPEACRPA AGGAVHTRGL DFAC                       44

SEQ ID NO: 8            moltype = AA   length = 120
FEATURE                 Location/Qualifiers
source                  1..120
                        mol_type = protein
                        organism = synthetic construct
SEQUENCE: 8
EVQLQASGGG LAQPGGSLRL SCAASGRTFS TYFMAWFRQP PGKGLEYVGG IRWSDGVPHY      60
ADSVKGRFTI SRDNAKNTVY LQMNSLRAED TAVYFCASRG IADGSDFGSY GQGTQVTVSS     120

SEQ ID NO: 9            moltype = AA   length = 8
FEATURE                 Location/Qualifiers
source                  1..8
                        mol_type = protein
                        organism = synthetic construct
SEQUENCE: 9
SQLCCQLK                                                                8

SEQ ID NO: 10           moltype = AA   length = 21
FEATURE                 Location/Qualifiers
source                  1..21
                        mol_type = protein
                        organism = synthetic construct
SEQUENCE: 10
FWLPIGCAAF VVVCILGCIL I                                                21

SEQ ID NO: 11           moltype = DNA   length = 993
FEATURE                 Location/Qualifiers
```

```
source                  1..993
                        mol_type = other DNA
                        organism = synthetic construct
SEQUENCE: 11
atggctctgc ctgtgacagc tctgctgctg cctctggctc tgcttctgca tgccgctaga    60
cctgaagtgc agttcaggc ttctggcgga ggacttgctc aacctggcgg aagcctgaga   120
ctgtcttgtg ccgcctctgg cagaaccttc agcaccctact tcatggcctg gttcagacag   180
cctcctggca aggcctgga atacgttggc ggaatccgtt ggagtgatgg cgtgccacac   240
tacgccgata gcgtgaaggg cagattcacc atcagccggg acaacgccaa gaacaccgtg   300
tacctccaga tgaacagcct gagagccgag gataccgtgt acttcttgt gctgcagcag   360
ggaatcgccg acggcagcga ttttggctct tatggccagg caccaagt gaccgtgtcc   420
agcacaacaa cccctgctcc tagacctcct acaccagctc ctacaatcgc cagccagcct   480
ctgtctctga ggccagaggc ttgtagacct gctgctggcg gagccgtgca tacaagagga   540
ctggatttcg cctgcagcca gctgtgctgt cagctgaagt tctggctgcc tatcggctgc   600
gccgcctttg tggttgtgtg tatcctgggc tgcatcctga tctgctggct gaccaagaaa   660
aagtacagca gcagcgtgca cgaccccaac ggcgagtaca tgttcatgag agccgtgaac   720
accgccaaga agtccagact gaccgacgtg accctcagc ctttcatgag gcctgtgcag   780
accacacaag aagaggacgg ctgctcctgt cggttcccg aggaagaga aggcggttgc   840
gagctgagag tgaagttcag cagatccgcc gacgctcctg cctatcagca gggccaaac   900
cagctgtaca cgagctgaa cctggggaga agaagagt acgacgtgct ggacaagcgg   960
agaggcgaga tcctgaaat gggcggcaaa tga                                993

SEQ ID NO: 12            moltype = AA  length = 374
FEATURE                  Location/Qualifiers
source                   1..374
                         mol_type = protein
                         organism = synthetic construct
SEQUENCE: 12
MALPVTALLL PLALLLHAAR PEVQLQASGG GLAQPGGSLR LSCAASGRTF STYFMAWFRQ    60
PPGKGLEYVG GIRWSDGVPH YADSVKGRFT ISRDNAKNTV YLQMNSLRAE DTAVYFCASR   120
GIADGSDFGS YGQGTQVTVS STTTPAPRPP TPAPTIASQP LSLRPEACRP AAGGAVHTRG   180
LDFACLFPGP SKPFWVLVVV GGVLACYSLL VTVAFIIFWV RSKRSRLLHS DYMNMTPRRP   240
GPTRKHYQPY APPRDFAAYR SRVKFSRSAD APAYQQGQNQ LYNELNLGRR EEYDVLDKRR   300
GRDPEMGGKP QRRKNPQEGL YNELQKDKMA EAYSEIGMKG ERRRGKGHDG LYQGLSTATK   360
DTYDALHMQA LPPR                                                    374

SEQ ID NO: 13            moltype = AA  length = 365
FEATURE                  Location/Qualifiers
source                   1..365
                         mol_type = protein
                         organism = synthetic construct
SEQUENCE: 13
MALPVTALLL PLALLLHAAR PEVQLQASGG GLAQPGGSLR LSCAASGRTF STYFMAWFRQ    60
PPGKGLEYVG GIRWSDGVPH YADSVKGRFT ISRDNAKNTV YLQMNSLRAE DTAVYFCASR   120
GIADGSDFGS YGQGTQVTVS STTTPAPRPP TPAPTIASQP LSLRPEACRP AAGGAVHTRG   180
LDFACDIYIW APLAGTCGVL LLSLVITLYC KRGRKKLLYI FKQPFMRPVQ TTQEEDGCSC   240
RFPEEEEGGC ELRVKFSRSA DAPAYQQGQN QLYNELNLGR REEYDVLDKR RGRDPEMGGK   300
PQRRKNPQEG LYNELQKDKM AEAYSEIGMK GERRRGKGHD GLYQGLSTAT KDTYDALHMQ   360
ALPPR                                                              365

SEQ ID NO: 14            moltype = AA  length = 407
FEATURE                  Location/Qualifiers
source                   1..407
                         mol_type = protein
                         organism = synthetic construct
SEQUENCE: 14
MALPVTALLL PLALLLHAAR PEVQLQASGG GLAQPGGSLR LSCAASGRTF STYFMAWFRQ    60
PPGKGLEYVG GIRWSDGVPH YADSVKGRFT ISRDNAKNTV YLQMNSLRAE DTAVYFCASR   120
GIADGSDFGS YGQGTQVTVS STTTPAPRPP TPAPTIASQP LSLRPEACRP AAGGAVHTRG   180
LDFACSQLCC QLKFWLPIGC AAFVVVCILG CILICWLTKK KYSSSVHDPN GEYMFMRAVN   240
TAKKSRLTDV TLKRGRKKLL YIFKQPFMRP VQTTQEEDGC SCRFPEEEEG GCELRVKFSR   300
SADAPAYQQG QNQLYNELNL GRREEYDVLD KRRGRDPEMG GKPQRRKNPQ EGLYNELQKD   360
KMAEAYSEIG MKGERRRGKG HDGLYQGLST ATKDTYDALH MQALPPR                407

SEQ ID NO: 15            moltype = AA  length = 395
FEATURE                  Location/Qualifiers
source                   1..395
                         mol_type = protein
                         organism = synthetic construct
SEQUENCE: 15
MALPVTALLL PLALLLHAAR PEVQLQASGG GLAQPGGSLR LSCAASGRTF STYFMAWFRQ    60
PPGKGLEYVG GIRWSDGVPH YADSVKGRFT ISRDNAKNTV YLQMNSLRAE DTAVYFCASR   120
GIADGSDFGS YGQGTQVTVS STTTPAPRPP TPAPTIASQP LSLRPEACRP AAGGAVHTRG   180
LDFACSQLCC QLKFWLPIGC AAFVVVCILG CILICWLTKK KYSSSVHDPN GEYMFMRAVN   240
TAKKSRLTDV TLQPFMRPVQ TTQEEDGCSC RFPEEEEGGC ELRVKFSRSA DAPAYQQGQN   300
QLYNELNLGR REEYDVLDKR RGRDPEMGGK PQRRKNPQEG LYNELQKDKM AEAYSEIGMK   360
GERRRGKGHD GLYQGLSTAT KDTYDALHMQ ALPPR                              395

SEQ ID NO: 16            moltype = AA  length = 22
```

| FEATURE | Location/Qualifiers |
|---|---|
| source | 1..22<br>mol_type = protein<br>organism = synthetic construct |

SEQUENCE: 16
```
GSGATNFSLL KQAGDVEENP GP                                            22
```

| SEQ ID NO: 17 | moltype = AA   length = 357 |
|---|---|
| FEATURE | Location/Qualifiers |
| source | 1..357<br>mol_type = protein<br>organism = synthetic construct |

SEQUENCE: 17
```
MLLLVTSLLL CELPHPAFLL IPRKVCNGIG IGEFKDSLSI NATNIKHFKN CTSISGDLHI    60
LPVAFRGDSF THTPPLDPQE LDILKTVKEI TGFLLIQAWP ENRTDLHAFE NLEIIRGRTK   120
QHGQFSLAVV SLNITSLGLR SLKEISDGDV IISGNKNLCY ANTINWKKLF GTSGQKTKII   180
SNRGENSCKA TGQVCHALCS PEGCWGPEPR DCVSCRNVSR GRECVDKCNL LEGEPREFVE   240
NSECIQCHPE CLPQAMNITC TGRGPDNCIQ CAHYIDGPHC VKTCPAGVMG ENNTLVWKYA   300
DAGHVCHLCH PNCTYGCTGP GLEGCPTNGP KIPSIATGMV GALLLLLVVA LGIGLFM     357
```

| SEQ ID NO: 18 | moltype = DNA   length = 66 |
|---|---|
| FEATURE | Location/Qualifiers |
| source | 1..66<br>mol_type = other DNA<br>organism = synthetic construct |

SEQUENCE: 18
```
ggatccggcg ccaccaattt cagcctgctg aaacaggctg gcgacgtgga agagaaccct    60
ggacct                                                              66
```

| SEQ ID NO: 19 | moltype = DNA   length = 1074 |
|---|---|
| FEATURE | Location/Qualifiers |
| source | 1..1074<br>mol_type = other DNA<br>organism = synthetic construct |

SEQUENCE: 19
```
atgctgctgc tggttacatc tctgctgctg tgcgagctgc cccatcctgc ctttctgctg    60
atccccagaa aagtgtgcaa cggcatcggc atcggagagt tcaaggacag cctgagcatc   120
aacgccacca acatcaagca cttcaagaac tgcaccagca tcagcggcga cctgcacatt   180
ctgcctgtgg cctttagagg cgacagcttc acccacacae ctccactgga ccctcaagag   240
ctggacatcc tgaaaaccgt gaaagagatc accggatttc tgttgatcca ggcttggccc   300
gagaaccgga cagatctgca cgccttcgag aacctggaaa tcatcagagg ccggaccaag   360
cagcacggcc agttttctct ggctgtggtg tccctgaaca tcaccagcct gggcctgaga   420
agcctgaaag aaatcagcga cggcgacgtg atcatctccg gcaacaagaa cctgtgctac   480
gccaacacca tcaactggaa gaagctgttc ggcaccagcg gccagaaaac aaagatcatc   540
agcaaccggg gcgagaacag ctgcaaggct acaggccaag tgtgccacgc tctgtgtagc   600
cctgaaggct gttggggacc cgagcctaga gattgcgtgt cctgtcggaa ctgtgtcccg   660
ggcagagaat gcgtggacaa atgcaatctg ctggaaggcg agccccgcga gttcgtggaa   720
aacagcgagt gcatccagtg tcaccccgag tgtctgcccc aggccatgaa cattacctgt   780
accggcagag cccccgacaa ctgtattcag tgcgcccact acatcgacgg ccctcactgc   840
gtgaaaacat gtcctgctgg cgtgatggga gagaacaaca ccctcgtgtg gaagtatgcc   900
gacgccggac atgtgtgcca cctgtgtcac cctaattgca cctacggctg tacaggccct   960
ggcctggaag ctgtccaac aaacggacct aagatcccct ctatcgccac cggcatggtt  1020
ggagccctgc tgcttctgct ggtggtggcc cttggaatcg gcctgttcat gtga        1074
```

| SEQ ID NO: 20 | moltype = DNA   length = 72 |
|---|---|
| FEATURE | Location/Qualifiers |
| source | 1..72<br>mol_type = other DNA<br>organism = synthetic construct |

SEQUENCE: 20
```
atggctgtga tggcccctag aacactggtg ctgctgctgt ctggtgccct ggctctgact    60
cagacatggg cc                                                       72
```

| SEQ ID NO: 21 | moltype = DNA   length = 66 |
|---|---|
| FEATURE | Location/Qualifiers |
| source | 1..66<br>mol_type = other DNA<br>organism = synthetic construct |

SEQUENCE: 21
```
atgctgctgc tggttacatc tctgctgctg tgcgagctgc cccatcctgc ctttctgctg    60
atcccc                                                              66
```

| SEQ ID NO: 22 | moltype = AA   length = 380 |
|---|---|
| FEATURE | Location/Qualifiers |
| source | 1..380<br>mol_type = protein<br>organism = synthetic construct |

SEQUENCE: 22
```
MALPVTALLL PLALLLHAAR PEVQLLESGG GLVQPGGSLR LSCAASGFTF SSYAMSWVRQ    60
```

```
APGKGLEWVS SISGSGDYIY YADSVKGRFT ISRDISKNTL YLQMNSLRAE DTAVYYCAKE    120
GTGANSSLAD YRGQGTLVTV SSFVPVFLPA KPTTTPAPRP PTPAPTIASQ PLSLRPEACR    180
PAAGGAVHTR GLDFACDIYI WAPLAGTCGV LLLSLVITLY CNHRNKRGRK KLLYIFKQPF    240
MRPVQTTQEE DGCSCRFPEE EEGGCELRVK FSRSADAPAY QQGQNQLYNE LNLGRREEYD    300
VLDKRRGRDP EMGGKPQRRK NPQEGLYNEL QKDKMAEAYS EIGMKGERRR GKGHDGLYQG    360
LSTATKDTYD ALHMQALPPR                                                380

SEQ ID NO: 23          moltype = AA  length = 510
FEATURE                Location/Qualifiers
source                 1..510
                       mol_type = protein
                       organism = synthetic construct
SEQUENCE: 23
MALPVTALLL PLALLLHAAR PQVKLEESGG GLVQAGRSLR LSCAASEHTF SSHVMGWFRQ     60
APGKERESVA VIGWRDISTS YADSVKGRFT ISRDNAKKTL YLQMNSLKPE DTAVYYCAAR    120
RIDAADFDSW GQGTQVTVSS GGGGSGGGGS GGGGSGGGGS GGGGSAVQLV ESGGGLVQAG    180
DSLRLTCTAS GRAFSTYFMA WFRQAPGKER EFVAGIAWSG GSTAYADSVK GRFTISRDNS    240
KNTVYLQMNS LKSEDTAVYY CASRGIEVEE FGAWGQGTQV TVSSTSTTTP APRPPTPAPT    300
IASQPLSLRP EACRPAAGGA VHTRGLDFAC DIYIWAPLAG TCGVLLLSLV ITLYCKRGRK    360
KLLYIFKQPF MRPVQTTQEE DGCSCRFPEE EEGGCELRVK FSRSADAPAY QQGQNQLYNE    420
LNLGRREEYD VLDKRRGRDP EMGGKPQRRK NPQEGLYNEL QKDKMAEAYS EIGMKGERRR    480
GKGHDGLYQG LSTATKDTYD ALHMQALPPR                                     510

SEQ ID NO: 24          moltype = AA  length = 416
FEATURE                Location/Qualifiers
source                 1..416
                       mol_type = protein
                       organism = synthetic construct
SEQUENCE: 24
MALPVTALLL PLALLLHAAR PEVQLQASGG GLAQPGGSLR LSCAASGRTF STYFMAWFRQ     60
PPGKGLEYVG GIRWSDGVPH YADSVKGRFT ISRDNAKNTV YLQMNSLRAE DTAVYFCASR    120
GIADGSDFGS YGQGTQVTVS STTTPAPRPP TPAPTIASQP LSLRPEACRP AAGGAVHTRG    180
LDFACLFPGP SKPFWVLVVV GGVLACYSLL VTVAFIIFWV RSKRSRLLHS DYMNMTPRRP    240
GPTRKHYQPY APPRDFAAYR SKRGRKKLLY IFKQPFMRPV QTTQEEDGCS CRFPEEEEGG    300
CELRVKFSRS ADAPAYQQGQ NQLYNELNLG RREEYDVLDK RRGRDPEMGG KPQRRKNPQE    360
GLYNELQKDK MAEAYSEIGM KGERRRGKGH DGLYQGLSTA TKDTYDALHM QALPPR        416

SEQ ID NO: 25          moltype = AA  length = 404
FEATURE                Location/Qualifiers
source                 1..404
                       mol_type = protein
                       organism = synthetic construct
SEQUENCE: 25
MALPVTALLL PLALLLHAAR PEVQLQASGG GLAQPGGSLR LSCAASGRTF STYFMAWFRQ     60
PPGKGLEYVG GIRWSDGVPH YADSVKGRFT ISRDNAKNTV YLQMNSLRAE DTAVYFCASR    120
GIADGSDFGS YGQGTQVTVS STTTPAPRPP TPAPTIASQP LSLRPEACRP AAGGAVHTRG    180
LDFACLFPGP SKPFWVLVVV GGVLACYSLL VTVAFIIFWV RSKRSRLLHS DYMNMTPRRP    240
GPTRKHYQPY APPRDFAAYR SQPFMRPVQT TQEEDGCSCR FPEEEEGGCE LRVKFSRSAD    300
APAYQQGQNQ LYNELNLGRR EEYDVLDKRR GRDPEMGGKP QRRKNPQEGL YNELQKDKMA    360
EAYSEIGMKG ERRRGKGHDG LYQGLSTATK DTYDALHMQA LPPR                     404

SEQ ID NO: 26          moltype = AA  length = 395
FEATURE                Location/Qualifiers
source                 1..395
                       mol_type = protein
                       organism = synthetic construct
SEQUENCE: 26
MALPVTALLL PLALLLHAAR PEVQLQASGG GLAQPGGSLR LSCAASGRTF STYFMAWFRQ     60
PPGKGLEYVG GIRWSDGVPH YADSVKGRFT ISRDNAKNTV YLQMNSLRAE DTAVYFCASR    120
GIADGSDFGS YGQGTQVTVS STTTPAPRPP TPAPTIASQP LSLRPEACRP AAGGAVHTRG    180
LDFACLFPGP SKPFWVLVVV GGVLACYSLL VTVAFIIFWV RSKRSRLLHS DYMNMTPRRP    240
GPTRKHYQPY APPRDFAAYR SGGGSFRTPI QEEQADAHST LARVKFSRSA DAPAYQQGQN    300
QLYNELNLGR REEYDVLDKR RGRDPEMGGK PQRRKNPQEG LYNELQKDKM AEAYSEIGMK    360
GERRRGKGHD GLYQGLSTAT KDTYDALHMQ ALPPR                               395

SEQ ID NO: 27          moltype = AA  length = 365
FEATURE                Location/Qualifiers
source                 1..365
                       mol_type = protein
                       organism = synthetic construct
SEQUENCE: 27
MALPVTALLL PLALLLHAAR PEVQLQASGG GLAQPGGSLR LSCAASGRTF STYFMAWFRQ     60
PPGKGLEYVG GIRWSDGVPH YADSVKGRFT ISRDNAKNTV YLQMNSLRAE DTAVYFCASR    120
GIADGSDFGS YGQGTQVTVS STTTPAPRPP TPAPTIASQP LSLRPEACRP AAGGAVHTRG    180
LDFACSQLCC QLKFWLPIGC AAFVVVCILG CILICWLTKK KYSSSVHDPN GEYMFMRAVN    240
TAKKSRLTDV TLRVKFSRSA DAPAYQQGQN QLYNELNLGR REEYDVLDKR RGRDPEMGGK    300
PQRRKNPQEG LYNELQKDKM AEAYSEIGMK GERRRGKGHD GLYQGLSTAT KDTYDALHMQ    360
ALPPR                                                                365
```

```
SEQ ID NO: 28            moltype = AA  length = 386
FEATURE                  Location/Qualifiers
source                   1..386
                         mol_type = protein
                         organism = synthetic construct
SEQUENCE: 28
MALPVTALLL PLALLLHAAR PEVQLQASGG GLAQPGGSLR LSCAASGRTF STYFMAWFRQ    60
PPGKGLEYVG GIRWSDGVPH YADSVKGRFT ISRDNAKNTV YLQMNSLRAE DTAVYFCASR   120
GIADGSDFGS YGQGTQVTVS STTTPAPRPP TPAPTIASQP LSLRPEACRP AAGGAVHTRG   180
LDFACSQLCC QLKFWLPIGC AAFVVVCILG CILICWLTKK KYSSSVHDPN GEYMFMRAVN   240
TAKKSRLTDV TLGGGSFRTP IQEEQADAHS TLARVKFSRS ADAPAYQQGQ NQLYNELNLG   300
RREEYDVLDK RRGRDPEMGG KPQRRKNPQE GLYNELQKDK MAEAYSEIGM KGERRRGKGH   360
DGLYQGLSTA TKDTYDALHM QALPPR                                       386

SEQ ID NO: 29            moltype = AA  length = 309
FEATURE                  Location/Qualifiers
source                   1..309
                         mol_type = protein
                         organism = synthetic construct
SEQUENCE: 29
MALPVTALLL PLALLLHAAR PEVQLQASGG GLAQPGGSLR LSCAASGRTF STYFMAWFRQ    60
PPGKGLEYVG GIRWSDGVPH YADSVKGRFT ISRDNAKNTV YLQMNSLRAE DTAVYFCASR   120
GIADGSDFGS YGQGTQVTVS STTTPAPRPP TPAPTIASQP LSLRPEACRP AAGGAVHTRG   180
LDFACLPGP SKPFWVLVVV GGVLACYSLL VTVAFIIFWV RSKRSRLLHS DYMNMTPRRP   240
GPTRKHYQPY APPRDFAAYR SRVKFSRSAD APAYQQGQNQ LYNELNLGRR EEYDVLDKRR   300
GRDPEMGGK                                                          309

SEQ ID NO: 30            moltype = AA  length = 300
FEATURE                  Location/Qualifiers
source                   1..300
                         mol_type = protein
                         organism = synthetic construct
SEQUENCE: 30
MALPVTALLL PLALLLHAAR PEVQLQASGG GLAQPGGSLR LSCAASGRTF STYFMAWFRQ    60
PPGKGLEYVG GIRWSDGVPH YADSVKGRFT ISRDNAKNTV YLQMNSLRAE DTAVYFCASR   120
GIADGSDFGS YGQGTQVTVS STTTPAPRPP TPAPTIASQP LSLRPEACRP AAGGAVHTRG   180
LDFACDIYIW APLAGTCGVL LLSLVITLYC KRGRKKLLYI FKQPFMRPVQ TTQEEDGCSC   240
RFPEEEEGGC ELRVKFSRSA DAPAYQQGQN QLYNELNLGR REEYDVLDKR RGRDPEMGGK   300

SEQ ID NO: 31            moltype = AA  length = 339
FEATURE                  Location/Qualifiers
source                   1..339
                         mol_type = protein
                         organism = synthetic construct
SEQUENCE: 31
MALPVTALLL PLALLLHAAR PEVQLQASGG GLAQPGGSLR LSCAASGRTF STYFMAWFRQ    60
PPGKGLEYVG GIRWSDGVPH YADSVKGRFT ISRDNAKNTV YLQMNSLRAE DTAVYFCASR   120
GIADGSDFGS YGQGTQVTVS STTTPAPRPP TPAPTIASQP LSLRPEACRP AAGGAVHTRG   180
LDFACLPGP SKPFWVLVVV GGVLACYSLL VTVAFIIFWV RSKRSRLLHS DYMNMTPRRP   240
GPTRKHYQPY APPRDFAAYR SQPFMRPVQT TQEEDGCSCR FPEEEEGGCE LRVKFSRSAD   300
APAYQQGQNQ LYNELNLGRR EEYDVLDKRR GRDPEMGGK                          339

SEQ ID NO: 32            moltype = AA  length = 330
FEATURE                  Location/Qualifiers
source                   1..330
                         mol_type = protein
                         organism = synthetic construct
SEQUENCE: 32
MALPVTALLL PLALLLHAAR PEVQLQASGG GLAQPGGSLR LSCAASGRTF STYFMAWFRQ    60
PPGKGLEYVG GIRWSDGVPH YADSVKGRFT ISRDNAKNTV YLQMNSLRAE DTAVYFCASR   120
GIADGSDFGS YGQGTQVTVS STTTPAPRPP TPAPTIASQP LSLRPEACRP AAGGAVHTRG   180
LDFACLPGP SKPFWVLVVV GGVLACYSLL VTVAFIIFWV RSKRSRLLHS DYMNMTPRRP   240
GPTRKHYQPY APPRDFAAYR SGGGSFRTPI QEEQADAHST LARVKFSRSA DAPAYQQGQN   300
QLYNELNLGR REEYDVLDKR RGRDPEMGGK                                    330

SEQ ID NO: 33            moltype = AA  length = 321
FEATURE                  Location/Qualifiers
source                   1..321
                         mol_type = protein
                         organism = synthetic construct
SEQUENCE: 33
MALPVTALLL PLALLLHAAR PEVQLQASGG GLAQPGGSLR LSCAASGRTF STYFMAWFRQ    60
PPGKGLEYVG GIRWSDGVPH YADSVKGRFT ISRDNAKNTV YLQMNSLRAE DTAVYFCASR   120
GIADGSDFGS YGQGTQVTVS STTTPAPRPP TPAPTIASQP LSLRPEACRP AAGGAVHTRG   180
LDFACSQLCC QLKFWLPIGC AAFVVVCILG CILICWLTKK KYSSSVHDPN GEYMFMRAVN   240
TAKKSRLTDV TLGGGSFRTP IQEEQADAHS TLARVKFSRS ADAPAYQQGQ NQLYNELNLG   300
RREEYDVLDK RRGRDPEMGG K                                            321
```

CHIMERIC ANTIGEN RECEPTOR COMPRISING BCMA NANOBODY LINKED TO A CHIMERIC INTRACELLULAR SIGNALING DOMAIN

CROSS-REFERENCE TO RELATED APPLICATIONS

This application claims the benefit of and priority to U.S. Provisional Patent Application No. 63/358,399, filed Jul. 5, 2022, the contents of which are incorporated by reference herein in their entirety.

REFERENCE TO AN ELECTRONIC SEQUENCE LISTING

The contents of the electronic sequence listing (NEOM_005_001US_SeqList_ST26.xml; Size 38,729 bytes; and Date of Creation: Jul. 5, 2023) are herein incorporated by reference in their entirety.

TECHNICAL FIELD

The present disclosure provides a third-generation chimeric antigen receptor (CAR) that binds to B cell maturation antigen (BCMA). Such BCMA-CAR is effective in inducing T cell activation and proliferation, and provides enhanced cytotoxic effect in response to target cells.

BACKGROUND

While adoptive cell therapies show efficacy in cancer treatment, the effectiveness of these therapies can be further improved through genetic engineering of T cells for better expansion and persistence. In developing genetically engineered T cells for such adoptive cell therapies, there is a need to introduce chimeric T cell co-stimulatory molecules that can be locally activated upon T cell engagement with pathological antigens to potently augment T cell activation and increase therapeutic efficacy. Second generation chimeric co-stimulatory molecules incorporating one co-stimulatory signaling domain from proteins of either CD28 family or TNFR family may not be optimal for induction of durable tumor remissions. Third-generation chimeric molecules combining two co-stimulatory signaling domains from CD28 family and TNFR family members to further enhance T cell therapeutic potential, capitalizing on non-overlapping functions of the two families of co-stimulatory molecules, often suffer from reduced cell surface expression of the chimeric proteins combining two co-stimulatory signaling domains, preventing realization of the functional potential of the chimeric proteins.

The present application discloses a chimeric antigen receptor (CAR) that binds to B cell maturation antigen (BCMA) (BCMA-CAR) comprising a BCMA nanobody and third-generation chimeric T cell co-stimulatory molecule that incorporates a CD28 family signaling domain and a TNFR family signaling domain for enhanced T cell function. These enhanced functions include enhanced proliferation, killing of target cells and reduced adverse events associated with current leading clinical CARs. This application discloses exemplary BCMA-CAR proteins for use in the treatment of cancer, including but not limited to multiple myeloma, and methods of making and using these BCMA-CARs.

SUMMARY

The present disclosure provides a chimeric antigen receptor that binds to a B cell maturation antigen (BCMA-CAR), comprising: (a) an extracellular domain comprising an amino acid sequence according to SEQ ID NO: 8; (b) a transmembrane domain of ICOS; and (c) a chimeric intracellular domain comprising a first, a second and at least a third signal transduction domain, wherein the first signal transduction domain comprises an ICOS intracellular domain, the second signal transduction domain comprises a truncated CD137 (4-1BB) intracellular domain, and the at least third signal transduction domain comprises a truncated CD3ζ domain.

In some embodiments, the BCMA-CAR comprises: (a) an extracellular domain comprising an amino acid sequence according to SEQ ID NO: 8; (b) a transmembrane domain of ICOS; and (c) a chimeric intracellular domain comprising a first, a second and a third signal transduction domains, wherein the first signal transduction domain comprises an ICOS intracellular domain, the second signal transduction domain comprises a truncated CD137 (4-1BB) intracellular domain, and the third signal transduction domain comprises a truncated CD3ζ domain.

The present disclosure provides a BCMA-CAR, comprising: (a) an extracellular domain comprising an amino acid sequence according to SEQ ID NO: 1; (b) a transmembrane domain; and (c) a chimeric intracellular domain comprising a first, a second and at least a third signal transduction domains, wherein the first signal transduction domain comprises an ICOS intracellular domain according to SEQ ID NO: 2, the second signal transduction domain comprises a truncated CD137 (4-1BB) intracellular domain according to SEQ ID NO: 3, and the at least third signal transduction domain comprises a truncated CD3 domain according to SEQ ID NO: 4.

In some embodiments, the BCMA-CAR comprises: (a) an extracellular domain comprising an amino acid sequence according to SEQ ID NO: 1; (b) a transmembrane domain; and (c) a chimeric intracellular domain comprising a first, a second and a third signal transduction domains, wherein the first signal transduction domain comprises an ICOS intracellular domain according to SEQ ID NO: 2, the second signal transduction domain comprises a truncated CD137 (4-1BB) intracellular domain according to SEQ ID NO: 3, and the third signal transduction domain comprises a truncated CD3ζ domain according to SEQ ID NO: 4.

In some embodiments, the extracellular domain further comprises a signal peptide, a hinge, or an ICOS extracellular stalk, or a combination thereof. In some embodiments, the extracellular domain further comprises a CD8a signal peptide, a CD8a hinge, an ICOS extracellular stalk, or a combination thereof. In some embodiments, the extracellular domain further comprises a CD8a signal peptide according to SEQ ID NO: 6, a CD8a hinge according to SEQ ID NO: 7, an ICOS extracellular stalk according to SEQ ID NO: 9, or a combination thereof.

In some embodiments, the extracellular domain comprises the amino acid sequence of SEQ ID NO: 1.

In some embodiments, the transmembrane domain comprises the amino acid sequence of SEQ ID NO: 10.

The present disclosure also provides a BCMA-CAR comprising the amino acid sequence of SEQ ID NO: 5. The present disclosure also provides a nucleic acid encoding the BCMA-CAR of the present disclosure. The present disclosure also provides a vector comprising the nucleic acid of the present disclosure. The present disclosure also provides a cell comprising the nucleic acid or the vector of the present disclosure. Compositions, e.g., pharmaceutical compositions, comprising the BCMA-CAR, the nucleic acid, the vector, and/or the cell of the present disclosure are also provided herein.

The present disclosure also provides a modified T cell, comprising: (a) a modification of an endogenous sequence encoding a T cell Receptor (TCR), wherein the modification reduces or eliminates a level of expression or activity of the TCR; and (b) a BCMA-CAR disclosed herein.

The present disclosure also provides a method of producing a plurality of modified T cells, wherein the method comprises: a) providing a plurality of primary T cells; b) providing a composition comprising the BCMA-CAR of the present disclosure, the nucleic acid of the present disclosure, or the vector of the present disclosure; and c) introducing into the plurality of primary T cells of (a) the composition of (b), to produce a plurality of modified T cells under conditions that stably express the BCMA-CAR within the plurality of modified T cells.

The present disclosure also provides a composition comprising any one of the BCMA-CAR of the present disclosure, the nucleic acid of the present disclosure, the vector of the present disclosure, the cell of the present disclosure, or the modified T cell of the present disclosure.

The present disclosure also provides a method of treating a disease or disorder, comprising administering to a subject in need thereof a therapeutically effective number of the cell of the present disclosure, a therapeutically effective number of the modified T cell of the present disclosure, a therapeutically effective amount of the composition of the present disclosure, or a therapeutically effective number of the plurality of modified T cells produced by the method of the present disclosure.

In some embodiments, the disease or disorder is a cancer, an autoimmune disease or disorder, or an inflammatory disease. In some embodiments, the cancer is a hematologic cancer. In some embodiments, the hematological cancer is a leukemia, a lymphoma, or a myeloma. In some embodiments, the cancer is selected from acute leukemia, acute lymphoblastic leukemia (ALL), acute lymphocytic leukemia, B cell, T cell or FAB ALL, acute myeloid leukemia (AML), acute myelogenous leukemia, chronic myelocytic leukemia (CML), chronic lymphocytic leukemia (CLL), hairy cell leukemia, myelodysplastic syndrome (MDS), Hodgkin's lymphoma, Hodgkin's disease, non-Hodgkin's lymphoma, and multiple myeloma. In some embodiments, the cancer is a multiple myeloma. In some embodiments, the cancer expresses BCMA. In some embodiments, the subject is a mammal. In some embodiments, the mammal is a human.

BRIEF DESCRIPTION OF THE DRAWINGS

FIG. 2A shows bar graphs depicting the surface expression of CAR receptors. FIG. 2B shows flow cytometry histograms of data from FIG. 2A. FIG. 2C shows BCMA mean fluorescence intensity (MFI) of the transduced T cell population. FIG. 2D shows flow cytometry histograms of data from FIG. 2C.

FIG. 3A shows IL-2 production. FIG. 3B shows TNFα ("TNF") production. FIG. 3C shows IFNγ production. The x-axis depicts the ratio of effector CAR T cells to target tumor cells (E:T). The y-axis depicts the cytokine production as measured by multiplex assay on 18-hr co-culture supernatants.

FIGS. 4A-4C show line graphs depicting the killing of tumor cell lines by a BCMA-CAR of the present disclosure ("NPB5005-ICOSBBtZt") during co-culture compared to effector CAR T cell therapy controls targeting BCMA (bb2121, FHVH33, and LCARB38M). FIG. 4A shows percent killing of MM.15 tumor cells. FIG. 4B shows the percent killing of U266 tumor cells. FIG. 4C shows percent killing of RPMI8226 tumor cells. The x-axis depicts the ratio of effector CAR T cells to target tumor cells (E:T). The y-axis depicts the percentage of tumor cells killed. The effector CAR T cells are as indicated.

FIG. 5A shows a schematic depiction of a method of testing proliferation and function of T cells expressing an exemplary BCMA-CAR disclosed herein ("NPB5005-ICOSBBtZt") compared to T cells expressing control CARs. RPMI8226 myeloma cells expressing BCMA were co-cultured with BCMA-CAR T cells for a total of 16 days and stimulated with 100,000 additional fresh RPMI8226 cells on Day 4, Day 8, and Day 12. FIG. 5B shows line graphs depicting cumulative T cell number over multiple stimulations. FIG. 5C shows line graphs depicting target cell number at the end of each stimulation.

FIG. 6A are PD1 flow cytometry plots with T cells from two separate donors (top and bottom panels). FIG. 6B shows bar graphs depicting percentage cells expressing PD1 for RPMI-8226 cells. FIG. 6C shows bar graphs depicting percentage cells expressing PD1 for U266 cells.

FIG. 7A depicts line graphs of IL2 production after an 18-hour co-culture of CAR-transduced cells with RPMI-8226 cells at the indicated effector to target (E:T) ratio. FIG. 7B depicts line graphs of CAR positive cells over multiple stimulations with RPMI-8226 multiple myeloma cells.

FIG. 8A shows flow cytometry plots of T cells transduced with NPB5005-ICOSBBtZt and reference CAR constructs and K562-BCMA engineered target cells over multiple repeated stimulations. FIG. 8B are plots depicting K562.GFP (left) and K562.BCMA.GFP (right) cell number after a 96-hour co-culture with T cells transduced with the indicated CAR constructs. FIG. 8C are plots depicting T cell number after a 96-hour co-culture with either K562.GFP (left) or K562.BCMA.GFP (right) cells. FIG. 8D depicts bar graphs of target (left) and T cell numbers (right) of the indicated CAR-T cell population and K562.BCMA.GFP target cell population after multiple stimulations.

FIG. 9A shows line graphs evaluating cytokine production by CAR-transduced T cells at various E:T ratios in response to stimulation with K562.GFP and K562.BCMA.GFP target cells. FIG. 9B shows plots of PD1 expression on the surface of T cells transduced with the indicated CAR constructs in response to K562.BCMA.GFP target cells.

FIGS. 10A-10C depict intermediate CAR-intrinsic tonic signaling of a BCMA-CAR of the present disclosure ("NPB5005-ICOSBBtZt"). FIG. 10A shows flow cytometry plots depicting T cell proliferation marked by dilution of Tag-It Violet dye of T cells after 96 hours treated with the indicated stimulation condition. FIG. 10B depicts bar graphs quantifying the cell numbers shown in FIG. 10A, with a zoomed-in panel showing T cell number in the absence of exogenous stimulation. FIG. 10C shows bar graphs depicting cytokine production at the indicated E:T ratio in the absence of the BCMA target protein.

FIG. 11A shows intravital imaging of MM.1S xenograft tumor burden in mice after being treated with increasing doses of NPB5005-ICOSBBtZt at post-infusion days 4, 10, and 18. FIG. 11B shows measurement of tumor burden (using soluble luciferase) from MM.1S tumor-bearing mice treated with the indicated T cell population. FIG. 11C shows the survival curve for MM.1S tumor-bearing female mice treated with the indicated T cell population. FIG. 11D shows the survival curve for MM.1S tumor-bearing male mice treated with the indicated T cell population.

Figure 1:
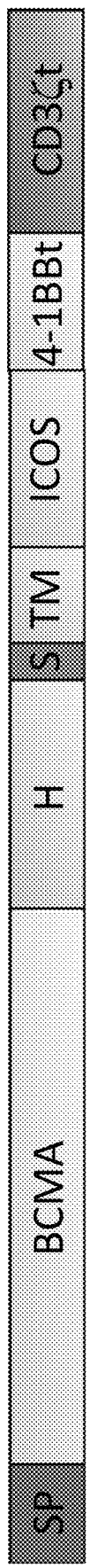
FIG. 1 shows a schematic depicting the structure and orientation of the extracellular, transmembrane, and intracellular signaling domains of the exemplary BCMA-CAR disclosed herein ("NPB5005-ICOSBBtZt" also referred to as "Receptor 1"). SP: signal peptide, BCMA: BCMA-binding nanobody, H: hinge, S: stalk, TM: transmembrane domain, ICOS: ICOS intracellular domain, 4-1BBt: 4-1BB intracellular domain with N-terminal truncation, CD3ζt: CD3ζ domain with C-terminal truncation of ITAM2 and ITAM3.

In certain Figures and Examples described herein, the following abbreviations are used to describe domains of BCMA-CARs: "CD28" or "28" for CD28; "2" for CD2; "3" for CD3; "4" for CD4; "CD8" for CD8a; "BB" for 4-1BB; "BBt" for truncated 4-1BB; "Z" for CD3ζ; "Zt" for truncated CD3ζ; "OX40" or "40" for OX-40, and "40t" or "OX40t" for truncated OX-40. Domains are ordered from BCMA-binding domain to extracellular domain(s) to intracellular domain(s).

DETAILED DESCRIPTION

Provided herein are improved chimeric antigen receptors that bind to B cell maturation antigen (BCMA-CAR) comprising: (a) an extracellular domain; (b) a transmembrane domain; and (c) a chimeric intracellular domain comprising a first, a second and at least a third signal transduction domain, wherein the first signaling domain is based on the intracellular signaling domain of a CD28 family protein (e.g., ICOS), the second signaling domain comprises a mutant intracellular signaling domain of a tumor necrosis factor receptor (TNFR) family protein (e.g., 4-1BB), and the at least third intracellular signaling domain is derived from a CD3 signaling domain (e.g., CD3ζ).

Provided herein is a BCMA-CAR (e.g., NPB5005-ICOSBBtZt) that displays high on-target efficacy and low levels of adverse phenotypic events. The BCMA-CAR of the present disclosure (e.g., NPB5005-ICOSBBtZt) provides increased effector cell (e.g., T cell) function, proliferation, and retains such phenotypes over multiple stimulations. Further, the BCMA-CAR of the present disclosure (e.g., NPB5005-ICOSBBtZt) produces low cytokine levels and low surface PD-1 expression. Such properties of the BCMA-CAR of the disclosure (e.g., NPB5005-ICOSBBtZt) provide numerous technical advantages over control BCMA-CARs tested.

In some embodiments, a BCMA-CAR of the present disclosure (e.g., NPB5005-ICOSBBtZt) retains increased effector cell function (e.g., T cell proliferation) over multiple rounds of stimulation, e.g., two rounds, three rounds, four rounds, with target cells, e.g., cancer cells. In certain embodiments, the increase in effector cell function (e.g., T cell proliferation) is at least two-fold, at least three-fold, at least four-fold, or at least five-fold over a control BCMA-CAR. In some embodiments, a BCMA-CAR of the present disclosure (e.g., NPB5005-ICOSBBtZt) retains increased effector cell function (e.g., target cell cytolysis, e.g., cancer cell cytolysis) over multiple rounds of stimulation, e.g., two rounds, three rounds, four rounds, with target cells, e.g., cancer cells. In certain embodiments, the increase in effector cell function (e.g., target cell cytolysis, e.g., cancer cell cytolysis) is at least two-fold, at least three-fold, at least four-fold, or at least five-fold over a control BCMA-CAR.

In some embodiments, a BCMA-CAR of the present disclosure (e.g., NPB5005-ICOSBBtZt) retains decreased adverse phenotypic events (e.g., surface PD-1 expression) over multiple rounds of stimulation, e.g., two rounds, three rounds, four rounds, with target cells, e.g., cancer cells. In certain embodiments, the decreased adverse phenotypic events (e.g., surface PD-1 expression) is at least two-fold, at least three-fold, at least four-fold, or at least five-fold over a control BCMA-CAR. In some embodiments, a BCMA-CAR of the present disclosure (e.g., NPB5005-ICOSBBtZt) retains decreased adverse phenotypic events (e.g., tonic cytokine production, e.g., IL-2, IFNγ, or TNFα) over multiple rounds of stimulation, e.g., two rounds, three rounds, four rounds, with target cells, e.g., cancer cells. In certain embodiments, the decreased adverse phenotypic events (e.g., tonic cytokine production, e.g., IL-2, IFNγ, or TNFα) is at least two-fold, at least three-fold, at least four-fold, or at least five-fold over a control BCMA-CAR.

In some aspects, the chimeric intracellular domain of the BCMA-CAR of the present disclosure enhances the activity and efficacy of the BCMA-CAR. For example, when expressed in T cells, the BCMA-CAR of the present disclosure enhances T cell stimulation, proliferation, persistence, and killing of target myeloma cells expressing BCMA. BCMA-CAR T cells can eliminate BCMA-positive multiple myeloma cells with equivalent potency and superior efficacy to the leading clinical CAR T cell therapies directed against BCMA (e.g., bb2121, FHVH33, and LCARB38M) while producing significantly less cytokines. Accordingly, in some embodiments, the combination of improved T cell proliferation, persistence, tumor cell killing, reduced inflammatory cytokine production, and lower surface expression of PD-1, make the BCMA-CAR proteins of the present disclosure superior to leading BCMA-CAR T cell therapies.

Tumor associated antigens and tumor specific antigens allow for the immunological targeting of the tumor with relatively minimal risk of off-tumor, on-target side effects. Tumor cells can upregulate these antigens which can then be targeted by the human immune response. The disclosure herein provides a chimeric intracellular domain that combines an ICOS intracellular domain and a 4-1BB intracellular domain to provide a co-stimulatory molecule that exhibits superior functionality to other CD28- or 4-1BB-based receptors to generate a BCMA-CAR product that contributes to enhanced T cell proliferation, killing efficacy and resistance to the suppressive function of the tumor microenvironment.

In some aspects, the present disclosure also provides a nucleic acid encoding the BCMA-CAR disclosed herein. In some embodiments, the nucleic acid encoding the BCMA-CAR disclosed herein comprises a nucleotide sequence according to SEQ ID NO: 11.

In some embodiments, the nucleic acid disclosed herein comprises a nucleic acid sequence encoding a chimeric intracellular domain. In some embodiments, the BCMA-CAR disclosed herein is for expression in a T cell, wherein the T cell co-expresses at least one of the endogenous co-stimulatory molecules CD28, CD2, OX-40, ICOS, CD28, CD3, CD4, CD8 and CD40L or a combination thereof.

In some aspects, the present disclosure also provides a vector comprising the nucleic acid disclosed herein. In some embodiments, the vector disclosed herein is any one of a viral vector, a plasmid, a mini-circle DNA, a cosmid, a yeast artificial chromosome, a bacterial artificial chromosome, or a transposon/transposase system. In some embodiments, the viral vector is an adeno-viral vector or a lentiviral vector. In some embodiments, the vector is a lentiviral vector.

In some aspects, the present disclosure also provides a cell comprising the nucleic acid or the vector disclosed herein. In some embodiments, the cell disclosed herein is a modified T cell. In some embodiments, the modified T cell is an allogeneic T cell. In some embodiments, the modified T cell is an autologous T cell. In some embodiments, the modified T cell is any one of a naïve T cell, an early memory T cell, a stem cell-like T cell, a stem memory T cell (TSCM), a central memory T cell (TCM) and a regulatory T cell (Treg).

In some embodiments, the BCMA-CAR comprises an extracellular domain of SEQ ID NO: 1. In some embodiments, the BCMA-CAR comprises a first signal transduction domain of SEQ ID NO: 2, a second signal transduction domain of SEQ ID NO: 3, and a third signal transduction domain of SEQ ID NO: 4. In some embodiments, the BCMA-CAR comprises the sequence of SEQ ID NO: 5.

Definitions

Unless otherwise indicated, "B cell maturation antigen", "recombinant B cell maturation antigen", and "BCMA" are used interchangeably. B cell maturation antigen, also known as CD269, is a member of the tumor necrosis factor receptor superfamily 17 is highly selectively expressed on the surface of multiple myeloma (MM) cells (Guo, R et al. Front Immunol vol. 13:839097). Under physiological conditions, BCMA is mainly expressed on plasmablasts and terminally differentiated plasma cells (PCs). In the pathological case, BCMA is expressed nearly on all MM tumor cell lines (80%-100%), and the quantity of BCMA on the surface of malignant PCs is much higher than regulator PCs (Lee L, et al. Br J Haematol (2016) 174:911-22). Its expression is restricted to the B-cell lineage and has been shown to be important for B cell development and autoimmune response.

As used herein, "BCMA specific" (e.g., a BCMA specific T cell receptor or BCMA specific chimeric antigen receptor) refers to a binding agent that binds selectively to an antigen or epitope of BCMA, such as with a high affinity, and does not significantly bind to other unrelated antigens or epitopes.

"CD137" as described herein is a member of the tumor necrosis factor (TNF) receptor family, and also referred to as 4-1BB, CD137, tumor necrosis factor receptor superfamily member 9 (TNFRSF9) and induced by lymphocyte activation (ILA). As described herein, the terms "CD137", "4-1BB", "4-1BB wt", "4-1BB wild type", "BB", "BB wt" and "BB wild type" are used interchangeably throughout, for example, when describing constructs or co-stimulatory molecules of the present application, unless otherwise indicated.

A truncated CD137 intracellular domain as described herein, is referred to as "truncated CD137", "CD137t", "truncated 4-1BB", "4-1BBt", "truncated BB" or "BBt" interchangeably throughout, for example, when describing constructs or co-stimulatory molecules of the present application, unless otherwise indicated. In some embodiments, the mutant CD137 intracellular domain comprises a deletion of one, two, three or four lysine residue(s) from amino acid position 1 to amino acid position 12 of the N-terminus of the CD137 intracellular domain, of the present disclosure. In some embodiments, the mutant CD137 intracellular domain comprises one or more lysine mutation(s) from amino acid position 1 to amino acid position 12 of the N-terminus of the CD137 intracellular domain, of the present disclosure. In some embodiments, the mutant CD137 intracellular domain comprises one or more lysine mutation(s) at amino acid positions selected from amino acid positions 1, 5, 6 and 12 of the N-terminus of the CD137 intracellular domain, of the present disclosure. In some embodiments, the one or more lysine mutation(s) are lysine to alanine mutations. In some embodiments, the CD137 intracellular domain comprises an amino acid sequence according to SEQ ID NO: 3.

Unless indicated otherwise, the terms "co-stimulatory molecule", "costimulatory molecule", "co stimulatory molecule", "co-stimulatory protein", "costimulatory protein", "co stimulatory protein", "co-stimulatory receptor", "costimulatory receptor" "co stimulatory receptor" and "switch receptor" are used interchangeably, to refer to the recombinant T cell co-stimulatory receptors (RTCRs) comprising the novel chimeric co-stimulatory intracellular domains of the present application. These terms may be used in combination with terms such as "recombinant T cell", "recombinant", "chimeric T cell", and "chimeric", to refer to the RTCRs of the present application.

As described herein, "a recombinant T cell co-stimulatory receptor" or "switch receptor" of the present disclosure is a "costimulatory molecule" "co-stimulatory receptor" or "co-stimulatory protein" generated by operably linking an extracellular domain to an intracellular chimeric intracellular protein of the present disclosure.

The terms T cell, T-cell, t cell, t-cell, and T lymphocyte can be used interchangeably in the present disclosure.

The terms "NPB5005-ICOSBBtZt", "BCMA-ICOSBBtZt", "NPB5005-BCMA-ICOSBBtZt", "Receptor 1", "receptor 1", "Construct 1", "construct 1", and "V283" are used interchangeably in the present disclosure to refer to an exemplary BCMA CAR of the present disclosure or T cell expressing an exemplary BCMA CAR of the present disclosure.

The terms "subject" and "patient" refer to an organism to be treated by the methods and compositions described herein.

The term "about" or "approximately" can be understood as within 10%, 9%, 8%, 7%, 6%, 5%, 4%, 3%, 2%, 1%, 0.5%, 0.1%, 0.05%, or 0.01% of the stated value. In some embodiments, "about" or "approximately" can be understood as within 5%, 4%, 3%, 2%, 1%, 0.5%, 0.1%, 0.05%, or 0.01% of the stated value. In some embodiments, "about" or "approximately" can be understood as within 2%, 1%, 0.5%, 0.1%, 0.05%, or 0.01% of the stated value. In some embodiments, "about" or "approximately" can be understood as within 1%, 0.5%, 0.1%, 0.05%, or 0.01% of the stated value.

Throughout the disclosure, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

Extracellular Domain

Provided herein is a BCMA-CAR comprising an extracellular domain.

In some embodiments, the extracellular domain comprises a protein, a peptide, a glycoprotein, an antibody or a fragment thereof that binds to BCMA, e.g., an antigen-binding fragment. In some embodiments, the antibody or fragment thereof is a Fab fragment, a F(ab)$_2$ fragment, a diabody, a nanobody, a sdAb, Fv, a VHH fragment, or a single chain Fv fragment. In some embodiments, the antibody or fragment thereof is a nanobody. In some embodiments, the nanobody comprises the amino acid sequence having at least 50%, 55%, 60%, 65%, 70%, 75%, 80%, 85%, 90%, 95%, 97% or 99% identity to the amino acid sequence of SEQ ID NO: 8. In some embodiments, the nanobody comprises the amino acid sequence of SEQ ID NO: 8.

In some embodiments, the extracellular domain is a B cell maturation antigen (BCMA) binding protein. In some embodiments, the BCMA binding protein is a BCMA specific T cell receptor (TCR). In some embodiments, the BCMA binding protein is a nanobody. In some embodiments, the BCMA binding protein is a BCMA specific chimeric antigen receptor (CAR).

In some embodiments, the extracellular domain comprises two or more binding sites for targeting two or more non-identical target antigens. In some embodiments, the extracellular domain comprises two or more binding sites for targeting two or more non-identical sites on a target antigen. In some embodiments, the extracellular domain comprises two antigen binding domains or fragments of a bispecific antibody. In some embodiments, the extracellular domain comprises a F(ab)$_2$ fragment of a bispecific antibody. In some embodiments, the extracellular domain comprises two or more antigen binding domains or fragments of a multi-specific antibody.

Signal Peptide

In some embodiments, the extracellular domain comprises a signal peptide, e.g., at the N-terminus. In some embodiments, the signal peptide can be derived from a surface expressing protein or a secretory protein. In some embodiments, the signal peptide can be derived from Pre-prolactin, HIV pre-Env, HCV polyprotein, CB virus polyprotein, Pestivirus polyprotein, Precalreticulin, pre-VSV-G, HLA class I histocompatibility antigen or PD-1 signal peptide (PD-1 SP), interleukin 12 (IL12), GM-CSF, or CD8 alpha chain (CD8a) signal peptide.

In some embodiments, the signal peptide is derived from a CD8a signal peptide. In some embodiments, the CD8a signal peptide comprises an amino acid sequence having at least 50%, 55%, 60%, 65%, 70%, 75%, 80%, 85%, 90%, 95%, 97% or 99% identity to the amino acid sequence of SEQ ID NO: 6. In some embodiments, the CD8a signal peptide comprises an amino acid sequence of SEQ ID NO: 6.

Hinge

In some embodiments, the extracellular domain comprises a hinge region. In some embodiments, the hinge region is derived from CD8, PD-1, CD28, ICOS, or IgG hinge domain. In some embodiments, the hinge region is derived from CD8 alpha chain (CD8a) hinge. In some embodiments, the CD8a hinge region comprises an amino acid sequence having at least 50%, 55%, 60%, 65%, 70%, 75%, 80%, 85%, 90%, 95%, 97% or 99% identity to the amino acid sequence of SEQ ID NO: 7. In some embodiments, the CD8a hinge region comprises the amino acid sequence of SEQ ID NO: 7.

Stalk

In some embodiments, the extracellular domain comprises a stalk region. In some embodiments, the stalk region is derived from CD8, PD-1, CD28, ICOS, or IgG. In some embodiments, the hinge region is derived from ICOS. In some embodiments, the ICOS stalk region comprises an amino acid sequence having at least 50%, 55%, 60%, 65%, 70%, 75%, 80%, 85%, 90%, 95%, 97% or 99% identity to the amino acid sequence of SEQ ID NO: 9. In some embodiments, the ICOS stalk region comprises the amino acid sequence of SEQ ID NO: 9.

In some embodiments, the extracellular domain further comprises one or more of a signal peptide, a hinge, and an ICOS extracellular stalk, or a combination thereof. In some embodiments, the extracellular domain further comprises one or more of a CD8a signal peptide, a CD8a hinge, an ICOS extracellular stalk, or a combination thereof.

In some embodiments, the CD8a signal peptide comprises an amino acid sequence according to SEQ ID NO: 6. In some embodiments, the CD8a hinge comprises an amino acid sequence according to SEQ ID NO: 7. In some embodiments, the ICOS extracellular stalk comprises an amino acid sequence according to SEQ ID NO: 9. In some embodiments, the extracellular domain further comprises one or more of a CD8a signal peptide according to SEQ ID NO: 6, a CD8a hinge according to SEQ ID NO: 7, and an ICOS extracellular stalk according to SEQ ID NO: 9, or a combination thereof.

In some embodiments, the extracellular domain comprises the amino acid sequence of SEQ ID NO: 1.

Transmembrane Domain

In some embodiments, the transmembrane domain of the BCMA-CAR disclosed herein is derived from CD8, PD1, CD28, ICOS, or IgG transmembrane domain. In some embodiments, the transmembrane domain is located between the extracellular domain and the first signal transduction domain. In some embodiments, the transmembrane domain is derived from an ICOS transmembrane domain. In some embodiments, the ICOS transmembrane domain comprises an amino acid sequence having at least 50%, 55%, 60%, 65%, 70%, 75%, 80%, 85%, 90%, 95%, 97% or 99% identity to the amino acid sequence of SEQ ID NO: 10. In some embodiments, the ICOS transmembrane domain comprises the amino acid sequence of SEQ ID NO: 10.

Intracellular Signaling Domains

ICOS Domain

In some embodiments, the BCMA-CAR of the present disclosure comprises a first signal transduction domain derived from an ICOS protein.

The CD28 family proteins have a single extracellular immunoglobulin variable-like (IgV) domain followed by a short cytoplasmic tail. Members of the CD28 family proteins include CD28, CD28H, inducible costimulator (ICOS), cytotoxic T lymphocyte-associated antigen 4 (CTLA-4, CD152), program death-1 (PD-1), and B- and T-lymphocyte attenuator (BTLA). CD28, CD28H, and ICOS are co-stimulatory proteins that are expressed on T cells and, for example, promote their activation, high levels of cytokine/chemokine expression, resistance to apoptosis, and proliferation of T cells. In some embodiments, the first signaling domain that is based on the intracellular signaling domain of a CD28 family protein is an ICOS protein.

The "ICOS protein" as described herein is an inducible T cell co-stimulatory protein, also referred to as AILIM, CD278, CCLP, CRP-1, H4, Ly115 and CVID1. In some embodiments, the ICOS intracellular domain can be from a mammalian ICOS. In some embodiments, the mammalian ICOS can be a human ICOS, a mouse ICOS, a rat ICOS or a monkey ICOS. In some embodiments, the ICOS intracellular domain can be derived from a human ICOS, or an isoform or a variant thereof, e.g., comprising an amino acid sequence identical to any one of the human ICOS amino acid sequences according to GenBank Accession Nos: AAH28006.1, NP_036224.1, AIC51287.1, AIC60036.1, NP_036224.1, Q9Y6W8.1, EAW70357.1, EAW70356.1, EAW70355.1, AAL40934.1, AAL40933.1, CAC06612.1, AAX93073.1, AAM00909.1, AAH28210.1 and CAD59742.1. In some embodiments, the ICOS intracellular domain can be derived from a mouse ICOS, or an isoform or a variant thereof, e.g., comprising an amino acid sequence identical to any one of the mouse ICOS amino acid sequences according to GenBank Accession Nos: NP_059508.2, Q9WVS0.2, EDL00161.1, CAM13242.1, CAM13241.1, CAB71153.1, AAG48732.1, AAH34852.1, XP_006496203.1, XP_006496202.1, XP_006496201.1, ACX50464.1, ACX50463.1, AAH28006.1, XP_021052880.1, XP_029334968.1 and XP_021030282.1. In some embodiments, the ICOS intracellular domain can be derived from a rat ICOS, or an isoform or a variant thereof, e.g., comprising an amino acid sequence identical to any one of the rat ICOS amino acid sequences according to GenBank Accession Nos: NP_072132.1, Q9R1T7.1, XP_008765358.1, XP_006245100.1, XP_006245099.1, EDL98922.1, EDL98921.1, XP_038940099.1, XP_032755449.1, XP_017457364.1, XP_006256324.1, XP_006256323.1, XP_006256322.1, XP_029425757.1, XP_029425757.1, XP_021119236.1, XP_012929934.1, XP_012867370.1 and XP_012867363.1. In some embodiments, the ICOS intracellular domain can be derived from a non-human primate ICOS, or an isoform or a variant thereof, e.g., comprising an amino acid sequence identical to any one of the monkey ICOS amino acid sequences according to GenBank Accession Nos: XP_007964137.1, NP_001253918.1, XP_010350939.1, XP_012301785.1, XP_012301784.1, XP_017739861.1, XP_010334714.1, XP_003925677.1, AFH29328.1, XP_008997520.1, XP_023075107.1, XP_023075099.1, XP_021779593.1, XP_003907887.1, XP_025260988.1, XP_025260987.1, XP_025260986.1, XP_011716287.1, XP_011716285.1, XP_005574075.1, XP_011903009.1, XP_011805288.1, XP_011805287.1, XP_011847867.1, XP_011847866.1, XP_017392362.1, XP_033086489.1, XP_032134414.1, XP_032134413.1, and XP_017802331.1.

In some embodiments, the chimeric intracellular domain comprises a first signal transduction domain derived from a protein of the CD28 family. In some embodiments, the first signal transduction domain is derived from any one of CD28, CD28H, ICOS, or a combination thereof.

In some embodiments, the first signal transduction domain derived from ICOS comprises an amino acid sequence according to SEQ ID NO: 2. In some embodiments, the first signal transduction domain derived from ICOS comprises an amino acid sequence comprising having at least 50%, 55%, 60%, 65%, 70%, 75%, 80%, 85%, 90%, 95%, 97% or 99% identity to the amino acid sequence of SEQ ID NO: 2.

4-1BB Intracellular Domain

The Tumor Necrosis Factor Receptor (TNFR) family proteins includes TNFR1 (tumor necrosis factor receptor 1/TNFRSF1A), TNFR2 (tumor necrosis factor receptor 2/TNFRSF1B), lymphotoxin β receptor/TNFRSF3, OX40/TNFRSF4, CD40/TNFRSF5, Fas/TNFRSF6, decoy receptor 3/TNFRSF6B, CD27/TNFRSF7, CD30/TNFRSF8, 4-1BB/TNFRSF9, DR4 (death receptor 4/TNFRSF10A), DR5 (death receptor 5/TNFRSF10B), decoy receptor 1/TNFRSF10C, decoy receptor 2/TNFRSF10D, RANK (receptor activator of NF-kappa B/TNFRSF11A), OPG (osteoprotegerin/TNFRSF11B), DR3 (death receptor 3/TNFRSF25), TWEAK receptor/TNFRSF12A, TACI/TNFRSF13B, BAFF-R (BAFF receptor/TNFRSF13C), HVEM (herpes virus entry mediator/TNFRSF14), nerve growth factor receptor/TNFRSF16, BCMA (B cell maturation antigen/TNFRSF17, GITR (glucocorticoid-induced TNF receptor/TNFRSF18), TAJ (toxicity and JNK inducer/TNFRSF19), RELT/TNFRSF19L, DR6 (death receptor 6/TNFRSF21), TNFRSF22, TNFRSF23, ectodysplasin A2 isoform receptor/TNFRS27 and ectodysplasin 1-anhidrotic receptor. Interactions between tumor necrosis factor superfamily (TNFSF) ligands and TNF receptor superfamily (TNFRSF) receptors provide the co-stimulatory signals that control the survival, proliferation, differentiation, and effector function of immune cells. Depending upon the specific intracellular signal induced by TNFRSF members, they can be categorized into three groups—death domain (DD)-containing receptors, decoy receptors, and TNF receptor-associated factor (TRAF)-binding receptors. Some TNFRSFs such as TNFR-1, Fas, DR3, DR4, DR5, and DR6, contain their own DDs and/or interact with other cytoplasmic DD-containing adaptor molecules. Some other TNFRSFs, such as TNFR-2, CD27, CD30, CD40, glucocorticoid-induced TNFR family-related gene (GITR), Fnl, lymphotoxin beta-receptor (LTβR), OX40, receptor activator of NF-κB (RANK), and XEDAR, lack a DD and contain motifs with four to six amino acids called TRAF-interacting motifs (TIMs) which recruits TRAF proteins. TRAF proteins are adaptor molecules that activate multiple downstream signaling pathways such as NF-κB, Janus kinase (JNK), ERK, p38MAPK, and PI3K that help in cell survival, proliferation, and cytokine production. In some embodiments, the second signaling domain is based on a mutant of the intracellular signaling domain of a TNFR family protein and is CD137 (4-1BB).

In some embodiments, the CD137 intracellular domain can be derived from a mammalian CD137. In some embodiments, the mammalian CD137 can be derived from a human CD137, a mouse CD137, a rat CD137, or a non-human primate CD137. In some embodiments, the CD137 intracellular domain can be derived from a human CD137, or an isoform or a variant thereof, e.g., comprising an amino acid sequence identical to any one of the human CD137 amino acid sequences according to GenBank Accession Nos: U03397, AAA62478, NP_001552, Q07011, AAH06196 and XP_006710681. In some embodiments, the CD137 intracellular domain can be derived from a mouse CD137, or an isoform or a variant thereof, e.g., comprising an amino acid sequence identical to any one of the mouse CD137 amino acid sequences according to GenBank Accession Nos: NP_001070977.1, NP_001070976.1, NP_035742.1, NP_033430.1, P20334.1, XP_011248530.1, XP_011248530.1, ABI30213.1, BAE32724.1 and AAH28507.1. In some embodiments, the CD137 intracellular domain can be derived from a rat CD137, or an isoform or a variant thereof, e.g., comprising an amino acid sequence identical to any one of the rat CD137 amino acid sequences according to GenBank Accession Nos: NP_852049.1, NP_001020944.1, BAD99404.1, XP_008762504.1, XP_006239534.1, EDL81196.1, AAH97483.1, EHB16663.1, EHB16663.1, KF038282.1, XP_010618177.1, XP_029414155.1, XP_029414154.1, XP_021099219.1 and XP_012888584.1. In some embodiments, the CD137 intracellular domain can be from a non-human primate CD137, or an isoform or a variant thereof, comprising an amino acid sequence identical to any one of the non-human primates CD137 amino acid sequences according to GenBank Accession Nos: ABY47575.1, ABI30212.1, ABY47577.1, ABY47576.1 and ABY47578.1.

In some embodiments, the CD137 intracellular domain, as described herein, comprises an amino acid sequence starting from the amino acid position 214 to the last amino acid at the C-terminal end of the amino acid sequence of the human CD137 protein, as described herein.

In some embodiments, the CD137 intracellular domain, as described herein, comprises an amino acid sequence starting from the amino acid position 215 to the last amino acid at the C-terminal end of the amino acid sequence of the mouse CD137 protein, as described herein.

In some embodiments, the mutant CD137 intracellular domain described herein is derived from any one of the CD137 proteins as described herein, comprising one or more mutation(s), wherein the mutation can be an addition/insertion, deletion/truncation, or substitution/replacement of one or more amino acids within the amino acid sequence of the CD137 protein. In some embodiments, the mutant CD137 intracellular domain described herein is any one of the CD137 intracellular domain sequences, as described herein, comprising one or more mutation(s), wherein the mutation can be an addition/insertion, deletion/truncation, or substitution/replacement of one or more amino acids within the amino acid sequence of the CD137 intracellular domain. In some embodiments, the mutant CD137 intracellular domain described herein is a CD137 intracellular domain as described herein, comprising a deletion or substitution of one or more amino acids within the amino acid sequence of the CD137 intracellular domain that can be targets for ubiquitination. In some embodiments, the mutant CD137 intracellular domain described herein is a CD137 protein as described herein, comprising a deletion or substitution of one or more lysine residues within the amino acid sequence of the CD137 intracellular domain that can be targets for ubiquitination. In some embodiments, the mutant CD137 intracellular domain described herein is a CD137 protein as described herein, comprising a deletion or substitution of one, two, three or four lysine residues within the amino acid sequence of the CD137 intracellular domain that can be targets for ubiquitination. In some embodiments, the lysine residues within the amino acid sequence of the CD137 intracellular domain described herein, that can be deleted or substituted are at amino acid positions 214, 218, 219 and/or 225 of the CD137 intracellular domain. In some embodiments, the mutant CD137 intracellular domain described herein is a CD137 protein as described herein, comprising a deletion or substitution of K214. In some embodiments, the mutant CD137 intracellular domain described herein is a CD137 protein as described herein, comprising a deletion or substitution of K218. In some embodiments, the mutant CD137 intracellular domain described herein is a CD137 protein as described herein, comprising a deletion or substitution of K219. In some embodiments, the mutant CD137 intracellular domain described herein is a CD137 protein as described herein, comprising a deletion or substitution of K225.

In some embodiments, the mutant CD137 intracellular domain can be a truncated CD137 intracellular domain. A truncated CD137 intracellular domain as described herein can be any one of the CD137 proteins described herein, in which a continuous stretch of more than one, two, three, four, five, six, seven, eight, nine, ten, eleven, twelve, thirteen, fourteen, fifteen, twenty, twenty-five, fifty, hundred, two hundred or more amino acids are deleted from the N-terminus the CD137 protein as described herein. A truncated CD137 intracellular domain as described herein can be any one of the CD137 intracellular domain sequences described herein, in which a continuous stretch of more than one, two, three, four, five, six, seven, eight, nine, ten or more amino acids are deleted from the N-terminus the CD137 intracellular domain as described herein. In some embodiments, the amino acids deleted from the N-terminus the CD137 intracellular domain includes one or more proximal polybasic amino acids of the CD137 intracellular domain.

In some embodiments, the mutant CD137 intracellular domain can be a truncated CD137 intracellular domain. In some embodiments, the truncated CD137 intracellular domain comprises an amino acid sequence according to amino acid position 13 to amino acid position 42 of the CD137 intracellular domain, of the present disclosure. In some embodiments, the truncated CD137 intracellular domain comprises a deletion of a continuous stretch of one, two, three, four, five, six, seven, eight, nine, ten or more amino acids from the N-terminus of the CD137 intracellular domain, of the present disclosure. In some embodiments, the truncated CD137 intracellular domain comprises a deletion of one, two, three, four, five, six, seven, eight, nine, ten or more amino acids from amino acid position 1 to amino acid position 12 of the N-terminus of the CD137 intracellular domain, of the present disclosure. In some embodiments, the truncated CD137 intracellular domain comprises a deletion of amino acid position 1 to amino acid position 12 of the N-terminus of the CD137 intracellular domain, of the present disclosure. In some embodiments, the CD137 intracellular domain comprises an amino acid sequence according to SEQ ID NO: 3.

In some embodiments, the mutant CD137 intracellular domain comprises a deletion of one or more proximal basic amino acids from amino acid position 1 to amino acid position 12 of the N-terminus of the CD137 intracellular domain, of the present disclosure. In some embodiments, the mutant CD137 intracellular domain comprises one or more proximal basic amino acid mutation(s) from amino acid position 1 to amino acid position 12 of the N-terminus of the CD137 intracellular domain, of the present disclosure. In some embodiments, the mutant CD137 intracellular domain comprises one or more proximal basic amino acid mutation(s) at amino acid positions selected from amino acid positions 1, 2, 3, 4, 5 and 6 of the N-terminus of the CD137 intracellular domain, of the present disclosure. In some embodiments, the mutant CD137 intracellular domain comprising one or more proximal basic amino acid mutation(s) of the present disclosure, further comprises a lysine mutation at amino acid position 12 of the N-terminus of the CD137 intracellular domain, of the present disclosure. In some embodiments, the lysine mutation is a lysine to alanine mutation, e.g., K12A. In some embodiments, the CD137 intracellular domain comprises an amino acid sequence according to SEQ ID NO: 3. In some embodiments, the truncated CD137 intracellular domain comprises an amino acid sequence according to SEQ ID NO: 3. In some embodiments, the truncated CD137 intracellular domain comprises an amino acid sequence having at least 50%, 55%, 60%, 65%, 70%, 75%, 80%, 85%, 90%, 95%, 97% or 99% identity to SEQ ID NO: 3.

In some embodiments, the second signal transduction domain of the BCMA-CAR disclosed herein comprises a truncated CD137 intracellular domain comprising an amino acid sequence according to SEQ ID NO: 3. In some embodiments, the second signal transduction domain of the BCMA-CAR disclosed herein is a truncated CD137 intracellular domain comprising an amino acid sequence having at least 50%, 55%, 60%, 65%, 70%, 75%, 80%, 85%, 90%, 95%, 97% or 99% identity to according to SEQ ID NO: 3.

CD3ζ Domain

In some embodiments of the BCMA-CAR disclosed herein, the third signal transduction domain is derived from a CD3 domain.

In some embodiments, the third signal transduction domain of the BCMA-CAR disclosed herein is a truncated CD3 domain comprising an amino acid sequence according to SEQ ID NO: 4. In some embodiments, the third signal transduction domain of the BCMA-CAR disclosed herein, the third signal transduction domain of the BCMA-CAR disclosed herein is a truncated CD3 domain comprising an amino acid sequence having at least 50%, 55%, 60%, 65%, 70%, 75%, 80%, 85%, 90%, 95%, 97% or 99% identity to according to SEQ ID NO: 4.

Ribosome Skipping Sequences

In some embodiments, a BCMA-CAR of the disclosure is multicistronic, i.e., comprises more than one distinct polypeptide produced from a single mRNA transcript. Sequences can be multicistronic by using various linkers, e.g., a polynucleotide sequence encoding a first molecule can be linked to a nucleotide sequence encoding a second molecule, e.g., 5' first gene: linker: second gene 3'. A linker can encode a 2A ribosome skipping element, such as P2A. In some embodiments, a P2A linker comprises an amino acid sequence of SEQ ID NO: 16. In certain embodiments, the P2A linker is encoded by a nucleotide sequence comprising SEQ ID NO: 18. Other 2A ribosome skipping elements include, but are not limited to, E2A, T2A, and F2A. Such 2A ribosome skipping elements allow production of separate polypeptides encoded by the first and second genes produced during translation.

Exemplary BCMA-CAR

Exemplary BCMA-CARs of the disclosure and amino acid sequences of the domains are shown in Table 1.

TABLE 1

| Receptor 1 BCMA-CAR domains and amino acid sequences | | |
|---|---|---|
| Domains | Amino Acid Sequence | SEQ ID NO |
| CD8a leader or CD8a signal peptide | MALPVTALLLPLALLLHAARP | SEQ ID NO: 6 |
| BCMA binding domain or BCMA-nanobody | EVQLQASGGGLAQPGGSLRLSCAASGRTFSTYF MAWFRQPPGKGLEYVGGIRWSDGVPHYADSVKG RFTISRDNAKNTVYLQMNSLRAEDTAVYFCASR GIADGSDFGSYGQGTQVTVSS | SEQ ID NO: 8 |
| CD8a hinge | TTTPAPRPPTPAPTIASQPLSLRPEACRPAAGG AVHTRGLDFAC | SEQ ID NO: 7 |
| Extracellular domain (CD8a leader/signal peptide underlined, CD8a hinge in italic, and ICOS extracellular stalk in italic and underlined) | MALPVTALLLPLALLLHAARPEVQLQASGGGLA QPGGSLRLSCAASGRTFSTYFMAWFRQPPGKGL EYVGGIRWSDGVPHYADSVKGRFTISRDNAKNT VYLQMNSLRAEDTAVYFCASRGIADGSDFGSYG QGTQVTVSS*TTTPAPRPPTPAPTIASQPLSLRP EACRPAAGGAVHTRGLDFAC*SQLCCQLK | SEQ ID NO: 1 |
| Partial ICOS extracellular stalk region | SQLCCQLK | SEQ ID NO: 9 |
| ICOS transmembrane domain | FWLPIGCAAFVVVCILGCILI | SEQ ID NO: 10 |
| ICOS intracellular domain | CWLTKKKYSSSVHDPNGEYMFMRAVNTAKKSRL TDVTL | SEQ ID NO: 2 |
| Truncated CD137 (4-1BB) intracellular domain | QPFMRPVQTTQEEDGCSCRFPEEEEGGCEL | SEQ ID NO: 3 |
| Truncated CD3ζ domain | RVKFSRSADAPAYQQGQNQLYNELNLGRREEYD VLDKRRGRDPEMGGK | SEQ ID NO: 4 |
| Receptor 1 BCMA-CAR full sequence (also referred to as NPB5005-ICOSBBtZt) | MALPVTALLLPLALLLHAARPEVQLQASGGGLA QPGGSLRLSCAASGRTFSTYFMAWFRQPPGKGL EYVGGIRWSDGVPHYADSVKGRFTISRDNAKNT VYLQMNSLRAEDTAVYFCASRGIADGSDFGSYG QGTQVTVSS*TTTPAPRPPTPAPTIASQPLSLRP EACRPAAGGAVHTRGLDFAC*SQLCCQLKFWLPI GCAAFVVVCILGCILICWLTKKKYSSSVHDPNG | SEQ ID NO: 5 |

TABLE 1-continued

Receptor 1 BCMA-CAR domains and amino acid sequences

| Domains | Amino Acid Sequence | SEQ ID NO |
|---|---|---|
| | EYMFMRAVNTAKKSRLTDVTLQPFMRPVQTTQE EDGCSCRFPEEEEGGCELRVKFSRSADAPAYQQ GQNQLYNELNLGRREEYDVLDKRRGRDPEMGGK | |

In some embodiments, the BCMA-CAR of the present disclosure is encoded by the following nucleotide sequence ("clinical vector format").

(SEQ ID NO: 11)
ATGGCTCTGCCTGTGACAGCTCTGCTGCTGCCTCTGGCTCTGCTTCTGC

ATGCCGCTAGACCTGAAGTGCAGTTGCAGGCTTCTGGCGGAGGACTTGC

TCAACCTGGCGGAAGCCTGAGACTGTCTTGTGCCGCCTCTGGCAGAACC

TTCAGCACCTACTTCATGGCCTGGTTCAGACAGCCTCCTGGCAAAGGCC

TGGAATACGTTGGCGGAATCCGTTGGAGTGATGGCGTGCCACACTACGC

CGATAGCGTGAAGGGCAGATTCACCATCAGCCGGGACAACGCCAAGAAC

ACCGTGTACCTCCAGATGAACAGCCTGAGAGCCGAGGATACCGCCGTGT

ACTTCTGTGCCAGCAGAGGAATCGCCGACGGCAGCGATTTTGGCTCTTA

TGGCCAGGGCACCCAAGTGACCGTGTCCAGCACAACAACCCCTGCTCCT

AGACCTCCTACACCAGCTCCTACAATCGCCAGCCAGCCTCTGTCTCTGA

GGCCAGAGGCTTGTAGACCTGCTGCTGGCGGAGCCGTGCATACAAGAGG

ACTGGATTTCGCCTGCAGCCAGCTGTGCTGTCAGCTGAAGTTCTGGCTG

CCTATCGGCTGCGCCGCCTTTGTGGTTGTGTGTATCCTGGGCTGCATCC

TGATCTGCTGGCTGACCAAGAAAAAGTACAGCAGCAGCGTGCACGACCC

CAACGGCGAGTACATGTTCATGAGAGCCGTGAACACCGCCAAGAAGTCC

AGACTGACCGACGTGACCCTCCAGCCTTTCATGAGGCCTGTGCAGACCA

CACAAGAAGAGGACGGCTGCTCCTGTCGGTTCCCCGAGGAAGAGGAAGG

CGGTTGCGAGCTGAGAGTGAAGTTCAGCAGATCCGCCGACGCTCCTGCC

TATCAGCAGGGCCAAAACCAGCTGTACAACGAGCTGAACCTGGGGAGAA

GAGAAGAGTACGACGTGCTGGACAAGCGGAGAGGCAGAGATCCTGAAAT

GGGCGGCAAATGA

TABLE 2

Control BCMA-CAR domains and corresponding amino acid sequences

| BCMA-CAR | Amino Acid Sequence |
|---|---|
| NPB5005-28Z (SEQ ID NO: 12) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACLFPGPSKPF WVLVVVGGVLACYSLLVTVAFIIFWVRSKRSRLLHSDY MNMTPRRPGPTRKHYQPYAPPRDFAAYRSRVKFSRSAD APAYQQGQNQLYNELNLGRREEYDVLDKRRGRDPEMG GKPQRRKNPQEGLYNELQKDKMAEAYSEIGMKGERRR GKGHDGLYQGLSTATKDTYDALHMQALPPR |
| NPB5005-BBZ (SEQ ID NO: 13) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACDIYIWAPL AGTCGVLLLSLVITLYCKRGRKKLLYIFKQPFMRPVQTT QEEDGCSCRFPEEEEGGCELRVKFSRSADAPAYQQGQN QLYNELNLGRREEYDVLDKRRGRDPEMGGKPQRRKNP QEGLYNELQKDKMAEAYSEIGMKGERRRGKGHDGLYQ GLSTATKDTYDALHMQALPPR |
| NPB5005-ICOSBBZ (SEQ ID NO: 14) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACSQLCCQLK FWLPIGCAAFVVVCILGCILICWLTKKKYSSSVHDPNGE YMFMRAVNTAKKSRLTDVTLKRGRKKLLYIFKQPFMRP VQTTQEEDGCSCRFPEEEEGGCELRVKFSRSADAPAYQQ GQNQLYNELNLGRREEYDVLDKRRGRDPEMGGKPQRR KNPQEGLYNELQKDKMAEAYSEIGMKGERRRGKGHDG LYQGLSTATKDTYDALHMQALPPR |

TABLE 2-continued

Control BCMA-CAR domains and corresponding amino acid sequences

| BCMA-CAR | Amino Acid Sequence |
|---|---|
| NPB5005-ICOSBBtZ (SEQ ID NO: 15) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACSQLCCQLK FWLPIGCAAFVVVCILGCILICWLTKKKYSSSVHDPNGE YMFMRAVNTAKKSRLTDVTLQPFMRPVQTTQEEDGCSC RFPEEEEGGCELRVKFSRSADAPAYQQGQNQLYNELNL GRREEYDVLDKRRGRDPEMGGKPQRRKNPQEGLYNEL QKDKMAEAYSEIGMKGERRRGKGHDGLYQGLSTATKD TYDALHMQALPPR |
| FHVH33_CD8_BBZ (SEQ ID NO: 22) | MALPVTALLLPLALLLHAARPEVQLLESGGGLVQPGGSL RLSCAASGFTFSSYAMSWVRQAPGKGLEWVSSISGSGD YIYYADSVKGRFTISRDISKNTLYLQMNSLRAEDTAVYY CAKEGTGANSSLADYRGQGTLVTVSSFVPVFLPAKPTTT PAPRPPTPAPTIASQPLSLRPEACRPAAGGAVHTRGLDFA CDIYIWAPLAGTCGVLLLSLVITLYCNHRNKRGRKKLLY IFKQPFMRPVQTTQEEDGCSCRFPEEEEGGCELRVKFSRS ADAPAYQQGQNQLYNELNLGRREEYDVLDKRRGRDPE MGGKPQRRKNPQEGLYNELQKDKMAEAYSEIGMKGER RRGKGHDGLYQGLSTATKDTYDALHMQALPPR |
| LCAR-B38M_CD8_BB_Z (SEQ ID NO: 23) | MALPVTALLLPLALLLHAARPQVKLEESGGGLVQAGRS LRLSCAASEHTFSSHVMGWFRQAPGKERESVAVIGWRD ISTSYADSVKGRFTISRDNAKKTLYLQMNSLKPEDTAVY YCAARRIDAADFDSWGQGTQVTVSSGGGGSGGGGSGG GGSGGGGSGGGGSAVQLVESGGGLVQAGDSLRLTCTAS GRAFSTYFMAWFRQAPGKEREFVAGIAWSGGSTAYADS VKGRFTISRDNAKNTVYLQMNSLKSEDTAVYYCASRGI EVEEFGAWGQGTQVTVSSTSTTTPAPRPPTPAPTIASQPL SLRPEACRPAAGGAVHTRGLDFACDIYIWAPLAGTCGVL LLSLVITLYCKRGRKKLLYIFKQPFMRPVQTTQEEDGCS CRFPEEEEGGCELRVKFSRSADAPAYQQGQNQLYNELN LGRREEYDVLDKRRGRDPEMGGKPQRRKNPQEGLYNE LQKDKMAEAYSEIGMKGERRRGKGHDGLYQGLSTATK DTYDALHMQALPPR |
| NPB5005_28_BB_Z (SEQ ID NO: 24) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACLFPGPSKPF WVLVVVGGVLACYSLLVTVAFIIFWVRSKRSRLLHSDY MNMTPRRPGPTRKHYQPYAPPRDFAAYRSKRGRKKLLY IFKQPFMRPVQTTQEEDGCSCRFPEEEEGGCELRVKFSRS ADAPAYQQGQNQLYNELNLGRREEYDVLDKRRGRDPE MGGKPQRRKNPQEGLYNELQKDKMAEAYSEIGMKGER RRGKGHDGLYQGLSTATKDTYDALHMQALPPR |
| NPB5005_28BBt_Z (SEQ ID NO: 25) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACLFPGPSKPF WVLVVVGGVLACYSLLVTVAFIIFWVRSKRSRLLHSDY MNMTPRRPGPTRKHYQPYAPPRDFAAYRSQPFMRPVQT TQEEDGCSCRFPEEEEGGCELRVKFSRSADAPAYQQGQN QLYNELNLGRREEYDVLDKRRGRDPEMGGKPQRRKNP QEGLYNELQKDKMAEAYSEIGMKGERRRGKGHDGLYQ GLSTATKDTYDALHMQALPPR |
| NPB5005_28_OX40t_Z (SEQ ID NO: 26) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACLFPGPSKPF WVLVVVGGVLACYSLLVTVAFIIFWVRSKRSRLLHSDY MNMTPRRPGPTRKHYQPYAPPRDFAAYRSGGGSFRTPIQ EEQADAHSTLARVKFSRSADAPAYQQGQNQLYNELNLG RREEYDVLDKRRGRDPEMGGKPQRRKNPQEGLYNELQ KDKMAEAYSEIGMKGERRRGKGHDGLYQGLSTATKDT YDALHMQALPPR |

TABLE 2-continued

Control BCMA-CAR domains and corresponding amino acid sequences

| BCMA-CAR | Amino Acid Sequence |
| --- | --- |
| NPB5005_ICOS_Z (SEQ ID NO: 27) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACSQLCCQLK FWLPIGCAAFVVVCILGCILICWLTKKKYSSSVHDPNGE YMFMRAVNTAKKSRLTDVTLRVKFSRSADAPAYQQGQ NQLYNELNLGRREEYDVLDKRRGRDPEMGGKPQRRKN PQEGLYNELQKDKMAEAYSEIGMKGERRRGKGHDGLY QGLSTATKDTYDALHMQALPPR |
| NPB5005_ICOS_OX40t_Z (SEQ ID NO: 28) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACSQLCCQLK FWLPIGCAAFVVVCILGCILICWLTKKKYSSSVHDPNGE YMFMRAVNTAKKSRLTDVTLGGGSFRTPIQEEQADAHS TLARVKFSRSADAPAYQQGQNQLYNELNLGRREEYDVL DKRRGRDPEMGGKPQRRKNPQEGLYNELQKDKMAEAY SEIGMKGERRRGKGHDGLYQGLSTATKDTYDALHMQA LPPR |
| NPB5005_28_Zt (SEQ ID NO: 29) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACLFPGPSKPF WVLVVVGGVLACYSLLVTVAFIIFWVRSKRSRLLHSDY MNMTPRRPGPTRKHYQPYAPPRDFAAYRSRVKFSRSAD APAYQQGQNQLYNELNLGRREEYDVLDKRRGRDPEMGGK |
| NPB5005_BB_Zt (SEQ ID NO: 30) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACDIYIWAPL AGTCGVLLLSLVITLYCKRGRKKLLYIFKQPFMRPVQTT QEEDGCSCRFPEEEEGGCELRVKFSRSADAPAYQQGQN QLYNELNLGRREEYDVLDKRRGRDPEMGGK |
| NPB5005_28_BBt_Zt (SEQ ID NO: 31) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACLFPGPSKPF WVLVVVGGVLACYSLLVTVAFIIFWVRSKRSRLLHSDY MNMTPRRPGPTRKHYQPYAPPRDFAAYRSQPFMRPVQT TQEEDGCSCRFPEEEEGGCELRVKFSRSADAPAYQQGQN QLYNELNLGRREEYDVLDKRRGRDPEMGGK |
| NPB5005_28_OX40t_Zt (SEQ ID NO: 32) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACLFPGPSKPF WVLVVVGGVLACYSLLVTVAFIIFWVRSKRSRLLHSDY MNMTPRRPGPTRKHYQPYAPPRDFAAYRSGGGSFRTPIQ EEQADAHSTLARVKFSRSADAPAYQQGQNQLYNELNLG RREEYDVLDKRRGRDPEMGGK |
| NPB5005_ICOS_OX40t_Zt (SEQ ID NO: 33) | MALPVTALLLPLALLLHAARPEVQLQASGGGLAQPGGS LRLSCAASGRTFSTYFMAWFRQPPGKGLEYVGGIRWSD GVPHYADSVKGRFTISRDNAKNTVYLQMNSLRAEDTAV YFCASRGIADGSDFGSYGQGTQVTVSSTTTPAPRPPTPAP TIASQPLSLRPEACRPAAGGAVHTRGLDFACSQLCCQLK FWLPIGCAAFVVVCILGCILICWLTKKKYSSSVHDPNGE YMFMRAVNTAKKSRLTDVTLGGGSFRTPIQEEQADAHS TLARVKFSRSADAPAYQQGQNQLYNELNLGRREEYDVL DKRRGRDPEMGGK |

In some aspects, provided herein is a BCMA-CAR comprising: (a) an extracellular domain comprising the amino acid sequence of SEQ ID NO: 1; (b) a transmembrane domain; and (c) a chimeric intracellular domain comprising a first, a second and at least a third signal transduction domain, wherein the first signal transduction domain comprises an ICOS intracellular domain according to SEQ ID NO: 2, the second signal transduction domain comprises a truncated CD137 (4-1BB) intracellular domain according to SEQ ID NO: 3, and the at least third signal transduction domain comprises a truncated CD3ζ domain according to SEQ ID NO: 4.

In some embodiments, the BCMA-CAR comprises (a) an extracellular domain comprising the amino acid sequence of SEQ ID NO: 1; (b) a transmembrane domain; and (c) a chimeric intracellular domain comprising a first, a second and a third signal transduction domains, wherein the first signal transduction domain comprises an ICOS intracellular domain according to SEQ ID NO: 2, the second signal transduction domain comprises a truncated CD137 (4-1BB) intracellular domain according to SEQ ID NO: 3, and the third signal transduction domain comprises a truncated CD3ζ domain according to SEQ ID NO: 4.

In some embodiments, the BCMA-CAR comprises: (a) an extracellular domain comprising the amino acid sequence of SEQ ID NO: 1; (b) a transmembrane domain, wherein the transmembrane domain comprises the amino acid sequence of SEQ ID NO: 10; and (c) a chimeric intracellular domain comprising a first, a second and at least a third signal transduction domain, wherein the first signal transduction domain comprises an ICOS intracellular domain according to SEQ ID NO: 2, the second signal transduction domain comprises a truncated CD137 (4-1BB) intracellular domain according to SEQ ID NO: 3, and the at least third signal transduction domain comprises a truncated CD3ζ domain according to SEQ ID NO: 4.

In some embodiments, the BCMA-CAR comprises: (a) an extracellular domain comprising the amino acid sequence of SEQ ID NO: 1; (b) a transmembrane domain, wherein the transmembrane domain comprises the amino acid sequence of SEQ ID NO: 10; and (c) a chimeric intracellular domain comprising a first, a second and a third signal transduction domains, wherein the first signal transduction domain comprises an ICOS intracellular domain according to SEQ ID NO: 2, the second signal transduction domain comprises a truncated CD137 (4-1BB) intracellular domain according to SEQ ID NO: 3, and the third signal transduction domain comprises a truncated CD3ζ domain according to SEQ ID NO: 4.

In some embodiments, the BCMA-CAR comprises an extracellular domain comprising the amino acid sequence of SEQ ID NO: 1. In some embodiments, the BCMA-CAR comprises a transmembrane domain comprising the amino acid sequence of SEQ ID NO: 10. In some embodiments, the BCMA-CAR comprises a first signal transduction domain comprising the amino acid sequence of SEQ ID NO: 2, a second signal transduction domain comprising the amino acid sequence of SEQ ID NO: 3, and a third signal transduction domain comprising the amino acid sequence of SEQ ID NO: 4.

In some embodiments, the BCMA-CAR extracellular domain comprises a signal peptide domain comprising the amino acid sequence of SEQ ID NO: 6. In some embodiments, the extracellular domain comprises a hinge domain comprising the amino acid sequence of SEQ ID NO: 7. In some embodiments, the extracellular domain comprises a BCMA-binding domain comprising the amino acid sequence of SEQ ID NO: 8. In some embodiments, the extracellular domain comprises an ICOS stalk comprising the amino acid sequence of SEQ ID NO: 9. In some embodiments, the BCMA-CAR extracellular domain comprises a signal peptide domain of the amino acid sequence of SEQ ID NO: 6. In some embodiments, the extracellular domain comprises a hinge domain of the amino acid sequence of SEQ ID NO: 7. In some embodiments, the extracellular domain comprises a BCMA-binding domain of the amino acid sequence of SEQ ID NO: 8. In some embodiments, the extracellular domain comprises an ICOS stalk of the amino acid sequence of SEQ ID NO: 9. In some embodiments, the BCMA-CAR comprises an extracellular domain comprising the amino acid sequence of SEQ ID NO: 1. In some embodiments, the BCMA-CAR comprises an extracellular domain of SEQ ID NO: 1.

In some embodiments, the BCMA-CAR comprises the amino acid sequence according to SEQ ID NO: 1. In some embodiments, the BCMA-CAR comprises the amino acid sequence having at least 50%, 55%, 60%, 65%, 70%, 75%, 80%, 85%, 90%, 95%, 9, 7% or 99% identity to SEQ ID NO: 1.

In some embodiments, the BCMA-CAR comprises an amino acid sequence of SEQ ID NO: 5. In some embodiments, the BCMA-CAR comprises an amino acid sequence having at least 50%, 55%, 60%, 65%, 70%, 75%, 80%, 85%, 90%, 95%, 97% or 99% identity to according to SEQ ID NO: 5. In some embodiments, the BCMA-CAR comprises an amino acid sequence having at least 50%, 55%, 60%, 65%, 70%, 75%, 80%, 85%, 90%, 95%, 97% or 99% identity to according to SEQ ID NO: 5, wherein the BCMA-binding domain comprises the amino acid sequence of SEQ ID NO: 8.

Therapeutic Applications

Also provided herein are methods of using a BCMA-CAR of the present disclosure. The therapeutic method can be characterized according to the disease or condition, e.g., cancer, to be treated. The BCMA-CAR of the present disclosure is suitable for use in cancer, e.g., a cancer expressing BCMA.

In some embodiments, the cancer is a soft tissue sarcoma or a bone sarcoma (osteosarcoma). In some embodiments, the cancer is a sarcoma selected from vesicular rhabdomyosarcoma, vesicular soft tissue sarcoma, ameloblastoma, angiosarcoma, chondrosarcoma, chordoma, bright tissue sarcoma, dedifferentiated liposarcoma, Hyperplastic small round cell tumor of connective tissue, embryonic rhabdomyosarcoma, epithelioid fibrosarcoma, epithelioid hemangioendothelioma, epithelioid sarcoma; sensitive neuroblastoma (esthesioneuroblastoma), Ewing sarcoma, extrarenal rhabdomyosarcoma, extraosseous myxoid chondrosarcoma, extraosseous osteosarcoma, fibrosarcoma, giant cell tumor, hemangiopericytoma, infantile fibrosarcoma, inflammatory myofibroblastoma, Kaposi sarcoma, bone smooth muscle sarcoma, liposarcoma, osteosarcoma, malignant fibrous histiocytoma (MFH), malignant fibrous histiocytoma (MFH), malignant mesenchymal tumor, malignant peripheral nerve sheath tumor, mesenchymal chondrosarcoma, myxoid liposarcoma, myxoid inflammatory fibroblastic sarcoma, multiple tumors with perivascular epithelioid cell differentiation, osteosarcoma, extraperiosteal osteosarcoma, tumors with perivascular epithelial cell differentiation, periosteum osteosarcoma, polymorphic liposarcoma, polymorphic rhabdomyosarcoma, PNET/extraosseous Ewing's tumor, rhabdomyosarcoma, small cell osteosarcoma, single fibroids, synovial sarcoma or capillary dilated osteosarcoma.

In some embodiments, the cancer is a carcinoma selected from basal cell carcinoma, squamous cell carcinoma, renal cell carcinoma, ductal carcinoma in situ (DCIS), invasive ductal carcinoma or adenocarcinoma. In some embodiments, the cancer is a carcinoma selected from adenosquamous carcinoma, anaplastic carcinoma, large cell carcinoma, colorectal carcinoma, pancreatic carcinoma, nasopharyngeal carcinoma, or small cell carcinoma.

In some embodiments, the cancer is selected from anal cancer, appendix cancer; cholangiocarcinoma (i.e., biliary tract cancer), breast cancer, bladder cancer, brain tumor, breast cancer, cervical cancer, colon cancer, colorectal cancer, colon polyp, unidentified primary cancer (cup), esophagus cancer, eye cancer, tubal cancer, kidney cancer, liver cancer, lung cancer, medulloblastoma, melanoma, oral cancer, ovarian cancer, prostate cancer, pancreatic cancer, gastric cancer, testicular cancer, laryngeal cancer, thyroid cancer, uterine cancer, vaginal cancer, or vulvar cancer.

In some embodiments, the breast cancer is an invasive breast duct cancer, carcinoma in situ of the duct, invasive lobular carcinoma or lobular carcinoma in situ. In some embodiments, the pancreatic cancer is adenocarcinoma or islet cell carcinoma. In some embodiments, the colorectal cancer is adenocarcinoma. In some embodiments, colonic polyps are associated with familial adenomatous polyposis. In some embodiments, the bladder cancer is transitional cell bladder cancer, squamous cell bladder cancer, or adenocarcinoma. In some embodiments, the lung cancer is non-small cell lung cancer. In some embodiments, the non-small cell lung cancer is adenocarcinoma, squamous cell lung cancer, or large cell lung cancer. In some embodiments, the non-small cell lung cancer is large cell lung cancer. In some embodiments, the lung cancer is small cell lung cancer. In some embodiments, the prostate cancer is adenocarcinoma or small cell carcinoma. In some embodiments, the ovarian cancer is epithelial ovarian cancer. In some embodiments, the cholangiocarcinoma is proximal cholangiocarcinoma or distal cholangiocarcinoma.

In some embodiments, the cancer is any one of the hematological cancers selected from a leukemia, a myeloma, or a lymphoma. In some embodiments, the cancer is a leukemia selected from acute leukemia, acute lymphoblastic leukemia (ALL), acute lymphocytic leukemia, a B cell, T cell or FAB ALL, acute myeloid leukemia (AML), acute myelogenous leukemia, chronic myelocytic leukemia (CML), chronic lymphocytic leukemia (CLL), hairy cell leukemia, acute promyelocytic leukemia (APL), mixed-lineage leukemia (MLL) or myelodysplastic syndrome (MDS).

In some embodiments, the cancer is a myeloma, e.g., a multiple myeloma. In some embodiments, the cancer is a multiple myeloma selected from the hyperdiploid (HMM) or the non-hyperdiploid or hypodiploid subtypes of multiple myeloma. In some embodiments, the multiple myeloma is selected from light chain myeloma, non-secretory myeloma, solitary plasmacytoma, extramedullary plasmacytoma, monoclonal gammopathy of undetermined significance (MGUS), smoldering multiple myeloma (SMM), immunoglobulin D (IgD) myeloma, or immunoglobulin E (IgE) myeloma.

In some embodiments, the cancer is a lymphoma, e.g., a Hodgkin's lymphoma or a non-Hodgkin's lymphoma. In some embodiments, the cancer is a non-Hodgkin's lymphoma. In some embodiments, the cancer is a non-Hodgkin's lymphoma selected from a Small lymphocytic lymphoma (SLL), Lymphoplasmacytic lymphoma, Diffuse large cell lymphoma, Follicle center cell lymphoma, Burkitt's lymphoma, Burkitt-like lymphoma, Mantle cell lymphoma, or Marginal zone B cell lymphoma. In some embodiments, the cancer is a lymphoma, e.g., a Hodgkin's lymphoma. In some embodiments, the cancer is a Hodgkin's lymphoma selected from nodular sclerosis classical Hodgkin lymphoma, lymphocyte-rich classical Hodgkin lymphoma, or lymphocyte-depleted classical Hodgkin lymphoma.

In some embodiments, the cancer is any one of acute leukemia, acute lymphoblastic leukemia (ALL), acute lymphocytic leukemia, B cell, T cell or FAB ALL, acute myeloid leukemia (AML), acute myelogenous leukemia, chronic myelocytic leukemia (CML), chronic lymphocytic leukemia (CLL), hairy cell leukemia, myelodysplastic syndrome (MDS), Hodgkin's lymphoma, Hodgkin's disease, non-Hodgkin's lymphoma, multiple myeloma, colorectal carcinoma, pancreatic carcinoma, nasopharyngeal carcinoma, malignant histiocytosis, paraneoplastic syndrome/hypercalcemia of malignancy, bladder cancer, breast cancer, colorectal cancer, endometrial cancer, head cancer, neck cancer, hereditary nonpolyposis cancer, liver cancer, lung cancer, non-small cell lung cancer, ovarian cancer, pancreatic cancer, prostate cancer, renal cell carcinoma, testicular cancer, adenocarcinomas, sarcomas, malignant melanoma, and hemangioma.

In some embodiments, the extracellular domain of a B cell maturation antigen (BCMA) chimeric antigen receptor (BCMA-CAR) described herein binds to a target with a binding affinity of 1 fM to 100 µM. In some embodiments, the extracellular domain binds to a target with a binding affinity of 1 pM to 100 µM. In some embodiments, the extracellular domain binds to a target with a binding affinity of 1 pM to 10 pM. In some embodiments, the extracellular domain binds to a target with a binding affinity of 10 pM to 50 pM. In some embodiments, the extracellular domain binds to a target with a binding affinity of 10 pM to 100 pM. In some embodiments, the extracellular domain binds to a target with a binding affinity of 100 pM to 500 pM. In some embodiments, the extracellular domain binds to a target with a binding affinity of 500 pM to 1 nM. In some embodiments, the extracellular domain binds to a target with a binding affinity of 1 nM to 10 nM. In some embodiments, the extracellular domain binds to a target with a binding affinity of 10 nM to 100 nM. In some embodiments, the extracellular domain binds to a target with a binding affinity of 100 nM to 500 nM. In some embodiments, the extracellular domain binds to a target with a binding affinity of 500 nM to 1 µM. In some embodiments, the extracellular domain binds to a target with a binding affinity of 1 µM to 10 µM. In some embodiments, the extracellular domain binds to a target with a binding affinity of 1 µM to 5 µM. In some embodiments, the extracellular domain binds to a target with a binding affinity of 5 µM to 7.5 µM. In some embodiments, the extracellular domain binds to a target with a binding affinity of 7.5 µM to 10 µM.

In some aspects, provided herein is also a BCMA CAR comprising: (a) an extracellular domain, wherein the extracellular domain has an amino acid sequence according to SEQ ID NO: 1; (b) a transmembrane domain; and (c) a chimeric intracellular domain comprising a first, a second and at least a third signal transduction domain, wherein the first signal transduction domain comprises an ICOS intracellular domain according to SEQ ID NO: 2, the second signal transduction domain comprises a truncated CD137 (4-1BB) intracellular domain according to SEQ ID NO: 3, and the at least third signal transduction domain comprises a truncated CD3ζ domain according to SEQ ID NO: 4. In some embodiments, the BCMA-CAR comprises an amino acid sequence according to SEQ ID NO: 5.

In some aspects, the present disclosure also provides a nucleic acid encoding the BCMA-CAR of the present disclosure. The present disclosure also provides a vector, e.g., an expression vector, comprising the nucleic acid of the present disclosure. In some embodiments, the nucleic acid or vector comprises SEQ ID NO:11. The present disclosure also provides a cell, e.g., an isolated cell, comprising the nucleic acid or the vector of the present disclosure. In some embodiments, the cell comprises a nucleic acid or vector comprising SEQ ID NO:11.

Expression on T Cells

In some embodiments, the BCMA-CAR disclosed herein is for expression in a T cell, wherein the T cell co-expresses at least one of the endogenous co-stimulatory molecules CD28, CD2, OX-40, ICOS, CD28, CD3, CD4, CD8, CD40L, or a combination thereof.

In some embodiments, the BCMA-CAR disclosed herein, is co-expressed with a T cell receptor (TCR) in a T cell. In some embodiments, the TCR is an endogenous TCR. In some embodiments, the TCR is an artificial TCR. In some embodiments, the artificial TCR is an affinity enhanced TCR. In some embodiments, the BCMA-CAR when co-expressed with a TCR in a T cell provides a second activation signal for inducing activation and proliferation of the T cell, wherein the first activation signal is provided by antigen binding by the TCR.

In some embodiments, the BCMA-CAR disclosed herein is expressed in a T cell as a component of an artificial receptor for a target. In some embodiments, the artificial receptor is a chimeric antigen receptor (CAR), a receptor for a ligand or a component thereof, an antibody or a fragment thereof. In some embodiments, the BCMA-CAR disclosed herein is expressed as a component of a CAR. In some embodiments, the BCMA-CAR disclosed herein is expressed as a component of an antibody or antigen-binding fragment thereof. In some embodiments, the antibody or antigen-binding fragment thereof is a Fab fragment, a F(ab)$_2$ fragment, a diabody, a nanobody, a sdAb, a Fv, a V$_H$H fragment, or a single chain Fv fragment. In some embodiments, the BCMA-CAR is expressed as a component of an artificial receptor in a T cell as disclosed herein and induces activation and/or proliferation of the T cell upon target binding by the artificial receptor.

In some embodiments, the modified T cell disclosed herein co-expresses at least one of the endogenous co-stimulatory molecules CD28, CD2, OX-40, ICOS, CD28, CD3, CD4, CD8, CD40L or a combination thereof.

In some embodiments, the method disclosed herein further comprises a modification of an endogenous sequence encoding a component of major histocompatibility complex (MHC) class I (MHC-I), wherein the modification reduces or eliminates a level of expression or activity of the MHC-I. In some embodiments, the modification reduces or eliminates the expression or activity of β2-macroglobulin.

The present disclosure also provides a composition comprising a BCMA-CAR disclosed herein. The present disclosure also provides a composition comprising a nucleic acid encoding the BCMA-CAR disclosed herein. The present disclosure also provides a composition comprising a vector comprising a nucleic acid disclosed herein. The present disclosure also provides a composition comprising a cell disclosed herein. The present disclosure also provides a composition comprising a T cell, e.g., a modified T cell, disclosed herein.

The present disclosure also provides a composition comprising a population of cells, wherein the population comprises a plurality of the cell comprising the nucleic acid encoding or a vector comprising the nucleic acid encoding a BCMA-CAR disclosed herein. The present disclosure also provides a composition comprising a population of cells, wherein the population comprises a plurality of the modified T cell disclosed herein.

The present disclosure also provides a method of producing a plurality of modified T cells, wherein the method comprises: a) providing a plurality of primary T cells disclosed herein; b) providing a composition comprising the BCMA-CAR disclosed herein, the nucleic acid encoding the BCMA-CAR disclosed herein, or the vector comprising the nucleic acid encoding the BCMA-CAR disclosed herein; and c) introducing into the plurality of primary T cells of (a) the composition of (b), to produce a plurality of modified T cells under conditions that stably express the BCMA-CAR within the plurality of modified T cells. In some embodiments, the method of producing a plurality of modified T cells disclosed herein, further comprises a step of modifying an endogenous sequence encoding an endogenous T cell Receptor (TCR), wherein the modification reduces or eliminates a level of expression or activity of the endogenous TCR. In some embodiments, the method of producing a plurality of modified T cells disclosed herein, further comprises a step of modifying an endogenous sequence, wherein the modification reduces or eliminates a level of expression or activity of a major histocompatibility complex (MHC) class I (MHC-I).

In some embodiments, the modifying an endogenous sequence encoding a T cell Receptor (TCR) uses a nucleic acid modifying system. In some embodiments, the modifying an endogenous sequence that reduces or eliminates a level of expression or activity uses a nucleic acid modifying system. In some embodiments, the nucleic acid modifying system comprises one or more of a CRISPR/Cas protein, a Transcription Activator-Like Effector Nuclease (TALEN), a Zinc Finger Nuclease (ZFN), and an endonuclease. In some embodiments, the modifying an endogenous sequence is done by nonhomologous end joining repair. In some embodiments, the nonhomologous end joining repair is generated by zinc finger nuclease introduced into the cell, e.g., by physical means, viral vector, or non-viral vector. In some embodiments, the nonhomologous end joining repair is generated by TALE nuclease (i.e., TALEN), introduced into the cell by physical means, viral vector, or non-viral vector. In some embodiments, the modifying an endogenous sequence encoding a T cell Receptor (TCR) reduces or eliminates a level of expression of the alpha chain of the TCR. In some embodiments, the modifying an endogenous sequence encoding a T cell Receptor (TCR) reduces or eliminates a level of expression of beta chain of the TCR. In some embodiments, the modifying an endogenous sequence encoding a T cell Receptor (TCR) reduces or eliminates a level of expression of both the alpha chain and the beta chain TCR alpha chain.

In some embodiments, the modifying an endogenous sequence that reduces or eliminates a level of expression or activity of a major histocompatibility complex (MHC) class I (MHC-I), wherein the modifying of an endogenous sequence reduces or eliminates a level of expression or activity of the MHC-I. In some embodiments, the modifying of an endogenous sequence reduces or eliminates the expression or activity of (32-macroglobulin.

In some embodiments, the method of producing a plurality of modified T cells disclosed herein, further comprises:

d) maintaining or expanding the plurality of modified T cells in a suitable cell culture media; and e) either: i) cryopreserving the plurality of modified T cells in a suitable cell freezing media; or ii) preparing the plurality of modified T cells for administering to a subject suffering from a disease or disorder.

The compositions comprising the cells or modified T cells of the disclosure, and the plurality of modified T cells produced by the methods of the disclosure, intended for administration to a subject may be required to meet one or more "release criteria" that indicate that the composition is safe and efficacious for formulation as a pharmaceutical product and/or administration to a subject. Release criteria may include a requirement that a composition of the disclosure (e.g., a cell or modified T cell of the disclosure) comprises a particular percentage of cells or modified T cells expressing the BCMA-CAR of the disclosure on their cell surface. The expansion process should be continued until a specific criterion has been met (e.g., achieving a certain total number of cells or modified T cells of the disclosure or a certain percentage of total number of cells or modified T cells expressing the BCMA-CAR of the disclosure).

Certain criterion may signal a point at which the expansion process should end. For example, cells should be formulated, reactivated, or cryopreserved once they reach a cell size of 300 fL (otherwise, cells reaching a size above this threshold may start to die). Cryopreservation immediately once a population of cells reaches an average cell size of less than 300 fL may yield better cell recovery upon thawing and culture because the cells have not yet reached a fully quiescent state prior to cryopreservation (a fully quiescent size is approximately 180 fL). Prior to expansion, T cells of the disclosure may have a cell size of about 180 fL but may more than quadruple their cell size (e.g., to approximately 900 fL) at 3 days post-expansion. Over the next 6-12 days of culture, the population of T cells may slowly decrease cell size to full quiescence at 180 fL.

A process for preparing a cell population for formulation may include, but is not limited to the steps of, concentrating the cells of the cell population, washing the cells, and/or further selection of the cells via drug resistance or magnetic bead sorting against a particular surface-expressed marker. A process for preparing a cell population for formulation may further include a sorting step to ensure the safety and purity of the final product. For example, if a tumor cell from a patient has been used to stimulate a modified T cell of the disclosure or that has been modified in order to stimulate a modified T cell of the disclosure that is being prepared for formulation, it is critical that no tumor cells from the patient are included in the final product.

In some embodiments, the cell disclosed herein, or the modified T cell disclosed herein, expresses on the cell surface the BCMA-CAR comprising a mutant CD137 intracellular signaling domain disclosed herein, at a level that is at least about 2×, 3×, 4×, 5×, 6×, 7×, 8×, 9×, 10× or 20×, more as compared to the level of expression of a co-stimulatory molecule comprising a wild type CD137 intracellular domain, respectively.

In some embodiments, the cell disclosed herein further comprises a sequence encoding an artificial antigen receptor, a therapeutic polypeptide, an immune cell modulatory protein, or a combination thereof. In some embodiments, the artificial antigen receptor comprises a chimeric antigen receptor (CAR). In some embodiments, the artificial antigen receptor comprises a recombinant T cell receptor (rTCR). In some embodiments, the artificial antigen receptor comprises an enhanced affinity TCR. In some embodiments, the artificial antigen receptor binds to a tumor associated antigen (TAA), a pathogen associated protein, or an antigen associated with the disease or disorder is a cancer, an autoimmune disease or disorder, an infectious disease, an inflammatory disease, a renal disease or disorder, a lung disease or disorder, a liver disease or disorder a neurodegenerative disorder or disorder, or a metabolic disorder or disorder.

In some embodiments, the artificial antigen receptor binds to a TAA associated with a solid tumor or a hematologic cancer. In some embodiments, artificial antigen receptor binds to a TAA associated with a cancer selected from any one of leukemia, acute leukemia, acute lymphoblastic leukemia (ALL), acute lymphocytic leukemia, B cell, T cell or FAB ALL, acute myeloid leukemia (AML), acute myelogenous leukemia, chronic myelocytic leukemia (CML), chronic lymphocytic leukemia (CLL), hairy cell leukemia, myelodysplastic syndrome (MDS), a lymphoma, Hodgkin's disease, a malignant lymphoma, non-Hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometrial cancer, head cancer, neck cancer, hereditary nonpolyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, and hemangioma.

In some embodiments, the artificial antigen receptor binds to a TAA selected from kallikrein 4, papillomavirus binding factor (PBF), preferentially expressed antigen of melanoma (PRAME), Wilms' tumor-I (WTI), Hydroxysteroid Dehydrogenase Like I (HSDLI), mesothelin, cancer testis antigen (NY-ES0-1), carcinoembryonic antigen (CEA), p53, human epidermal growth factor receptor 2/neuro receptor tyrosine kinase (Her2/Neu), carcinoma-associated epithelial cell adhesion molecule (EpCAM), ovarian and uterine carcinoma antigen (CAI25), folate receptor a, sperm protein 17, tumor-associated differentially expressed gene-12 (TADG-12), mucin-16 (MUC-16), LI cell adhesion molecule (LI-CAM), mannan-MUC-1, Human endogenous retrovirus K (HERV-K-MEL), Kita-kyushu lung cancer antigen-I (KK-LC-1), human cancer/testis antigen (KM-HN-1), cancer testis antigen (LAGE-I), melanoma antigen-A1 (MAGE-A1), Sperm surface zona pellucida binding protein (Spl 7), Synovial Sarcoma, X Breakpoint 4 (SSX-4), Transient axonal glycoprotein-1 (TAG-I), Transient axonal glycoprotein-2 (TAG-2), Enabled Homolog (ENAH), mammoglobin-A, NY-BR-I, Breast Cancer Antigen, (BAGE-1), B melanoma antigen, melanoma antigen-A1 (MAGE-A1), melanoma antigen-A2 (MAGE-A2), mucin k, synovial sarcoma, X breakpoint 2 (SSX-2), Taxol-resistance-associated gene-3 (TRAG-3), Avian Myelocytomatosis Viral Oncogene (c-myc), cyclin B 1, mucin I (MUC I), p62, survivin, lymphocyte common antigen (CD45), DickkopfWNT Signaling Pathway Inhibitor I (DKKI), telomerase, Kirsten rat sarcoma viral oncogene homolog (K-ras), G250, intestinal carboxyl esterase, alpha-fetoprotein, Macrophage Colony-Stimulating Factor (M-CSF), Prostate-specific membrane antigen (PSMA), caspase 5 (CASP-5), Cytochrome C Oxidase Assembly Factor I Homolog (COA-1), 0-linked □-N-acetylglucosamine transferase (OGT), Osteosarcoma Amplified 9, Endoplasmic Reticulum Lectin (OS-9), Transforming Growth Factor Beta Receptor 2 (TGF-betaRII), murine leukemia glycoprotein 70 (gp70), Calcitonin Related Polypeptide Alpha (CALCA), Programmed cell death 1 ligand 1 (CD274), Mouse Double Minute 2Homolog (mdm- 2), alpha-actinin-4, elongation factor 2, Malic Enzyme 1 (MEI), Nuclear Transcription Factor Y Subunit C (NFYC), G Antigen 1,3 (GAGE-1,3), melanoma antigen-A6 (MAGE-A6), cancer testis antigen XAGE-lb, six transmembrane epithelial antigen of the prostate 1 (STEAP1), PAP, prostate specific antigen (PSA), Fibroblast Growth Factor 5 (FGFS), heat shock protein hsp70-2, melanoma antigen-A9 (MAGE-A9), Arg-specific ADP-ribosyltransferase family C (ARTC1), B-Raf Proto-Oncogene (B-RAF), Serine/Threonine Kinase, beta-catenin, Cell Division Cycle 27 homolog (Cdc27), cyclin dependent kinase 4 (CDK4), cyclin dependent kinase 12 (CDK12), Cyclin Dependent Kinase Inhibitor 2A (CDKN2A), Casein Kinase 1 Alpha 1 (CSNK1A1), Fibronectin 1 (FN1), Gruwih Anest Specific 7 (GAS7), Glycoprotein nonmetastatic melanoma protein B (GPNMB), HAUS Augmin Like Complex Subunit 3 (HAUS3), LDLR-fucosyltransferase, Melanoma Antigen Recognized By T cells 2 (MART2), myostatin (MSTN), Melanoma Associated Antigen (Mutated) 1 (MUM-1-2-3), Poly(A) polymerase gamma (neo-PAP), myosin class I, Protein phosphatase 1 regulatory subunit 3B (PPP1R3B), Peroxiredoxin-5 (PRDX5), Receptor-type tyrosine-protein phosphatase kappa (PTPRK), Transforming protein N-Ras (N-ras), retinoblastoma-associated factor 600 (RBAF600), sirtuin-2 (SIRT2), SNRPD1, triosephosphate isomerase, Ocular Albinism Type 1 Protein (OA1), member RAS oncogene family (RAB38), Tyrosinase related protein 1-2 (TRP-1-2), Melanoma Antigen Gp75 (gp75), tyrosinase, Melan-A (MART-1), Glycoprotein 100 melanoma antigen (gp100), N-acetylglucosaminyltransferase V gene (GnTVf), Lymphocyte Antigen 6 Complex Locus K (LY6K), melanoma antigen-AlO (MAGE-AlO), melanoma antigen-Al2 (MAGE-Al2), melanoma antigen-C2 (MAGE-C2), melanoma antigen NA88-A, Taxol-resistant-associated protein 3 (TRAG-3), BDZ binding kinase (pbk), caspase 8 (CASP-8), sarcoma antigen 1 (SAGE), Breakpoint Cluster Region-Abelson oncogene (BCR-ABL), fusion protein in leukemia, dek-can, Elongation Factor Tu GTP Binding Domain Containing 2 (EFTUD2), ETS Variant gene 6/acute myeloid leukemia fusion protein (ETV6-AML1), FMS-like tyrosine kinase-3 internal tandem duplications (FLT3-ITD), cyclin-A1, Fibronectin Type III Domain Containing 3B (FDNC3B,) promyelocytic leukemia/retinoic acid receptor alpha fusion protein (pml-RARalpha), melanoma antigen-Cl (MAGE-Cl), membrane protein alternative spliced isoform (D393-CD20), melanoma antigen-A4 (MAGE-A4), and melanoma antigen-A3 (MAGE-A3).

In some embodiments, the artificial antigen receptor binds to an antigen associated with an autoimmune condition or disorder selected from any one of Type 1 Diabetes, rheumatoid arthritis (RA), systemic lupus erythematosis (SLE), or multiple sclerosis (MS). In some embodiments, the artificial antigen receptor binds to an antigen associated with an autoimmune condition or disorder selected from any one of Carboxypeptidase H, Chromogranin A, Glutamate decarboxylase, Imogen-38, Insulin, Insulinoma antigen-2 and 2β, Islet-specific glucose-6-phosphatase catalytic subunit related protein (IGRP), Proinsulin, α-enolase, Aquaporin-4, β-arrestin, Myelin basic protein, Myelin oligodendrocytic glycoprotein, Proteolipid protein, S100-β, Citrullinated protein, Collagen II, Heat shock proteins, Human cartilage glycoprotein, Double-stranded DNA, La antigen, Nucleosomal histones and ribonucleoproteins (snRNP), Phospholipid-β-2 glycoprotein I complex, Poly(ADP-ribose) polymerase, Sm antigens of U-1 small ribonucleoprotein complex.

In some embodiments, the artificial antigen receptor binds to a pathogen associated antigen from a bacterial, a fungal or a parasitic protein or fragment thereof. In some embodiments, the artificial antigen receptor binds to an antigen associated with HIV infection, human Cytomegalovirus infection, Hepatitis B infection, Hepatitis C infection, Ebola virus infection, Dengue, Yellow fever, Listeriosis, Tuberculosis, Cholera, Malaria, Leishmaniasis, or *Trypanosoma* infection, or a combination thereof.

In some embodiments, the artificial antigen receptor binds to an antigen associated with a neurodegenerative disorder or condition selected from Alzheimer's disease (AD) and other dementias, Parkinson's disease (PD) and PD-related disorders, Prion disease, Motor neuron diseases (MND), Huntington's disease (HD), Spinocerebellar ataxia (SCA) or Spinal muscular atrophy (SMA). In some embodiments, the antigen associated with the neurodegenerative disorder or condition is any one of Amyloid β (Aβ), tau, alpha-synuclein (α-syn), mHTT, or prion PrPsc, or a combination thereof.

In some embodiments, the therapeutic polypeptide is a cytokine, a cytokine receptor, a chemokine, a chemokine receptor, an immunogenic polypeptide, or a cell surface protein that binds to a target on the surface of another cell. In some embodiments, the immune cell modulatory protein is a cytokine, a chemokine, a transcription factor, a protein kinase, a protease, a component, or an adaptor protein of a cell signaling pathway.

In some embodiments, the cell disclosed herein expresses the BCMA-CAR disclosed herein. In some embodiments, the cell disclosed herein expresses the BCMA-CAR disclosed herein stably or transiently. In some embodiments, the cell disclosed herein expresses the BCMA-CAR disclosed herein stably. In some embodiments, the cell disclosed herein expresses the BCMA-CAR disclosed herein transiently.

In some embodiments, the cell disclosed herein co-expresses at least one of the endogenous co-stimulatory molecules CD28, CD2, OX-40, ICOS, CD28, CD3, CD4, CD8, CD40L, or a combination thereof.

The present disclosure also provides a modified T lymphocyte (T cell), comprising: (a) a modification of an endogenous sequence encoding a T cell Receptor (TCR), wherein the modification reduces or eliminates a level of expression or activity of the TCR and/or (b) a recombinant T cell co-stimulatory receptor (RTCR) disclosed herein. In some embodiments, the modification of an endogenous sequence encoding a T cell Receptor (TCR) is carried out using a nucleic acid modifying system. In some embodiments, the nucleic acid modifying system is one or more of a CRISPR/Cas protein, a Transcription Activator-Like Effector Nuclease (TALEN), a Zinc Finger Nuclease (ZFN), and an endonuclease. In some embodiments, the modification of an endogenous sequence encoding a T cell Receptor (TCR) is done by nonhomologous end joining repair. In some embodiments, the nonhomologous end joining repair is generated by zinc finger nuclease, introduced into the cell by physical means, viral vector, or non-viral vector. In some embodiments, the nonhomologous end joining repair is generated by TALE nuclease, introduced into the cell by physical means, viral vector, or non-viral vector. In some embodiments, the modification of an endogenous sequence encoding a T cell Receptor (TCR) reduces or eliminates a level of expression of the alpha chain of the TCR. In some embodiments, the modification of an endogenous sequence encoding a T cell Receptor (TCR) reduces or eliminates a level of expression of beta chain of the TCR. In some embodiments, the modification of an endogenous sequence encoding a T cell Receptor (TCR) reduces or eliminates a level of expression of both the alpha chain and the beta chain TCR alpha chain Pharmaceutical Composition or Formulation In some embodiments, the compositions disclosed herein, and the population of modified T cells produced using the methods disclosed herein, is in the form of a pharmaceutical formulation (or composition). In some embodiments, the pharmaceutical formulation disclosed herein comprises a pharmaceutically acceptable carrier. A pharmaceutical formulation of the disclosure may be distributed into bags for infusion, cryopreservation, and/or storage.

A pharmaceutical formulation of the disclosure may be cryopreserved using a standard protocol and, optionally, an infusible cryopreservation medium. For example, a DMSO free cryopreservant (e.g., CryoSOfree™ DMSO-free Cryopreservation Medium) may be used to reduce freezing-related toxicity. A cryopreserved pharmaceutical formulation of the disclosure may be stored for infusion to a patient at a later date. An effective treatment may require multiple administrations of a pharmaceutical formulation of the disclosure and, therefore, pharmaceutical formulations may be packaged in pre-aliquoted "doses" that may be stored frozen but separated for thawing of individual doses.

A pharmaceutical formulation of the disclosure may be stored at room temperature. An effective treatment may require multiple administrations of a pharmaceutical formulation of the disclosure and, therefore, pharmaceutical formulations may be packaged in pre-aliquoted "doses" that may be stored together but separated for administration of individual doses.

A pharmaceutical formulation of the disclosure may be archived for subsequent re-expansion and/or selection for generation of additional doses to the same patient in the case of an allogenic therapy who may need an administration at a future date following, for example, a remission and relapse of a condition.

As noted above, the disclosure provides for stable formulations, which may comprise a phosphate buffer with saline or a chosen salt, as well as preserved solutions and formulations containing a preservative, or multi-use preserved formulations suitable for pharmaceutical and/or veterinary use, comprising at least one modified cell in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, polymers, or mixtures thereof in an aqueous diluent. Any suitable concentration or mixture can be used as known in the art, such as about 0.0015%, or any range, value, or fraction therein. Non-limiting examples include, no preservative, about m-cresol (e.g., 0.2, 0.3. 0.4, 0.5, 0.9, 1.0%), about 0.1-3% benzyl alcohol (e.g., 0.5, 1.1, 1.5, 1.9, 2.0, 2.5%), about 0.001-0.5% thimerosal (e.g., 0.005, 0.01), about 0.001-2.0% phenol (e.g., 0.05, 0.25, 0.28, 0.5, 0.9, 1.0%), 0.0005-1.0% alkylparaben(s) (e.g., 0.0009, 0.001, 0.002, 0.005, 0.0075, 0.009, 0.01, 0.02, 0.05, 0.075, 0.09, 0.1, 0.2, 0.5, 0.75, 0.9, 1.0%), and the like.

As noted above, in some aspects the disclosure provides an article of manufacture, comprising packaging material and at least one vial comprising a solution of at least one modified cell with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater.

The articles of manufacture of the present disclosure are useful for administration over a period ranging from immediate to twenty-four hours or greater. Accordingly, the presently claimed articles of manufacture offer significant advantages to the patient. Formulations of the disclosure can optionally be safely stored at temperatures of from about 2° C. to about 40° C. and retain the biological activity of the protein for extended periods of time, thus allowing a package label indicating that the solution can be held and/or used over a period of 6, 12, 18, 24, 36, 48, 72, or 96 hours or greater.

The products of the present disclosure can include packaging material. The packaging material provides, in addition to the information required by the regulatory agencies, the conditions under which the product can be used.

In another aspect, the present disclosure also provides a method of treating a disease or disorder, comprising administering to a subject in need thereof a therapeutically effective number of the cell comprising the nucleic acid encoding or the vector comprising the nucleic acid encoding a CAR disclosed herein, a therapeutically effective number of any one of the modified T cell disclosed herein, a therapeutically effective amount of any one of the compositions disclosed herein, or a therapeutically effective number of the plurality of modified T cells produced by the method disclosed herein. A BCMA-CAR as provided herein can be used in a method of treating a disease or disorder expressing BCMA, e.g., a cancer-expressing BCMA.

In some embodiments, the subject is a mammal. In some embodiments, the mammal is any one of a human, a primate, a rodent, a canine, a feline, an ungulate, an equine, and a porcine. In some embodiments, the mammal is a human. In some embodiments, the mammal is a non-human primate. In some embodiments, the disease or disorder is any one of a cancer, an autoimmune disorder, an infectious disease, an inflammatory disease or condition, a renal disease or disorder, a lung disease or disorder, a liver disease or disorder, a cardiovascular system disease or disorder, a neurodegenerative disorder or condition, or a metabolic disorder or condition. In some embodiments, the cancer is a solid tumor or a hematologic cancer. In some embodiments, the infectious disease is caused by a bacterium, a virus, a fungus, a protozoa, or a parasite. In some embodiments, the neurodegenerative disorder or condition is any one of Alzheimer's disease (AD) and other dementias, Parkinson's disease (PD) and PD-related disorders, Prion disease, Motor neuron diseases (MND), Huntington's disease (HD), Spinocerebellar ataxia (SCA) or Spinal muscular atrophy (SMA).

The following examples are provided to better illustrate the present disclosure and are not to be interpreted as limiting the scope of the disclosure. To the extent that specific materials are mentioned, it is merely for purposes of illustration and is not intended to limit the disclosure. One skilled in the art may develop equivalent means or reactants without the exercise of inventive capacity and without departing from the scope of the disclosure.

EXAMPLES

Example 1: Materials and Methods

Media and Cell Lines

DMEM was supplemented with Pen/Strep/Glutamine, 20 mM HEPES, 10 µg/mL Gentamycin and 10% FBS to make complete DMEM. RPMI was supplemented with Pen/Strep/Glutamine, 20 mM HEPES, 10 µg/mL Gentamycin, 10% FBS, and 50 µM 2-ME to make complete RPMI. T cell growth media was made by supplementing complete RPMI with 50 ng/ml IL2, 10 ng/ml IL7, and 10 ng/mL IL15 (Peprotech). X-Vivo 15™ (Lonza®) was supplemented with 1% Human Serum, 20 mM HEPES, Pen/Strep/Glutamine, and 10 µg/mL Gentamycin to make Cytokine Media. Human peripheral blood mononuclear cells (PBMCs) were purchased from iSpecimen® and cultured in complete RPMI. 293FT were purchased from Invitrogen®. K562 and A375 cells were purchased from ATCC® and cultured in complete DMEM.

Plasmids and Cloning

A lentiviral plasmid containing the PGK promoter driving a truncated human EGFR receptor (huEGFRt) followed by the MSCV promoter driving GFP and a subsequent WPRE sequence was ordered from VectorBuilder. Co-stimulatory molecules followed by a P2A sequence were ordered as a single gene block (Invitrogen) and placed in frame with the huEGFRt sequence using NEB® builder homology-based recombination. CAR sequences were constructed from gene block fragments (Invitrogen®) and cloned with NEB® builder downstream of the MSCV promoter following GFP excision. PD-L1_P2A and HLA-A2 were cloned in frame with the huEGFRt and in place of GFP, respectively.

P2A amino acid sequence
(SEQ ID NO: 16)
GSGATNFSLLKQAGDVEENPGP

Human EGFRt amino acid sequence
(Other name: huEGFRt (AA112))
(SEQ ID NO: 17)
MLLLVTSLLLCELPHPAFLLIPRKVCNGIGIGEFKDSLSINATNIKHF

KNCTSISGDLHILPVAFRGDSFTHTPPLDPQELDILKTVKEITGFLLI

QAWPENRTDLHAFENLEIIRGRTKQHGQFSLAVVSLNITSLGLRSLKE

ISDGDVIISGNKNLCYANTINWKKLFGTSGQKTKIISNRGENSCKATG

QVCHALCSPEGCWGPEPRDCVSCRNVSRGRECVDKCNLLEGEPREFVE

NSECIQCHPECLPQAMNITCTGRGPDNCIQCAHYIDGPHCVKTCPAGV

MGENNTLVWKYADAGHVCHLCHPNCTYGCTGPGLEGCPTNGPKIPSIA

TGMVGALLLLLVVALGIGLFM

P2A nucleic acid sequence
(SEQ ID NO: 18)
GGATCCGGCGCCACCAATTTCAGCCTGCTGAAACAGGCTGGCGACGTG

GAAGAGAACCCTGGACCT

Human EGFRt nucleic acid sequence
(SEQ ID NO: 19)
ATGCTGCTGCTGGTTACATCTCTGCTGCTGTGCGAGCTGCCCCATCCT

GCCTTTCTGCTGATCCCCAGAAAAGTGTGCAACGGCATCGGCATCGGA

GAGTTCAAGGACAGCCTGAGCATCAACGCCACCAACATCAAGCACTTC

AAGAACTGCACCAGCATCAGCGGCGACCTGCACATTCTGCCTGTGGCC

TTTAGAGGCGACAGCTTCACCCACACACCTCCACTGGACCCTCAAGAG

CTGGACATCCTGAAAACCGTGAAAGAGATCACCGGATTTCTGTTGATC

CAGGCTTGGCCCGAGAACCGGACAGATCTGCACGCCTTCGAGAACCTG

GAAATCATCAGAGGCCGGACCAAGCAGCACGGCCAGTTTTCTCTGGCT

-continued
GTGGTGTCCCTGAACATCACCAGCCTGGGCCTGAGAAGCCTGAAAGAA

ATCAGCGACGGCGACGTGATCATCTCCGGCAACAAGAACCTGTGCTAC

GCCAACACCATCAACTGGAAGAAGCTGTTCGGCACCAGCGGCCAGAAA

ACAAAGATCATCAGCAACCGGGGCGAGAACAGCTGCAAGGCTACAGGC

CAAGTGTGCCACGCTCTGTGTAGCCCTGAAGGCTGTTGGGGACCCGAG

CCTAGAGATTGCGTGTCCTGTCGGAATGTGTCCCGGGGCAGAGAATGC

GTGGACAAGTGCAATCTGCTGGAAGGCGAGCCCCGCGAGTTCGTGGAA

AACAGCGAGTGCATCCAGTGTCACCCCGAGTGTCTGCCCCAGGCCATG

AACATTACCTGTACCGGCAGAGGCCCCGACAACTGTATTCAGTGCGCC

CACTACATCGACGGCCCTCACTGCGTGAAAACATGTCCTGCTGGCGTG

ATGGGAGAGAACAACACCCTCGTGTGGAAGTATGCCGACGCCGGACAT

GTGTGCCACCTGTGTCACCCTAATTGCACCTACGGCTGTACAGGCCCT

GGCCTGGAAGGCTGTCCAACAAACGGACCTAAGATCCCCTCTATCGCC

ACCGGCATGGTTGGAGCCCTGCTGCTTCTGCTGGTGGTGGCCCTTGGA

ATCGGCCTGTTCATGTGA

HLA-A2 signal peptide nucleic acid sequence
(SEQ ID NO: 20)
ATGGCTGTGATGGCCCCTAGAACACTGGTGCTGCTGCTGTCTGGTGCC

CTGGCTCTGACTCAGACATGGGCC huGMCSF Signal Peptide, nucleic acid sequence
(SEQ ID NO: 21)
ATGCTGCTGCTGGTTACATCTCTGCTGCTGTGCGAGCTGCCCCATCCT

GCCTTTCTGCTGATCCCC

Lentiviral Production and Preparation of Retronectin Plates

VSV pseudotyped lentivirus was produced in 6 well plates. In brief, 293FT were seeded the night before or the day of at $0.9 \times 10^6$ or $1.4 \times 10^6$ cells/well, respectively. Once the cells had adhered and reached at least 80% confluency a mix of lentiviral plasmid, packaging vector (psPAX2) and VSV-G envelope expressing plasmid (PMD2.G) were transfected using lipofectamine 3000 (Invitrogen®), according to the manufacturer's protocol. After 18 hrs, the media was replaced with 3 mLs of fresh DMEM. Viral supernatants were harvested 48 hrs following changing the media and spun down at 1500 RPM to remove 293FT cell/debris. Retronectin was coated on 24 well non-tissue culture treated plates at 20 µg/well in PBS-/- for 2 hrs at 37° C. or overnight at 4° C. Retronectin was removed and washed once with PBS prior to addition of lentiviral supernatant (2 mLs). The plate was then spun at 1500 G for 90 minutes at 32° C. to concentrate viral particles onto the retronectin. Lentiviral supernatant was removed immediately prior to transduction of primary T cells or tumor cells. Alternatively, T cells were transduced with polybrene at 8 µg/mL with a spinfection of 800 G for 2 hrs at 32° C.

T Cell Culture, Transduction, and Isolation

Human PBMCs were activated in T cell growth media with CD3/CD28 microbeads (Invitrogen®) in complete RPMI (100 µl beads/50×10⁶ PBMCs). 48 hrs after activation, activated PBMCs were transferred to Lentiviral-coated Retronectin plates for 48 hrs before being transferred to 6 well plates containing fresh T cell growth media. After an additional 24 hrs in culture, cell transduction was determined by flow cytometry and transduced cells were enriched based on huEGFRt expression. To isolate cells based on EGFR expression, T cells cultures were collected, and activation beads removed. Cells were then stained in 1:100 anti-EGFR-APC antibody in MACS buffer at 4° C. for 30 minutes. Cells were then washed and incubated with anti-APC microbeads (Miltenyi®) for 15-30 minutes at 4° C. Unbound microbeads were then removed by centrifugation and huEGFRt cells were isolated by positive selection on mini-MACS columns. Cells were eluted from the mini-MACS columns and put back into culture in T cell growth media and used within 2 weeks for experiments. To create stable cell lines, cells were collected and transduced as with primary T cells. EGFR selection was performed twice, two weeks apart.

T Cell Stimulation

In the cases where T cells were stimulated with plate bound antibodies, Maxisorp™ Flat-bottom plates (Invitrogen™) were coated with the indicated amount of anti-human CD3 antibody (HIT3a-Biolegend®) in PBS−/− for 2 hrs at 37° C. Plates were washed twice in basal RPMI before use. For the myeloma cell line stimulation, RPMI8226 and U266 cell lines were collected and resuspended in Cytokine media and aliquoted to U-bottom plates. Similarly, A375 cells were plated 1 day prior to the addition of T cells in DMEM in 96 well flat-bottom plates. The media was exchanged prior to the addition of cognate T cells. Following EGFR+ selection, T cells were collected, counted, and resuspended at the appropriate concentration in Cytokine media and distributed to antibody or APC-bearing wells. For RPMI18226 and U266 experiments, anti-CD3 (HIT3a/Biolegend™) was added at the indicated dose following 1-2 hrs of RPMI18226 and U266/T cell interaction at 37° C. In the case where T cell proliferation was to be tracked, T cells were labelled with Violet Tracking Dye (CTV) according to Biolegend™'s protocol prior to the addition to stimulatory plates. Supernatant was collected at 18-36 hours post stimulation to assess cytokine secretion and proliferation/T cell killing was assessed following 96 hours of stimulation.

Cytokine Multiplex Assay

Following collection of T cell supernatants cytokines were measured with the Legendplex™ Multi-Analyte Flow Assay Kit for human Th or Th1 cytokines (Biolegend™) The manufacturer's protocol was followed with the following exceptions: 75 µL T cell supernatant was used to measure cytokines and 2 µL of each reagent was used/well. Secreted cytokines were measured by flow cytometry, and the values were normalized to the maximal response of the control group to combine and analyze multiple experiments and normalize for variability between experiments and donors.

Lentiviral Vector Manufacturing 10 mg of GMP-like transfer plasmid will be produced. The transfer plasmid is to work with third generation packaging system in adherent or suspension HEK293 cells for virus manufacturing. 20-30 liter of GMP lentiviral vector is manufactured at the titer of $10^7$/ml and concentrated to $10^9$/ml.

Mouse Experiments

NSG Mice (8-10 weeks old) were injected intravenously (tail vein) with 3e6 MM.15 cells stably expressing *Gaussia* Luciferase-GFP. After 18-20 days, mice were randomized into groups containing roughly equal mean luciferase counts, and T cells were injected by tail vein at the indicated cell counts. Starting at the time of tumor cell injection, once per week, blood samples were collected and *Gaussia* luciferase levels in the serum were determined by an in vitro luciferase assay. Briefly, 54 of clarified plasma was added induplicate to a 96 well plate. Samples were mixed with *Gaussia* substrate (Coelenterazine, GoldBio #CZ25) according to manufacturer's protocol and measured immediately. For in vivo imaging, animals were imaged following Coelenterazine IP administration. In vitro Luciferase measurements were normalized to measurements taken on day 0 after T cell injection. Animal studies were completed at the Institute of Human Virology at the University of Maryland.

Example 2: Construction of BCMA-CAR

The disclosure herein provides the design of BCMA-CARs comprising a potent BCMA nanobody (Kd=1 nM) driven by the proprietary $3^{rd}$ generation ICOS and modified 4-1BB co-stimulatory signaling domains and a modified CD3 domain (modified 3rd generation BCMA-CAR). FIG. 1 shows a schematic of the structure of an exemplary chimeric antigen receptor comprising BCMA nanobody linked to a chimeric intracellular signaling domain described herein.

Example 3: Targeted Elimination of BCMA-Positive Multiple Myeloma Cell Lines Using Modified $3^{rd}$ Generation BCMA-CAR-T Cells Results in Reduced Cytokine Production Described herein are T cells expressing an exemplary BCMA-CAR of the present disclosure. The disclosure herein provides the design of BCMA CAR molecules and validation of their function on CART cell killing of tumor cell lines in vitro.

Figure 2A:
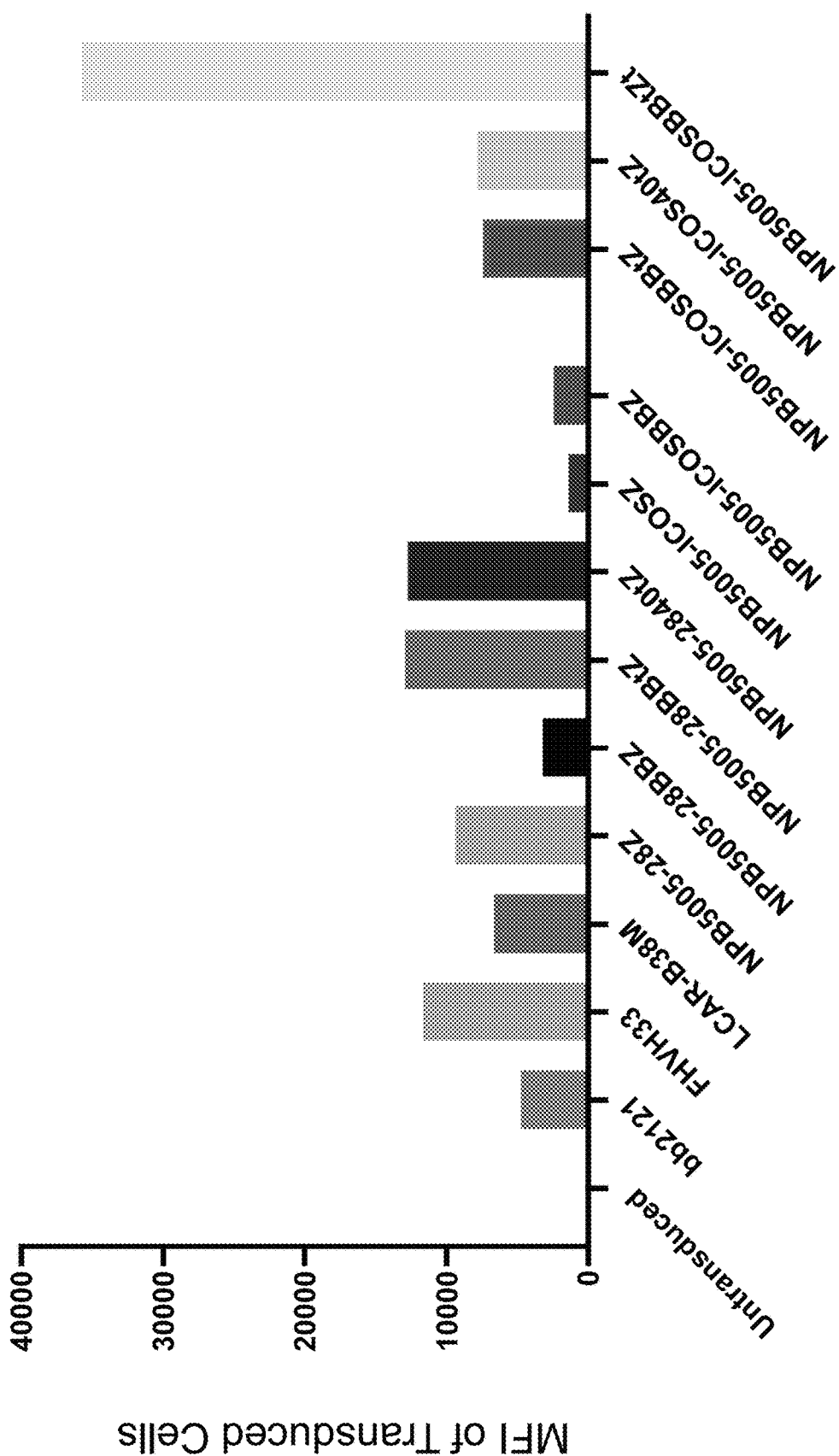
FIGS. 2A-2D show graphs depicting increased CAR surface expression by a BCMA-CAR of the present disclosure ("NPB5005-ICOSBBtZt"), as compared to several exemplary second and third generation CARs utilizing the same extracellular BCMA domain (see Table 2).
Figure 2B:
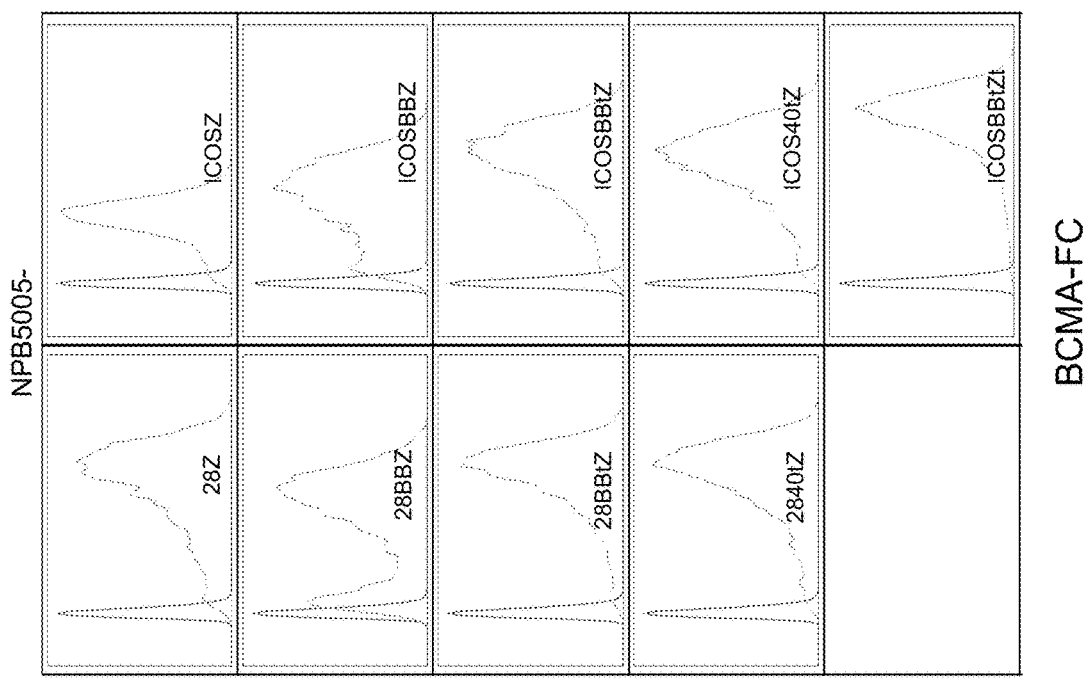
Figure 2C:
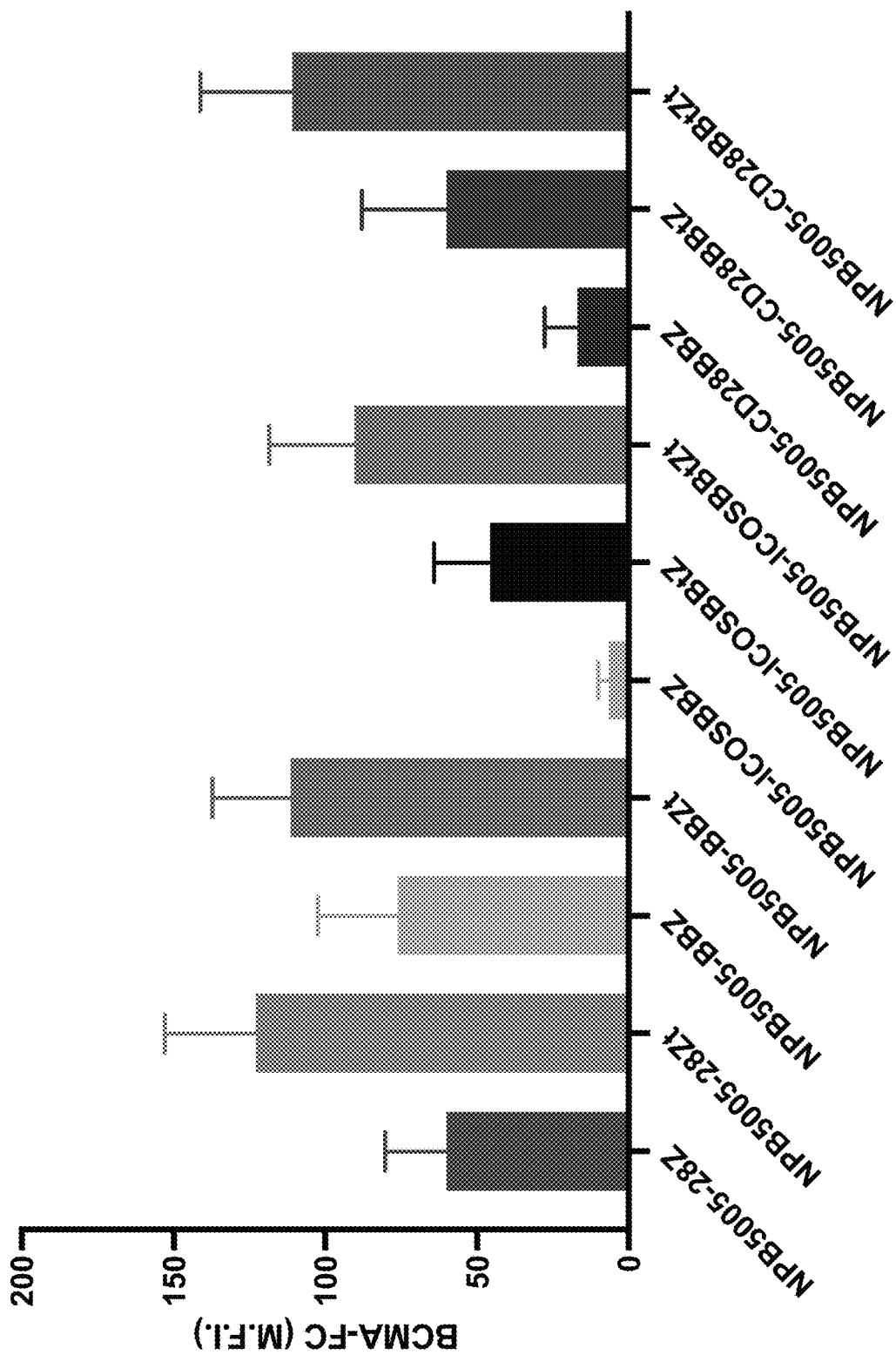
Figure 2D:
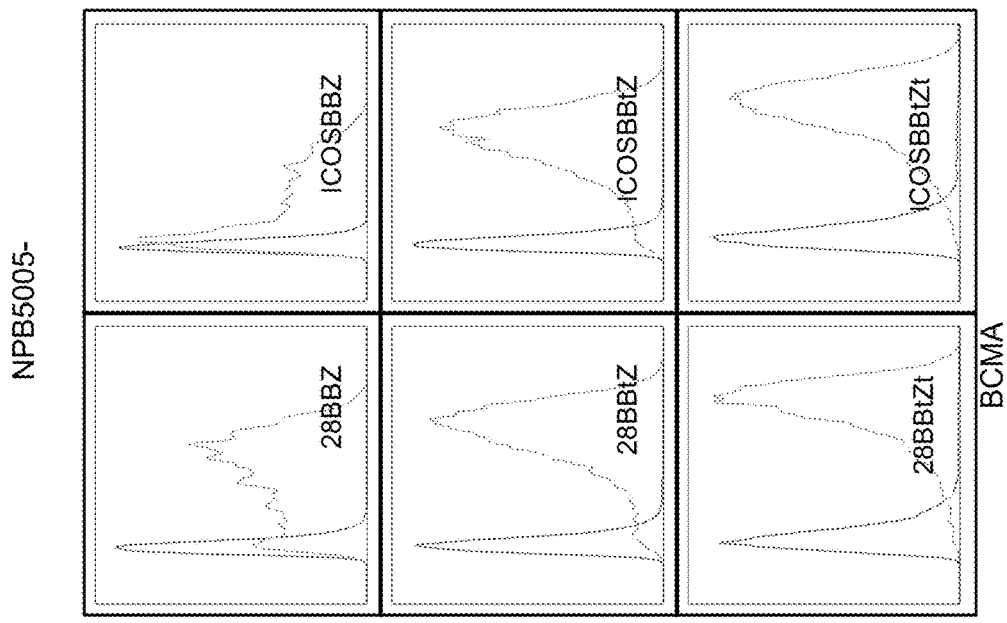
Figure 2D:
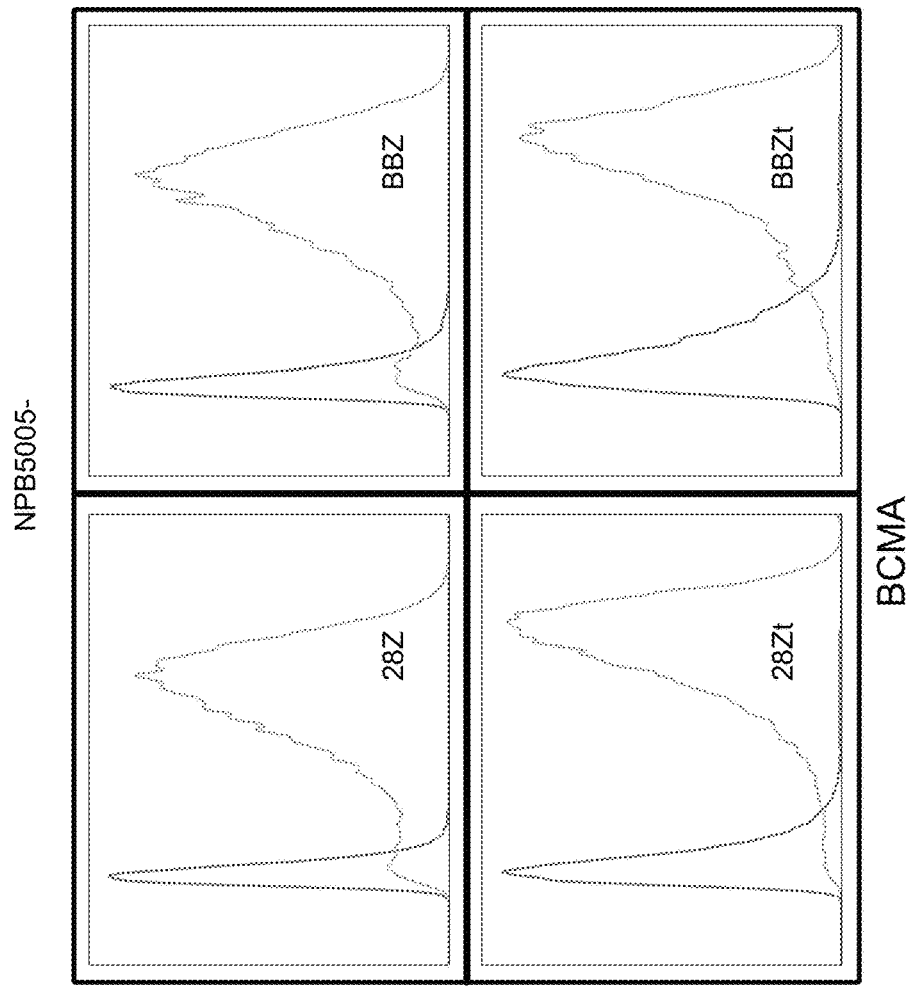

The BCMA-CAR ("Receptor 1" or "NPB5005 BCMA-ICOSBBtZt" or "modified 3rd generation BCMA-CAR") as described in FIG. 1 was introduced into T cells via transduction. As shown in FIGS. 2A-2C, truncation of the CD3Zeta intracellular signaling domain in a BCMA-CAR of the disclosure increased the surface expression of CAR receptors, improving on surface expression gains made by using modified $3^{rd}$ generation CAR receptors (FIG. 2A shows bar graphs of expression and FIG. 2B shows corresponding flow plots). FIG. 2C shows BCMA MFI, demonstrating that the surface expression of both second and third generation receptors benefit from truncation of CD3Zeta, and FIG. 2D shows corresponding flow plots.

Figure 3A:
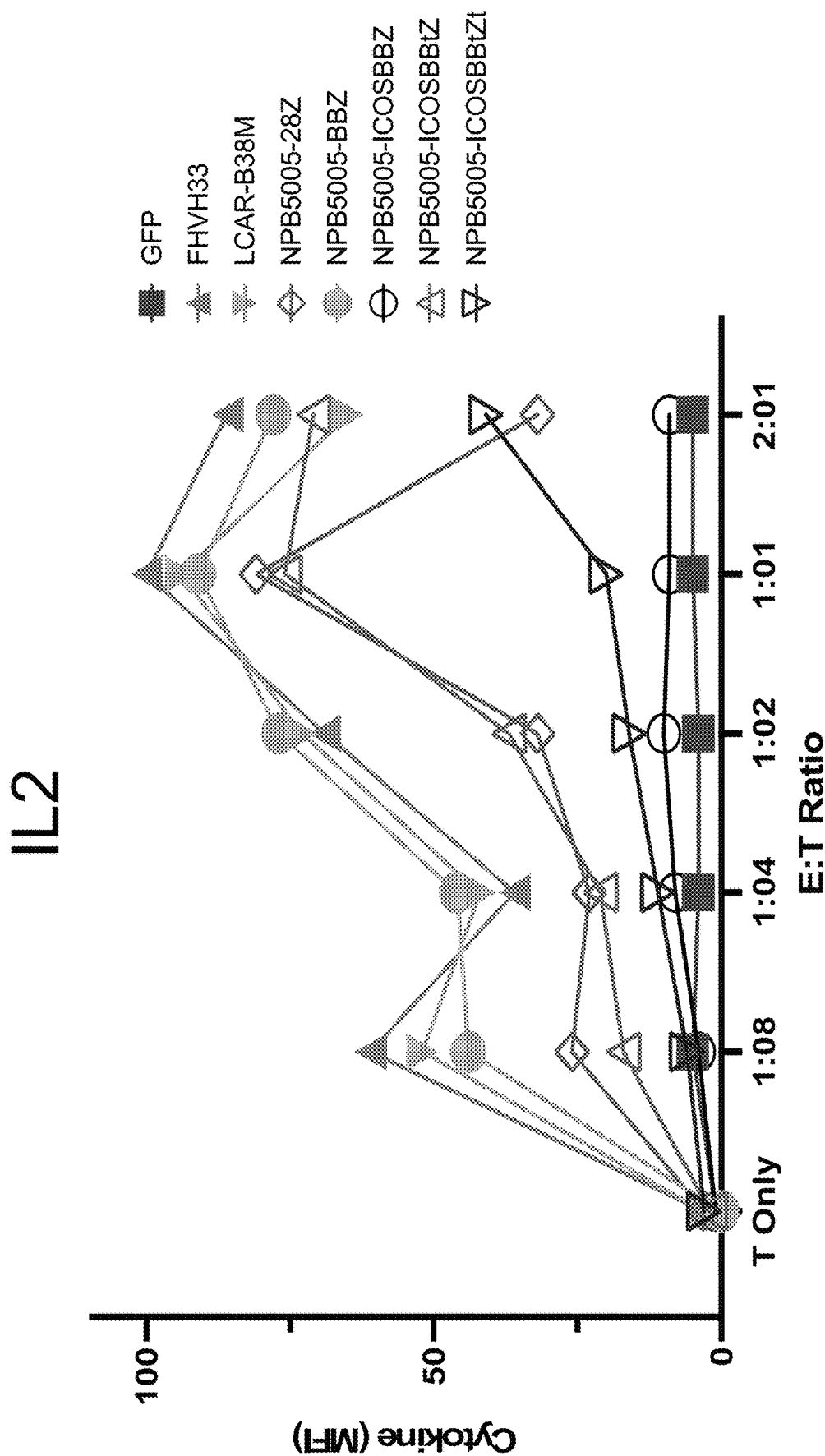
FIGS. 3A-3C show line graphs depicting reduced cytokine production by a BCMA-CAR of the present disclosure ("NPB5005-ICOSBBtZt"), as compared to several exemplary second and third generation CARs utilizing the same extracellular BCMA domain as controls (see Table 2).
Figure 3B:
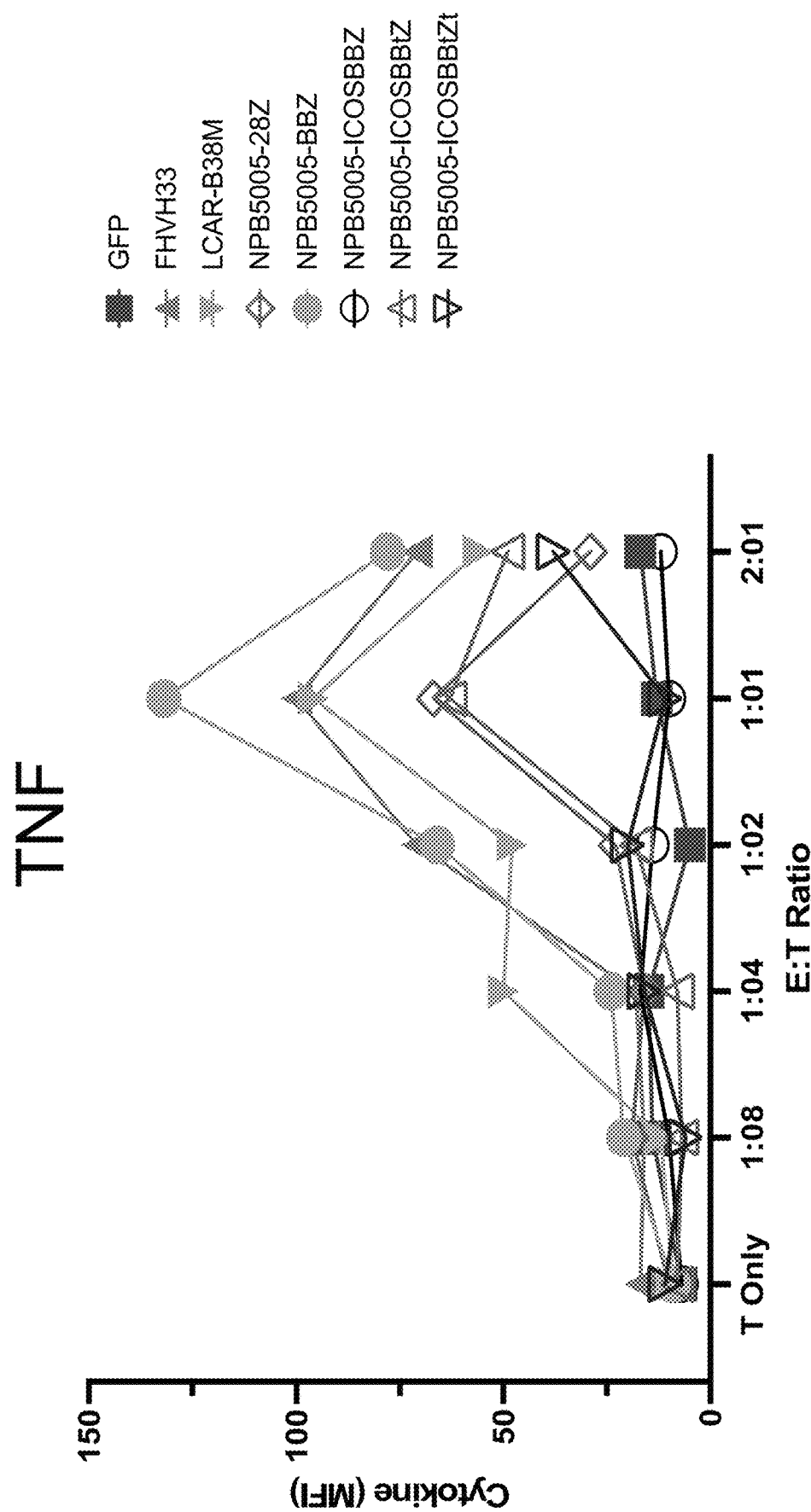
Figure 3C:
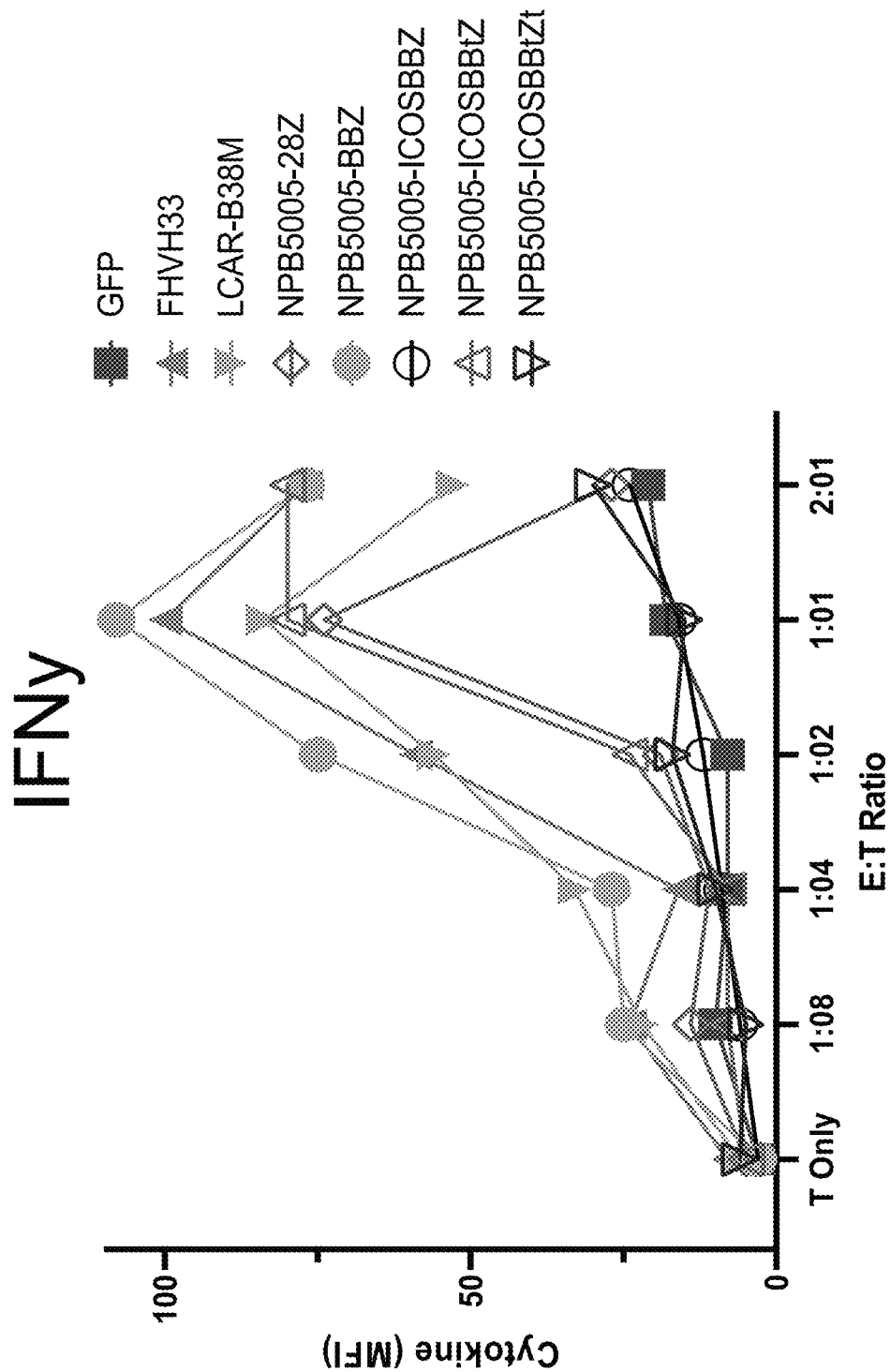

Cytokine production was then assessed. As shown in FIGS. 3A-3C, zeta chain truncation leads to reduced pro-inflammatory cytokine production. IL2 (FIG. 3A), TNFα (FIG. 3B), and IFNγ (FIG. 3C) levels were all reduced, indicating NPB5005-ICOSBBtZt CAR receptor generated less of key inflammatory cytokines relative to the construct with the full-length Zeta intracellular signaling domain and reference constructs.

Figure 4B:
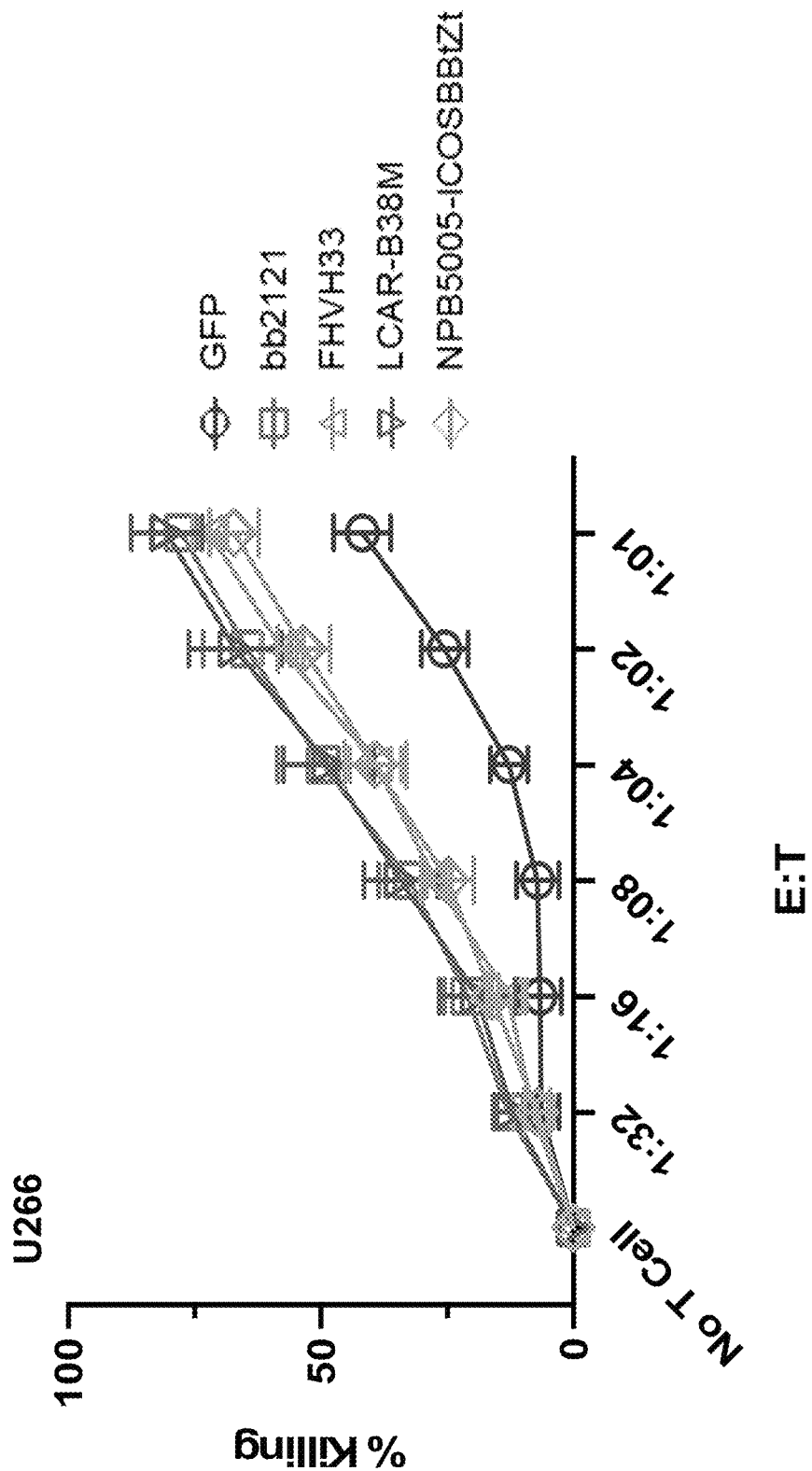
Figure 4C:
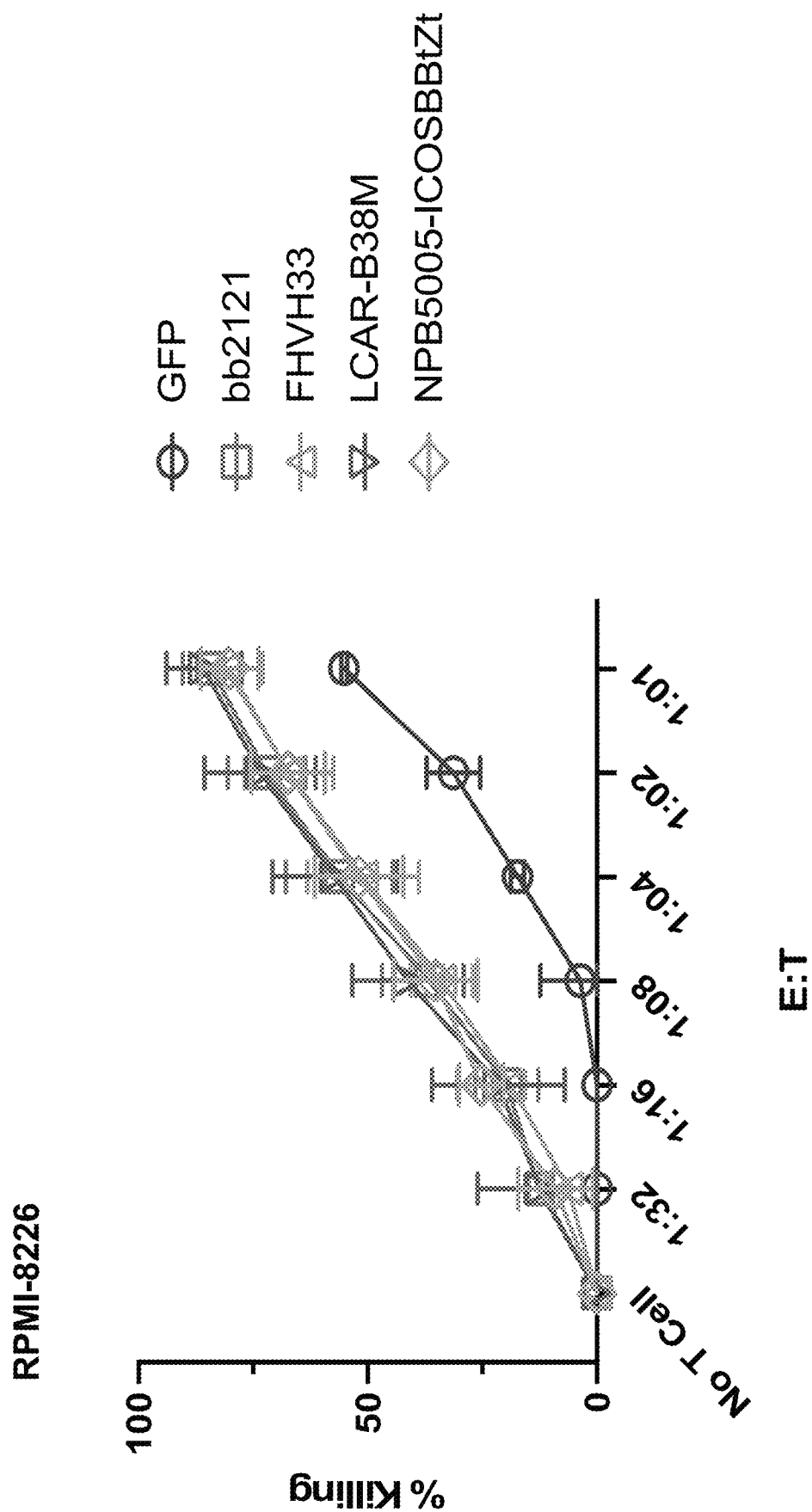

T cells expressing "Receptor 1" were cocultured with multiple myeloma cell lines expressing BCMA, RPMI-8226 and U266, in overnight killing assays to assess the potency of modified $3^{rd}$ generation BCMA-CAR T cell on target tumor cell killing compared to exemplary clinical BCMA CART cell therapies known in the art (bb2121, FHVH33, and LCARB38M) and a GFP control. Target tumor cells included myeloma cell lines expressing BCMA. NPB5005 and control CAR T effector cells (E) were cocultured with target cancer cells (T) at multiple ratios (E:T) from 1:01 to 1:32. The results disclosed herein show that at every ratio tested between 1:01 and 1:32, the modified $3^{rd}$ generation BCMA-CAR T cells killed a similar percentage of MM.15, U266, and RPMI-8225 target cells compared to T cells expressing clinical control CARs (FIGS. 4A-4C, respectively).

The exemplary "Receptor 1" or "NPB5005 BCMA-ICOSBBtZt" as described in FIG. 1 was compared with the reference 2$^{nd}$ generation CAR FHVH33 and with the CARs comprised of the same CD8 leader peptide (SEQ ID NO: 6), BCMA-binding nanobody domain (SEQ ID NO: 8), and CD8 hinge (SEQ ID NO: 7) driven by various 2$^{nd}$ generation or 3$^{rd}$ generation signaling domains and a CD3ζ domain (NPB5005-28Z (SEQ ID NO: 12), NPB5005-BBZ (SEQ ID NO: 13), NPB5005-ICOSBBZ (SEQ ID NO: 14), NPB5005-ICOSBBtZ (SEQ ID NO: 15)) in cytokine production (IL-2, IFNγ and TNF). BCMA-CAR T cells were co-cultured with a BCMA positive cell line, RPMI-8226, at various E:T ratios (1:32, 1:16, 1:08, 1:04, 1:02, 1:01 and 2:01). The amount of IL-2, IFNγ and TNFα released when T cells expressing "NPB5005-ICOSBBtZ" were co-cultured with target cells was lower than the cytokine levels released by T cells expressing 2$^{nd}$ generation BCMA-CARs with identical or different BCMA-binding nanobodies (FIGS. 3A-3C). Compared among 3rd generation BCMA-CARs with the same extracellular domain (SEQ ID NO: 1), T cells expressing "NPB5005-ICOSBBtZ" produce similar or slightly higher cytokines as compared to GFP control, and but significantly lower cytokines than T cells expressing than T cells expressing control CARs (FIGS. 3A-3C).

The results of the study described herein show that exemplary BCMA-CAR T cells of the present disclosure eliminate multiple BCMA-positive cancer cells with equivalent potency compared to leading clinical CAR T cells (FIGS. 4A-4c), while producing significantly less cytokine expression (see FIGS. 3A-3C), reducing toxicity and unwanted side effects for the patient.

Figure 5A:
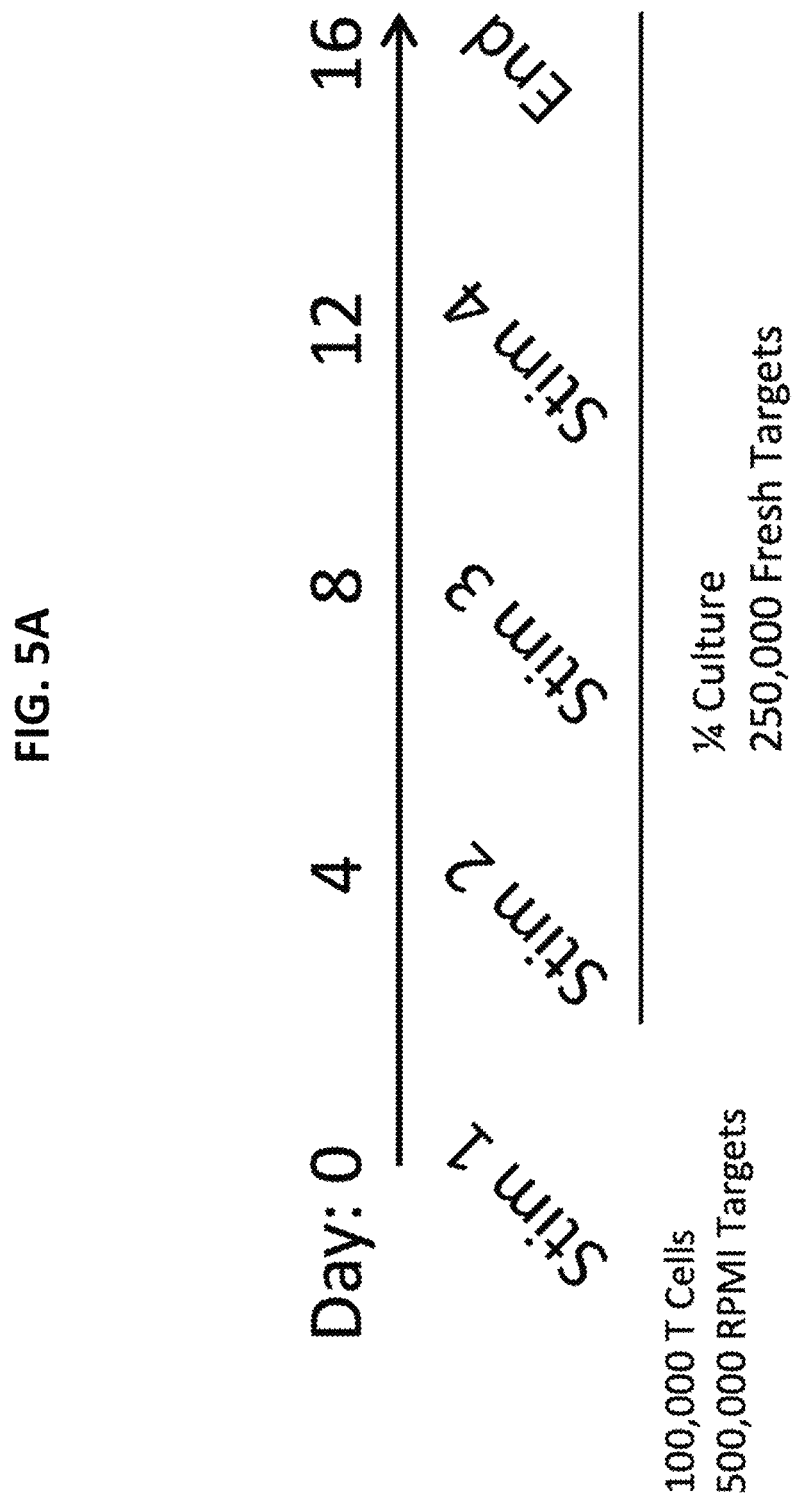
FIGS. 5A-5C depict effects of multiple stimulations by a BCMA-CAR of the present disclosure ("NPB5005-ICOSBBtZt").
Figure 5B:
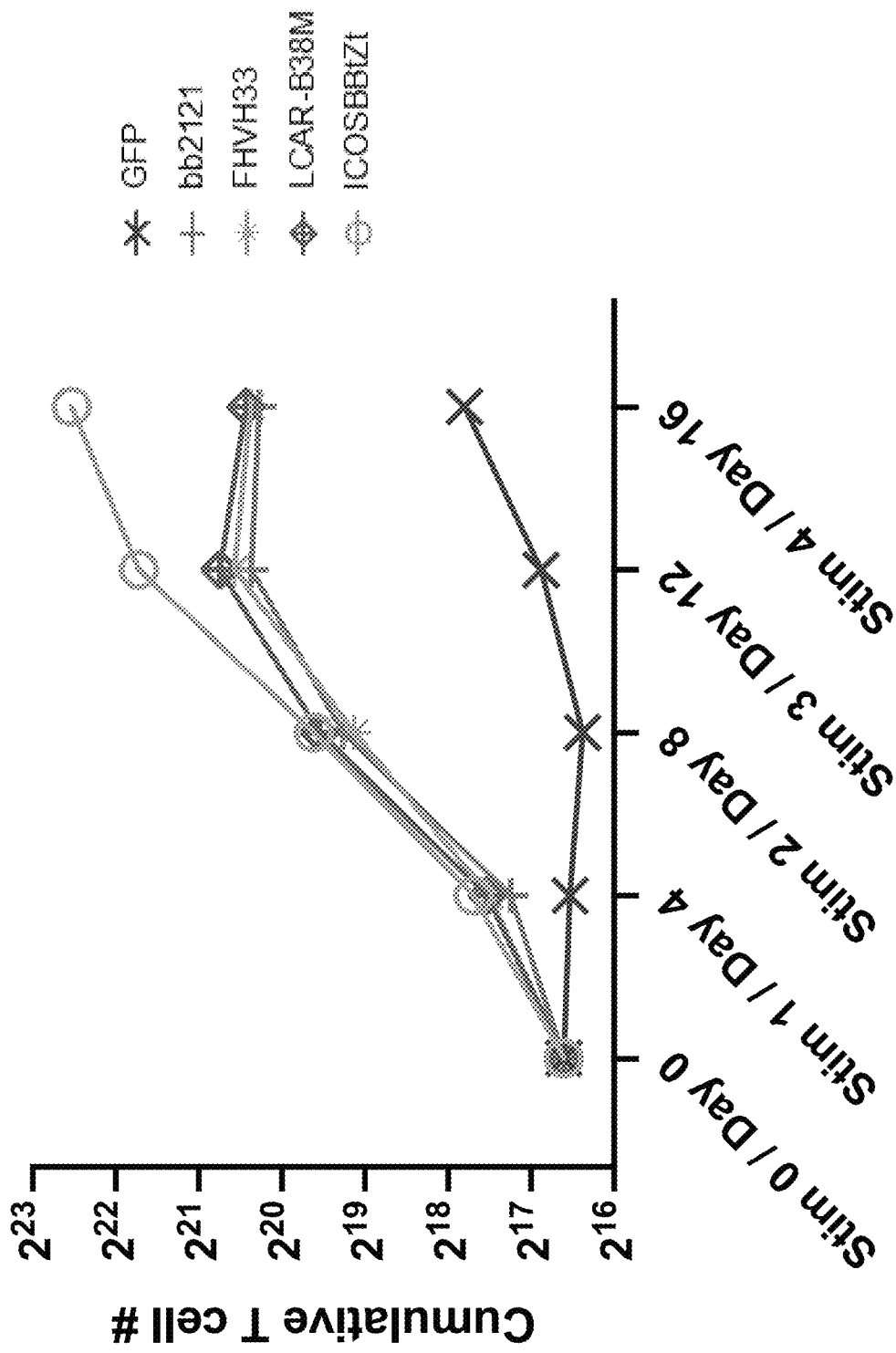
Figure 5C:
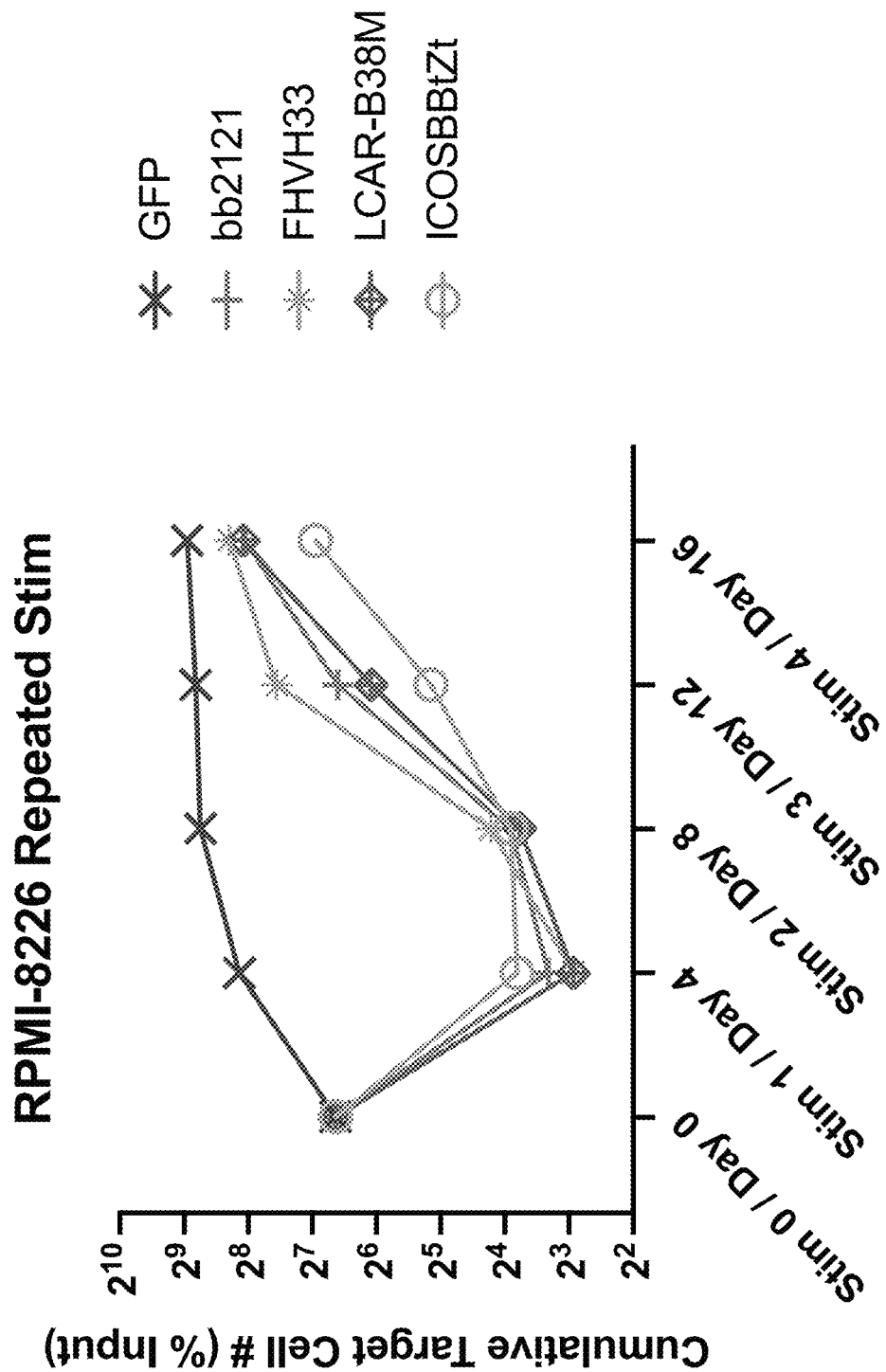

Example 4: BCMA-CAR Eliminates BCMA-Positive Myeloma Cell Lines with Superior Efficacy During Long-Term Repetitive Co-Culture In vitro studies described herein show increased T cell proliferation and persistence by T cells transduced with the modified 3$^{rd}$ generation BCMA-CARs ("Receptor 1" or "NPB5005-ICOSBBtZt") compared to T cells with control clinical CARs (when co-cultured with a BCMA-expressing myeloma cell line, RPMI-8226, based on an exemplary long term repetitive co-culture assay (FIG. 5A). 100,000 CAR T cells were cultured with 500,000 RPMI-8266 cell targets. Cultures were stimulated with 250,000 additional fresh RPMI-8226 target cells every 4 days (on Day 4, Day 8, and Day 12) and cultured for a total of 16 days. FIGS. 5B and 5C show T cell number and target cell number, respectively, at the end of each stimulation, demonstrating enhanced long-term functional cytolytic potential of the NPB5005-ICOSBBtZt CAR construct relative to reference CARs.

Figure 6A:
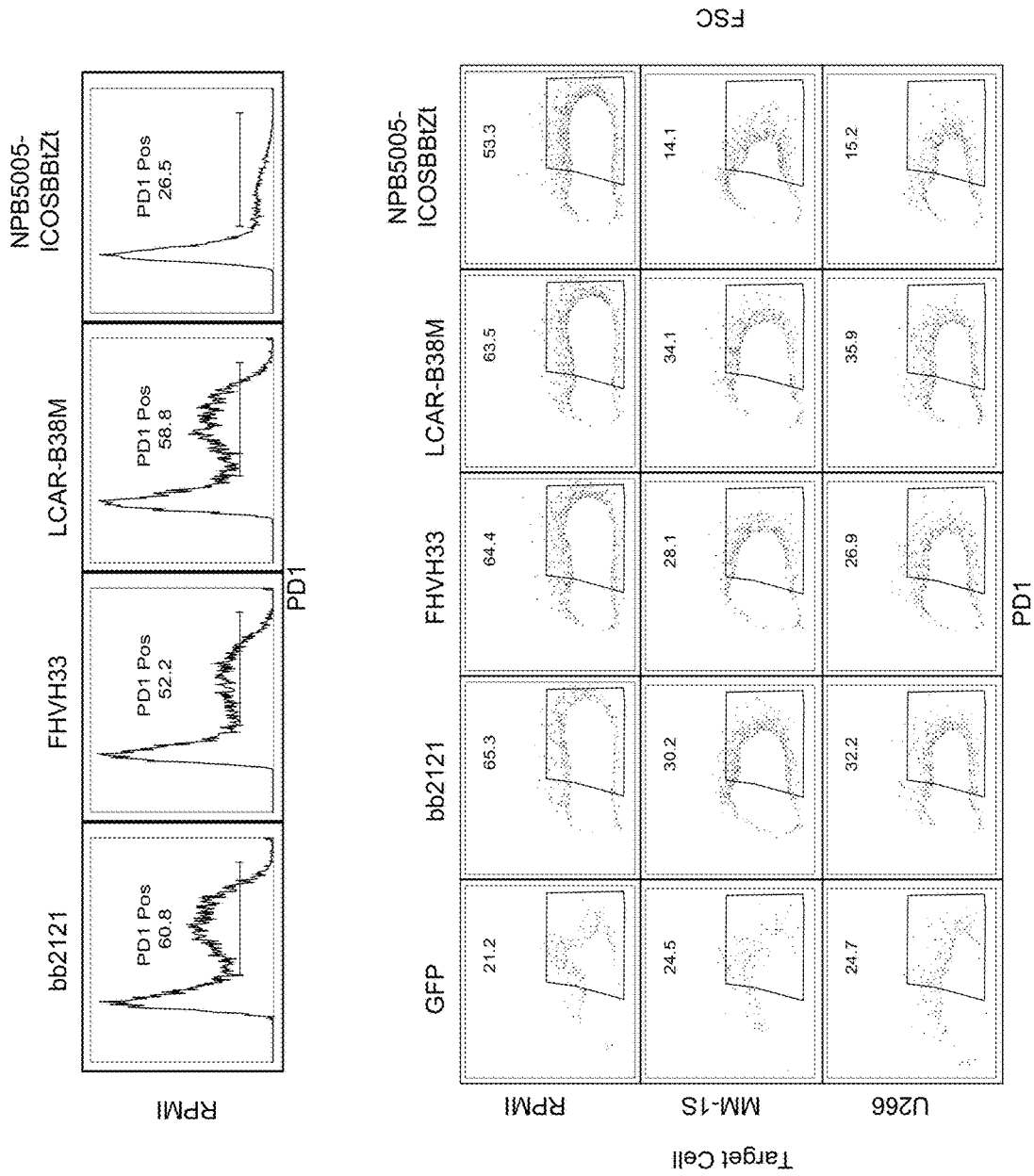
FIGS. 6A-6C shows a series of graphs depicting surface expression of PD-1 on BCMA-CAR T cells of the present disclosure ("NPB5005-ICOSBBtZt") compared to control CAR T cells following the third stimulation with target cells in the exemplary model depicted in FIG. 5.
Figure 6B:
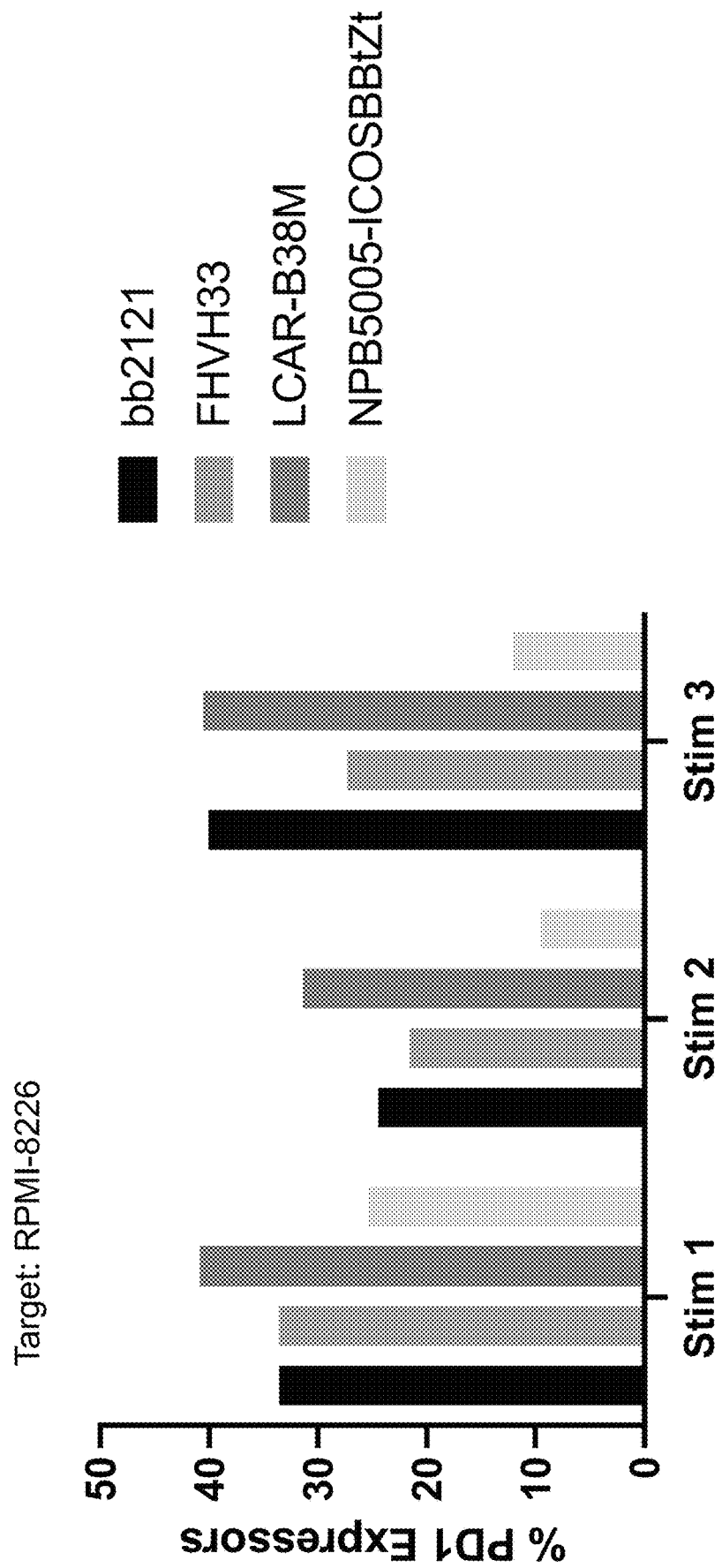
Figure 6C:
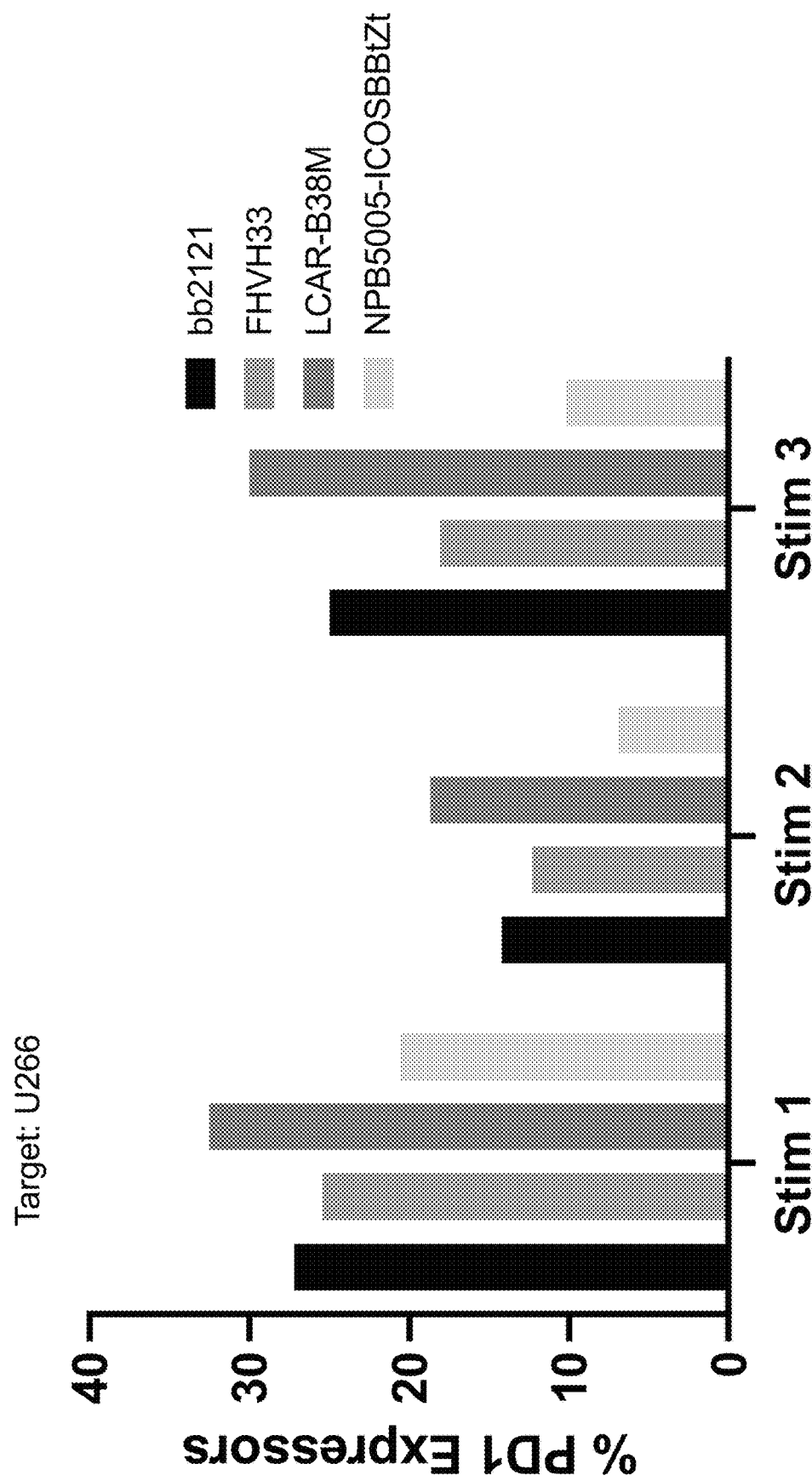
Figure 7A:
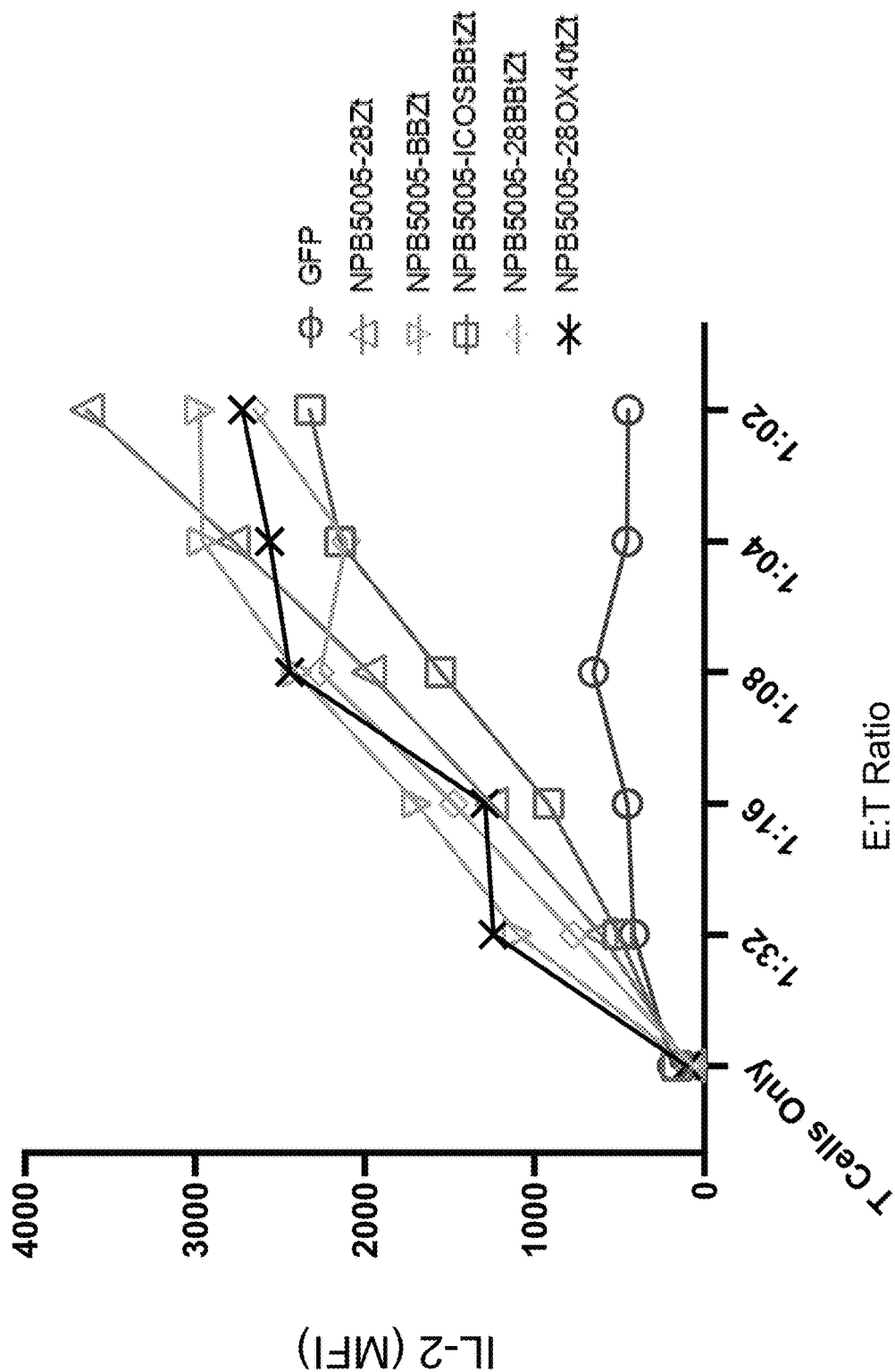
FIGS. 7A-7B are line graphs depicting functionality of a BCMA-CAR of the present disclosure ("NPB5005-ICOSBBtZt").
Figure 7B:
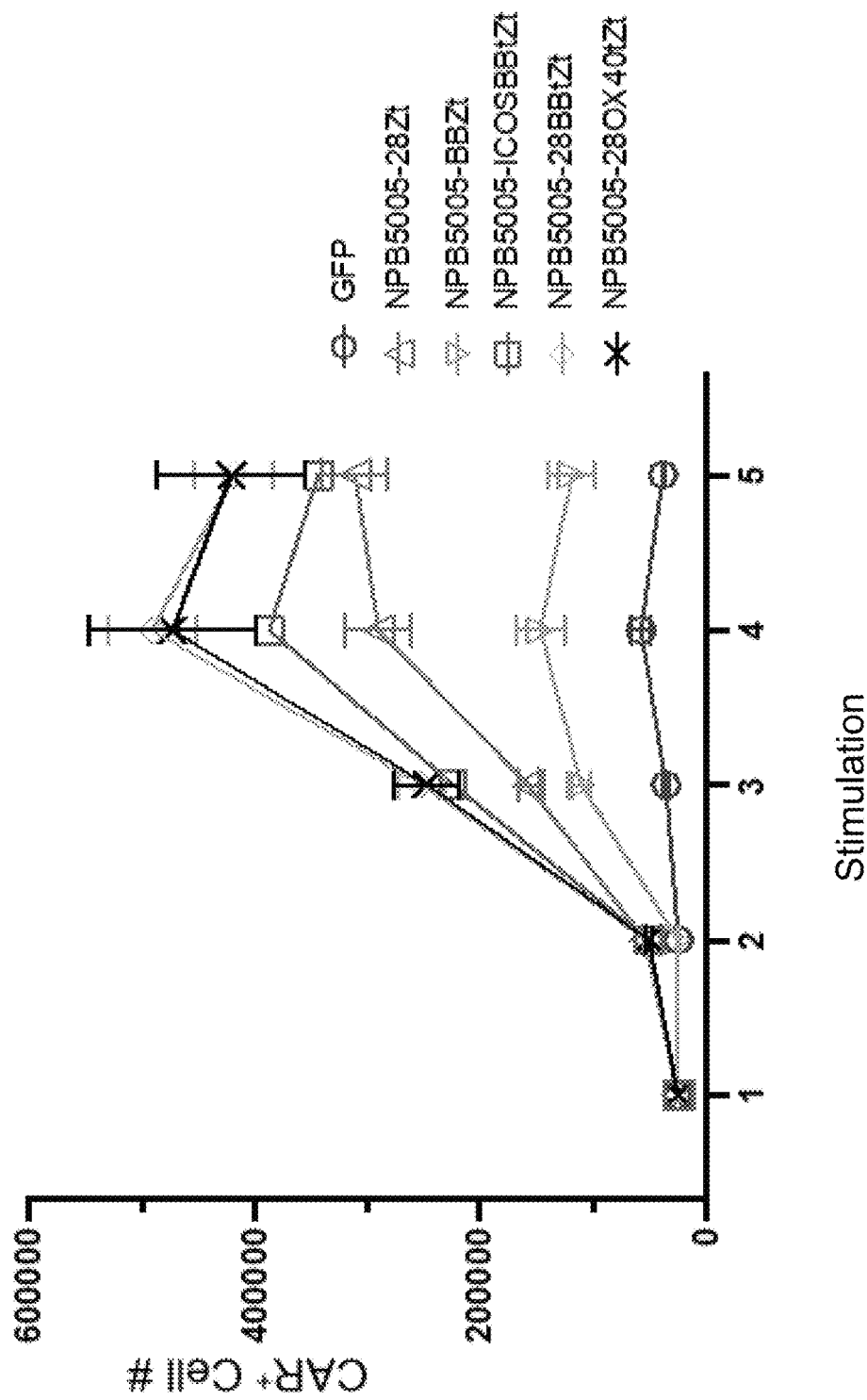
Figure 8A:
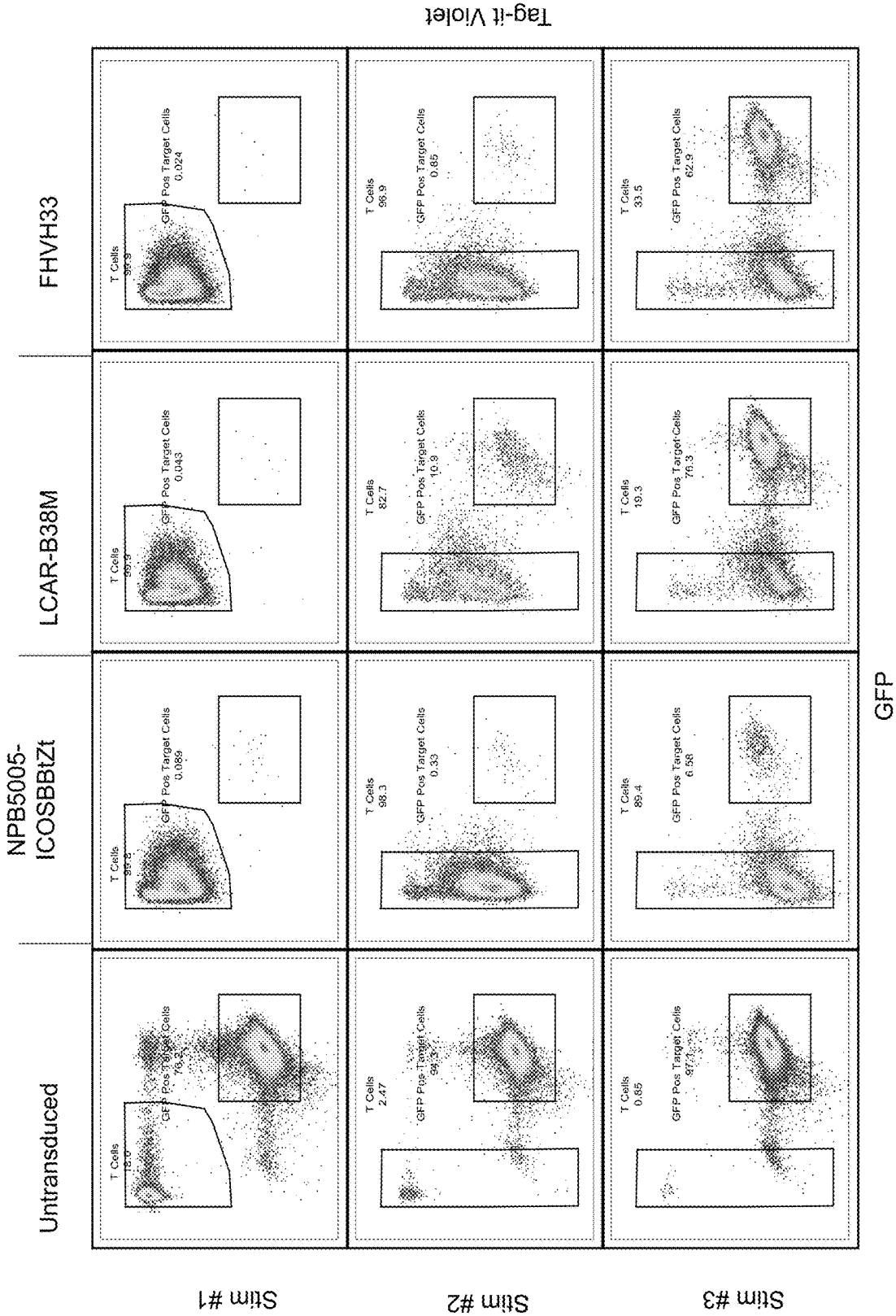
FIGS. 8A-8D depict the proliferative and cytolytic properties of a BCMA-CAR of the present disclosure ("NPB5005-ICOSBBtZt") are maintained in clinical vector format, which lacks a eukaryotic selection marker.
Figure 8B:
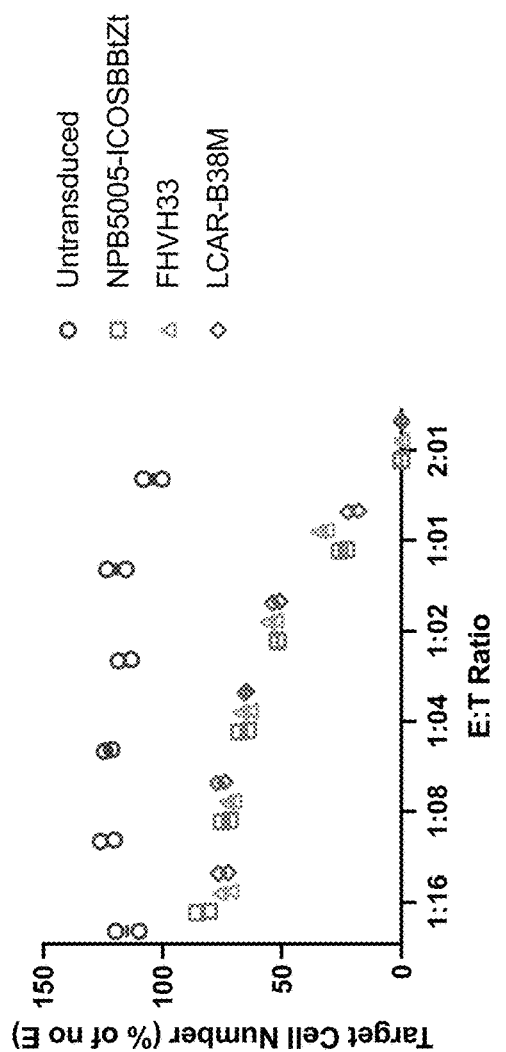
Figure 8B:
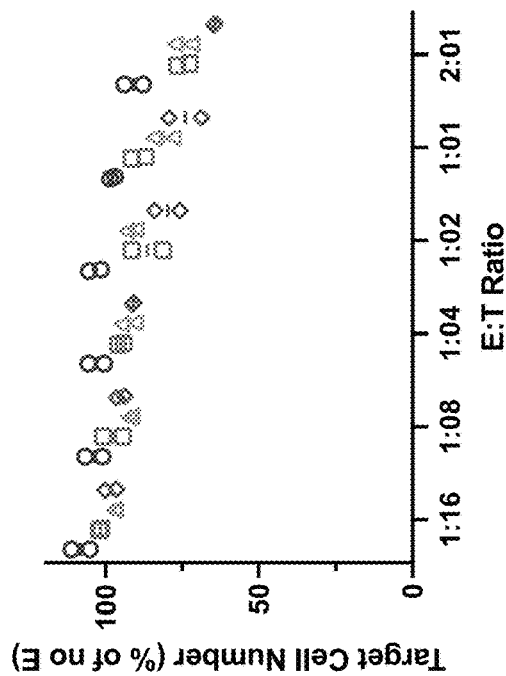
Figure 8C:
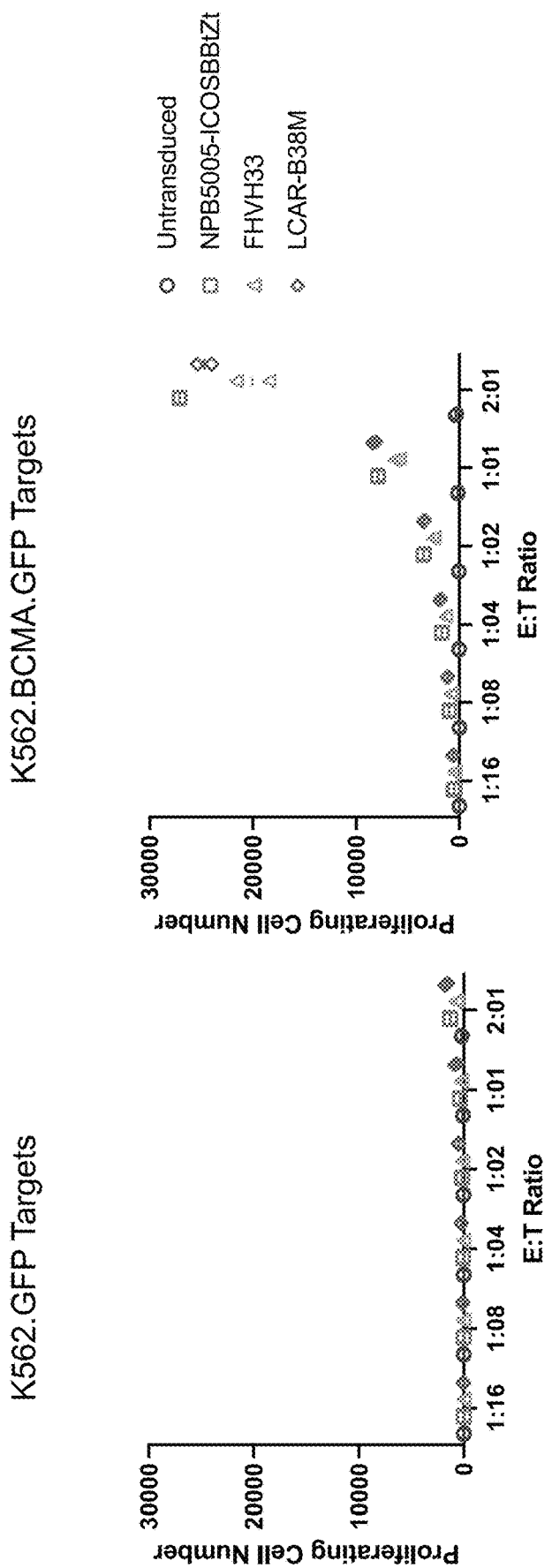
Figure 8D:
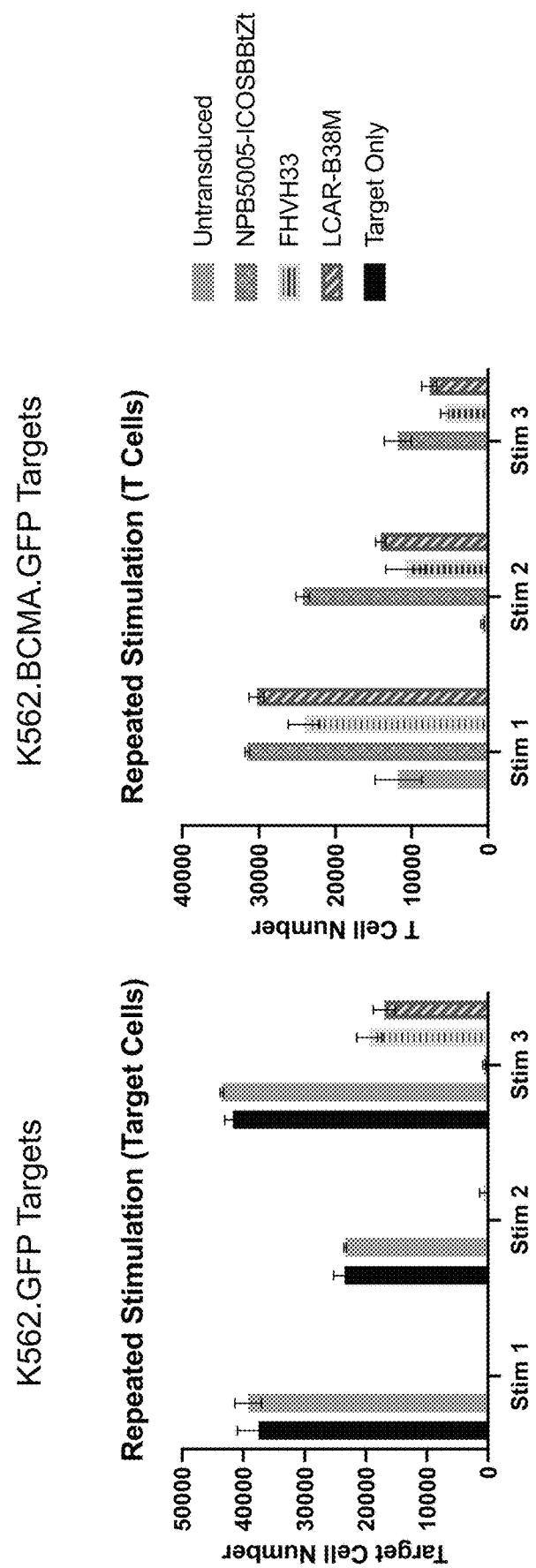

NPB5005-ICOSBBtZt resulted in lower PD-1 expression in antigen-stimulated CAR-T, as indicated in FIGS. 6A-6C. The decreased PD-1 expression on the surface of T cells was observed in both RPMI-8226 (FIG. 6B) and U266 (FIG. 6C) cell lines. It was further observed that the 3$^{rd}$ generation costimulatory domains are necessary for the full functionality of truncated CD3zeta chain-based CAR receptors of the present disclosure, as demonstrated by IL2 production comparison in FIG. 7A and CAR positive cells in FIG. 7B.

Figure 9A:
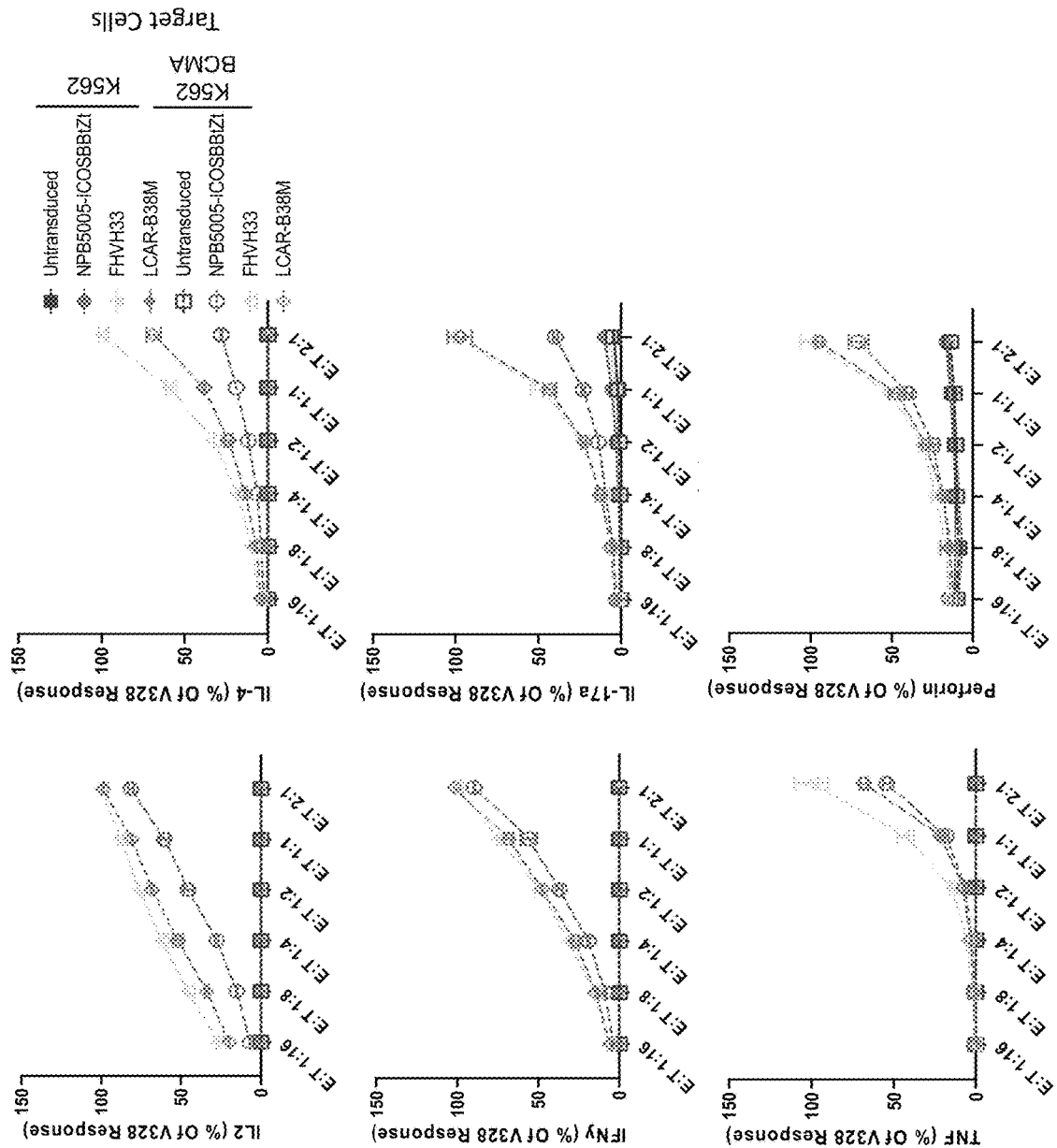
FIGS. 9A-9B depict the cytokine production and PD1 expression properties of a BCMA-CAR of the present disclosure ("NPB5005-ICOSBBtZt") are maintained in clinical vector format, which lacks a eukaryotic selection marker. NPB5005-ICOSBBtZt maintains lower cytokine production and PD1 expression.
Figure 9B:
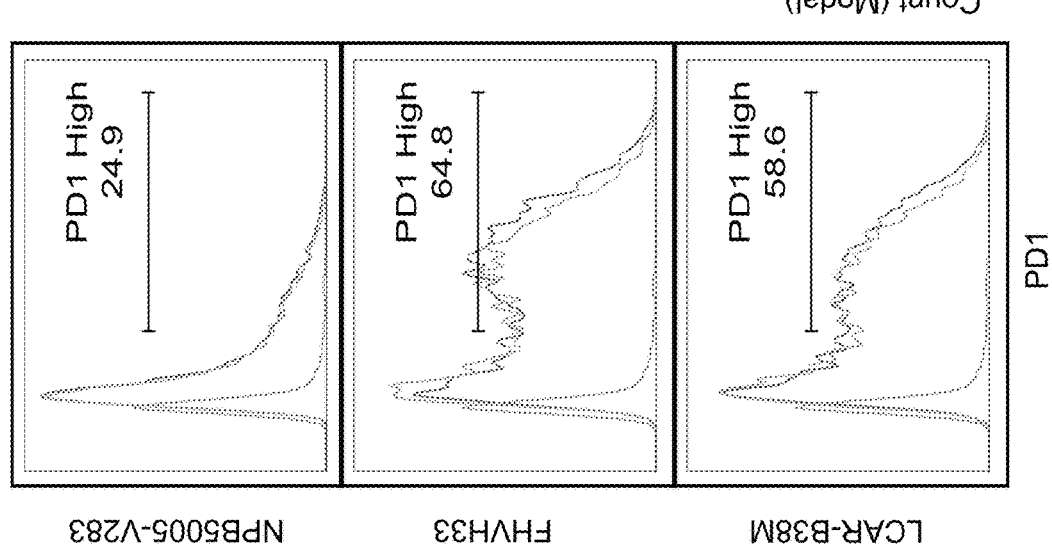
Figure 10A:
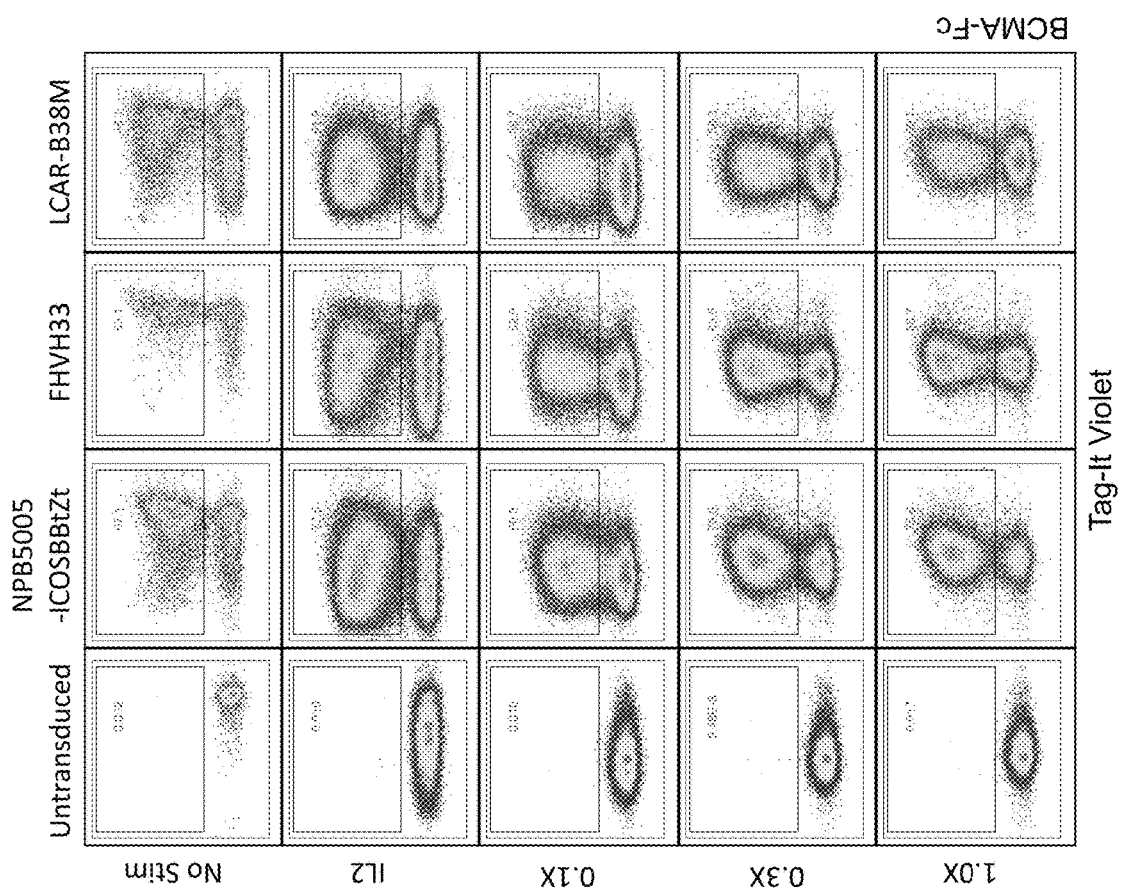
Figure 10B:
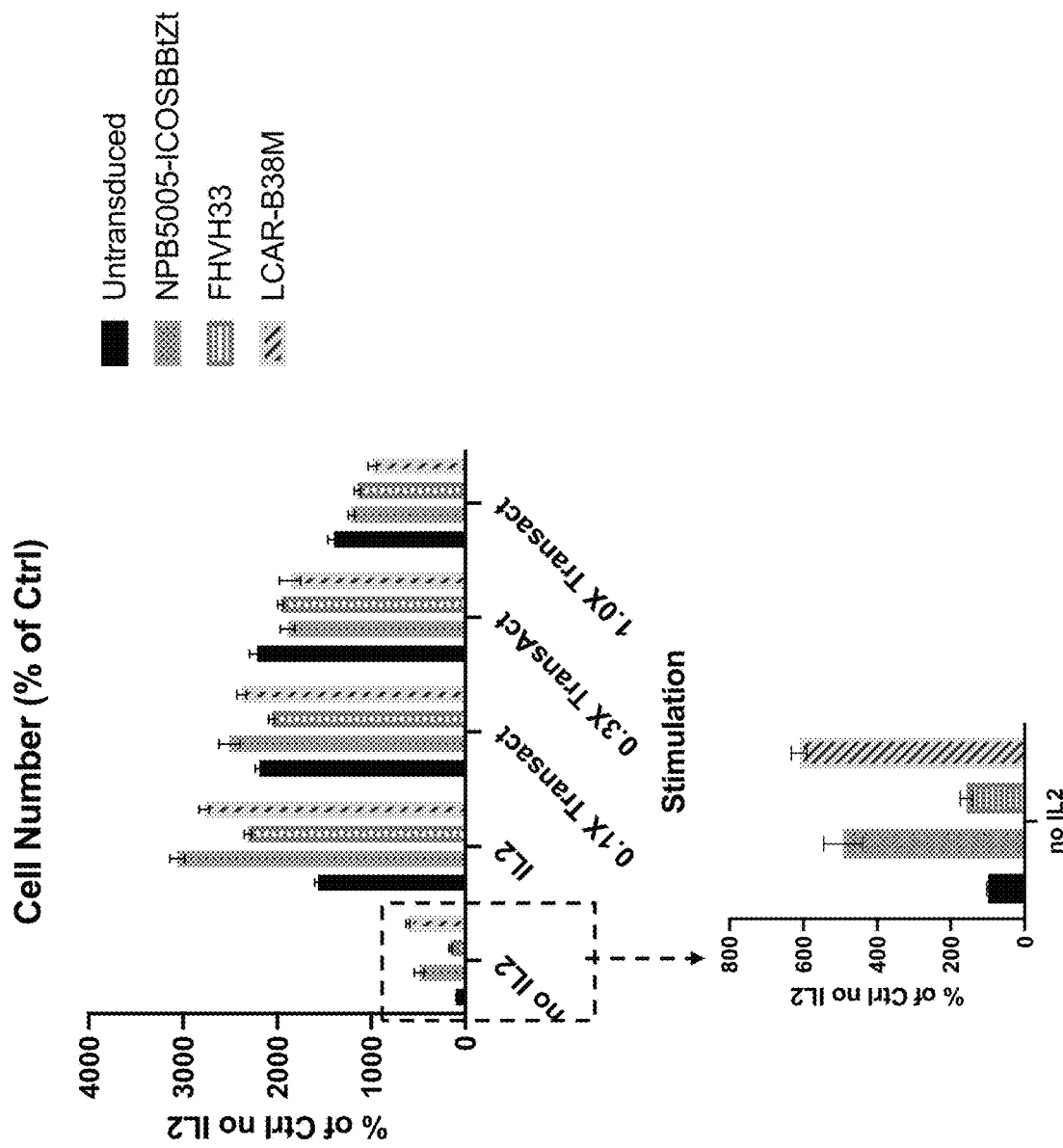

BCMA-CAR of the present disclosure was cloned into clinical vector format, which lacks a eukaryotic selection marker. Functionality of the BCMA-CAR was assessed from the new vector, including proliferative and cytolytic phenotypes (FIGS. 8A-8D) and reduced cytokine production and PD1 expression (FIGS. 9A-9B). Intermediate CAR-intrinsic tonic signaling (FIGS. 10A-10C) was also determined, with NPB5005-ICOSBBtZt demonstrating a level of tonic signaling in-between the two reference CAR-T cells; cell survival was comparable to LCAR-B38M in the absence of IL2 or CAR ligand (FIG. 10A-10B), but tonic cytokine production was strikingly reduced (FIG. 10C).

Figure 11A:
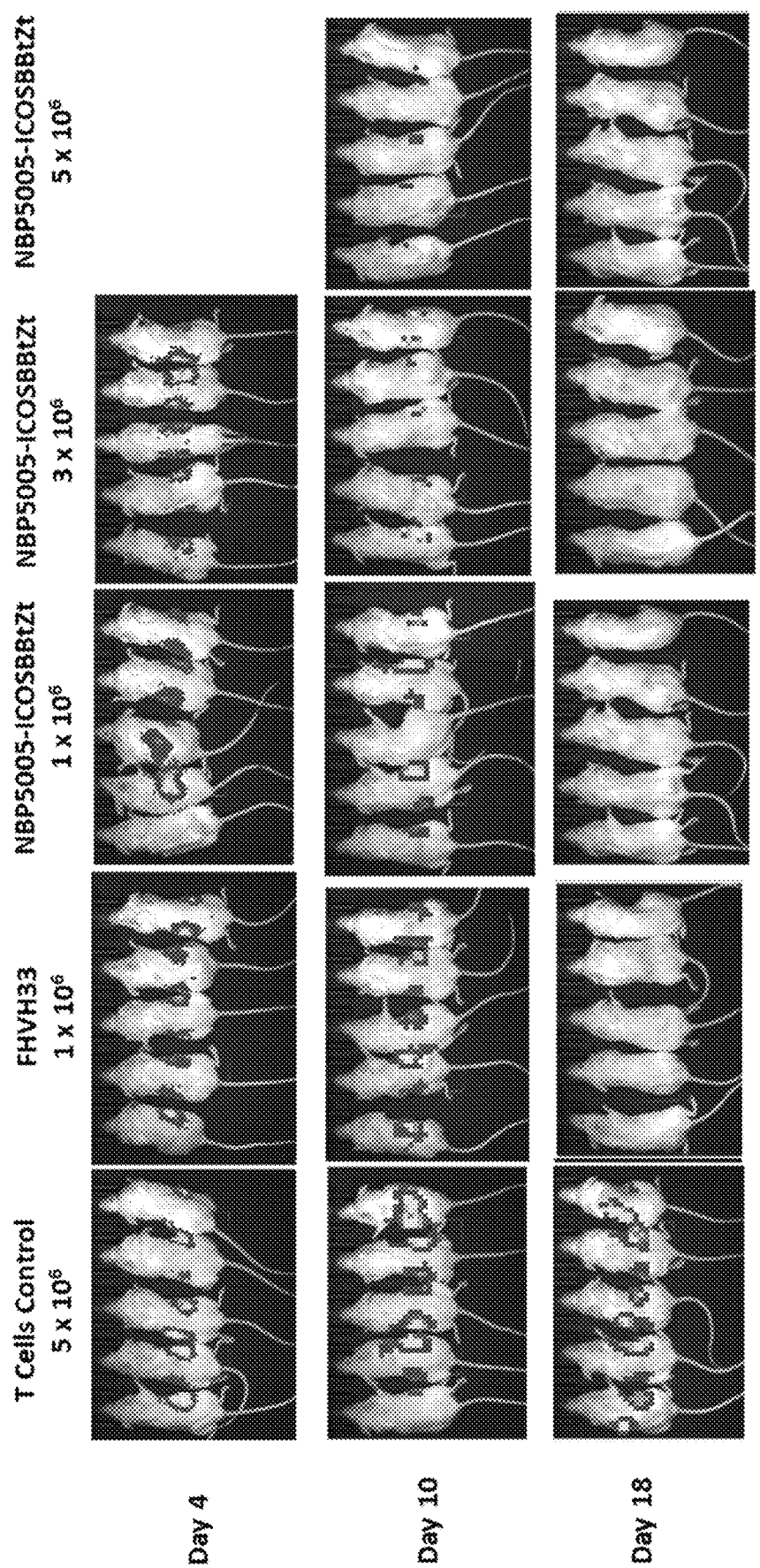
FIGS. 11A-11D depict dose response of a BCMA-CAR of the present disclosure in a murine model in vivo.
Figure 11B:
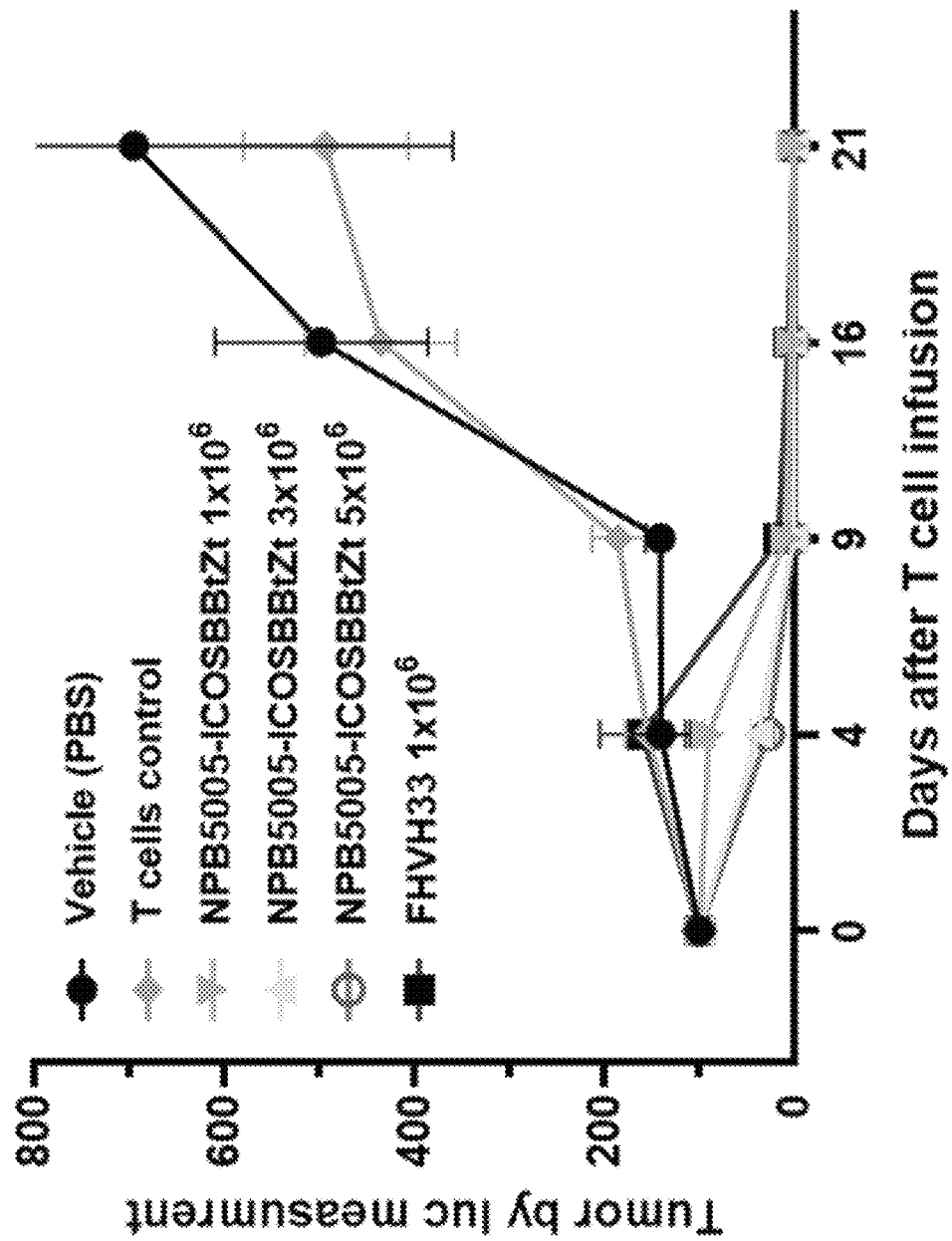
Figure 11C:
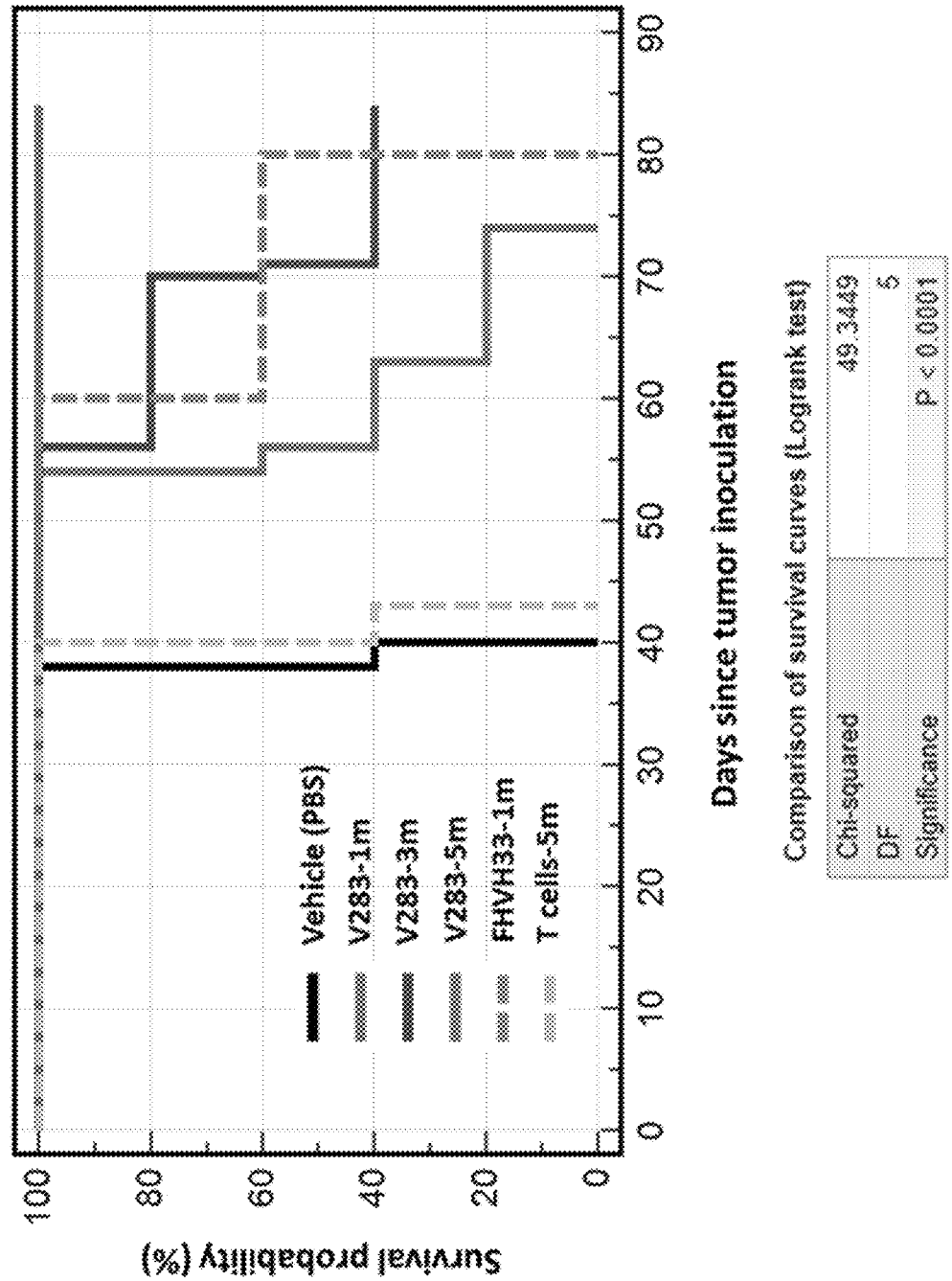
Figure 11D:
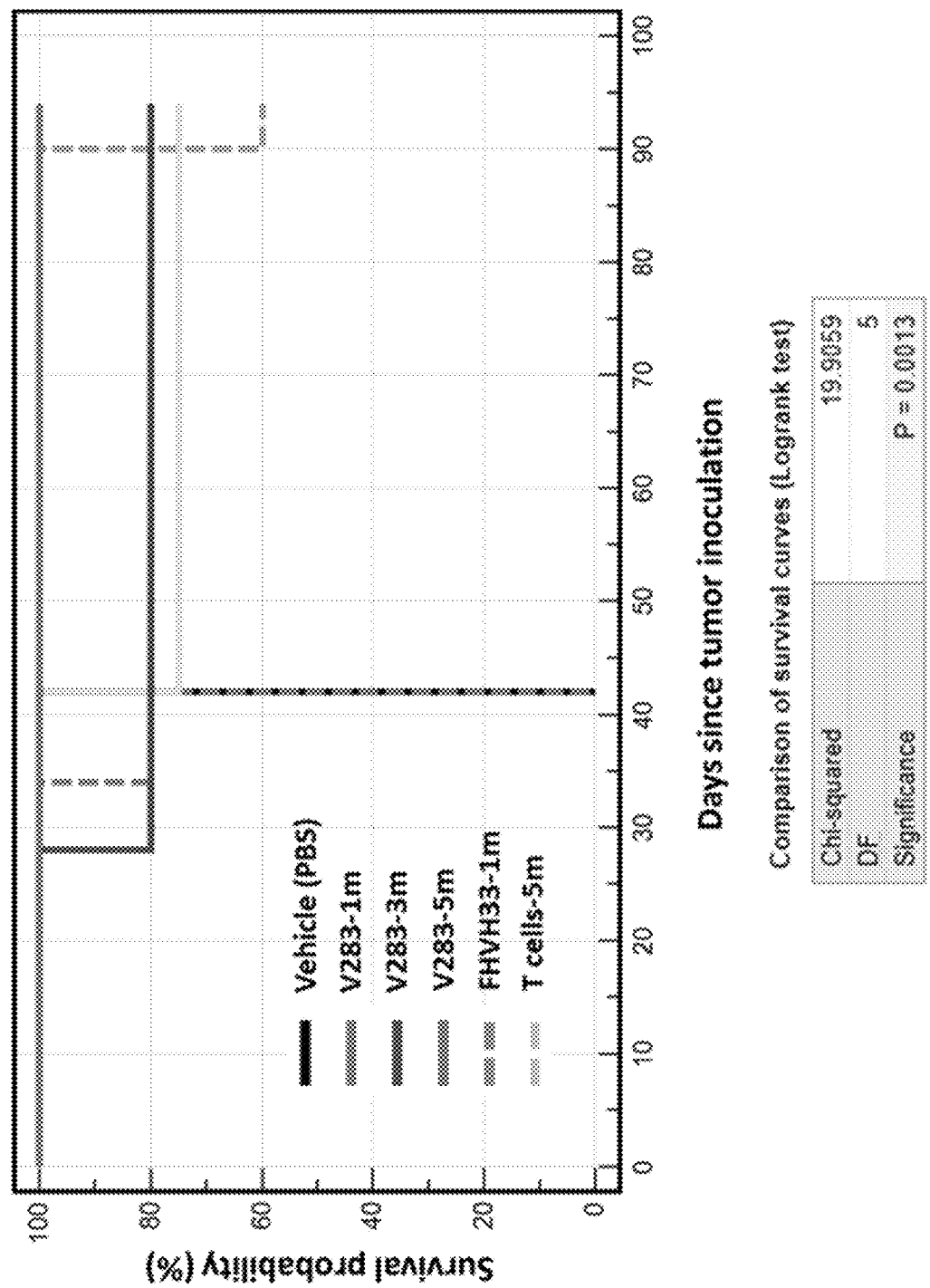

Example 5: BCMA-CAR Shows Dose-Dependent Efficacy in a Xenograft Murine Model In Vivo To assess efficacy in vivo, MM.1S cells were injected into mice at $1\times10^6$, $3\times10^6$, and $5\times10^6$ via tail vein injection. Intravital imaging of tumor burden at days 4, 10, and 18 (FIG. 11A), as well as quantification of secreted *Gaussia* luciferase (FIG. 11B), demonstrated significantly reduced tumor burden in all doses tested, and a dose-dependent effect. Survival curves of female (FIG. 11C) and male (FIG. 11D) mice demonstrated enhanced survival of treated subjects, with mice receiving NPB5005-ICOSBBtZt demonstrating about 100% survival over 90-days post-dose.

Taken together, the results described herein show that T cells expressing the modified 3$^{rd}$ generation BCMA-CAR of the present disclosure (e.g., NPB5005-ICOSBBtZt) can be used to treat cancer with high efficacy and significantly lower adverse events. Specifically, expression of NPB5005-ICOSBBtZt results in increased effector function, proliferation, and persistence, while minimizing cytokine release. As shown above, NPB5005-ICOSBBtZt kills multiple myeloma cell lines expressing BCMA with a comparable efficacy as the leading BMCA-CAR T cell therapies, producing reduced toxic cytokines and expressing lower levels of surface PD-1. Therefore, NPB5005-ICOSBBtZt is more resistant to negative signaling from cells in the tumor microenvironment. Following repeated stimulation with target cells, NPB5005-ICOSBBtZt proliferates to higher numbers compared to alternative BCMA-CAR T cells.

What is claimed is:

1. A chimeric antigen receptor that binds B cell maturation antigen (BCMA-CAR), comprising:
    (a) an extracellular domain comprising the amino acid sequence of SEQ ID NO: 8;
    (b) a transmembrane domain; and
    (c) a chimeric intracellular domain comprising a first, a second and at least a third signal transduction domain, wherein
        the first signal transduction domain consists of an ICOS intracellular domain as set forth in SEQ ID NO: 2,
        the second signal transduction domain consists of a truncated CD137 (4-1BB) intracellular domain as set forth in SEQ ID NO: 3, and
        the at least third signal transduction domain consists of a truncated CD3ζ domain as set forth in SEQ ID NO: 4,
    wherein the BCMA-CAR comprises the amino acid sequence as set forth in SEQ ID NO: 5.

2. An isolated nucleic acid encoding the BCMA-CAR of claim 1, or a vector comprising a nucleic acid encoding the BCMA-CAR of claim 1.

3. An isolated T cell comprising the nucleic acid or vector of claim 2.

4. The isolated T cell of claim 3, wherein the cell is: a) an allogeneic T cell; or b) an autologous T cell.

5. The isolated T cell of claim 3, wherein the T cell is a naive T cell, an early memory T cell, a stem cell-like T cell, a stem memory T cell (TSCM), a central memory T cell (TCM), or a regulatory T cell (Treg).

6. The isolated T cell of claim 3, wherein the T cell co-expresses the BCMA-CAR with at least one endogenous co-stimulatory molecule selected from CD28, CD2, OX-40, ICOS, CD28, CD3, CD4, CD8, CD40L, and a combination thereof.

7. A composition comprising the isolated T-cell of claim 3.

* * * * *